(12) United States Patent
Watson et al.

(10) Patent No.: US 6,380,362 B1
(45) Date of Patent: Apr. 30, 2002

(54) POLYNUCLEOTIDES, POLYPEPTIDES EXPRESSED BY THE POLYNUCLEOTIDES AND METHODS FOR THEIR USE

(75) Inventors: James D. Watson; James G. Murison, both of Auckland (NZ)

(73) Assignee: Genesis Research & Development Corporation Ltd. (NZ)

( * ) Notice: Subject to any disclaimer, the term of this patent is extended or adjusted under 35 U.S.C. 154(b) by 0 days.

(21) Appl. No.: 09/724,864

(22) Filed: Nov. 28, 2000

Related U.S. Application Data

(60) Provisional application No. 60/171,678, filed on Dec. 22, 1999.

(51) Int. Cl.[7] .................. C07K 14/00; A61K 38/00; A61K 45/00; A61K 39/00
(52) U.S. Cl. .................. 530/350; 530/351; 514/2; 514/8; 514/12; 424/85.1; 424/184.1; 536/23.5
(58) Field of Search .................. 530/350, 351; 536/23.5; 424/85.1, 184.1; 514/2, 8, 12

(56) References Cited

PUBLICATIONS

Dumas et al., "Human 5' EST related polypeptide SEQ ID No: 880", Oct. 21, 1999, Database A_Geneseq_0401, Accession No: Y64719.*

* cited by examiner

*Primary Examiner*—Karen Cochrane Carlson
*Assistant Examiner*—Rita Mitra
(74) *Attorney, Agent, or Firm*—Ann W. Speckman; Janet Sleath

(57) ABSTRACT

Novel polynucleotides including partial and extended sequences, and open reading frames, are provided, together with probes and primers, DNA constructs comprising the polynucleotides, biological materials and organisms incorporating the polynucleotides, polypeptides expressed by the polynucleotides, and methods for using the polynucleotides and polypeptides.

3 Claims, No Drawings

SEQUENCE LISTING

```
<160> NUMBER OF SEQ ID NOS:  72

<210> SEQ ID NO 1
<211> LENGTH: 2401
<212> TYPE: DNA
<213> ORGANISM: Rat

<400> SEQUENCE: 1
gaggccacag ttatcaccac ggagaagaga gagaggccag cgcccctag  agagctcctg      60 gtacccagg  cagaagtgac agcacgtagc ctccggctcc agtgggtccc tggcagcgat     120
ggggcctccc cgatccggta ctttaccgtg caggtgcgag agctgccggg tggagaatgg     180
cagacctact cctcgtctat cagccacgag gccacactct gtgctgttga aaggctgagg     240
cctttcacct cctacaagct gcgcctgaag gccaccaacg acattgggga cagtgacttc     300
agtgcagaaa cagaggctgt gaccacactg caagatgttc caggagagcc accaggatct     360
gtctcagcca caccgcacac cacgtcctca gttctgatcc agtggcagcc tccccgggat     420
gagagcttga atggccttct gcaaggctac aggatctact accgtgagct ggagtccgag     480
acaggcctga gccctgaacc caagacactc aagagcccct ctgccttacg tgctgaactc     540
acggctcaaa gcagcttcaa gaccgtgaac agcagctcca cattaacgac ctatgaatta     600
acacatctga agaagtaccg gcgctatgaa gtcatcatga ctgcctataa catcattggt     660
gagagcccag ccagtgtacc agtggaggtc ttcgttggtg aggctgcccc agcaatggcc     720
ccacagaaca tccaggtgac cccactcaca gccagccagc tggaggtcac atgggacccg     780
```

-continued

| | | |
|---|---|---|
| ccaccccag agagccagaa tgggaacatc caaggttaca aggtttacta ctggaggca | 840 | |
| gacagtcgta atgagacgga gaaatgaag gtcctctttc tccctgagcc tgtggtaaag | 900 | |
| attaaggatc tcaccagcca cacaaagtac ctggtcagca tctcagcctt caacgctgct | 960 | |
| ggtgacgggc ccagaagtga cccatgccag ggacgcacac accaggcagc tccagggccc | 1020 | |
| ccaagcttct tggaattctc agaaataaca tctaccacac tcaacgtatc ctgggggag | 1080 | |
| ccatcggcag ccaacggcat cctacagggc tatcgagtgg tgtatgaacc cttagcacca | 1140 | |
| gtgcaaggcg tgagcaaggt ggtgaccgtg atgtgaaag ggaactggca acggtggctg | 1200 | |
| aaggtgcggg acctcaccaa gggagtgacc tatttcttcc gtgttcaggc gcgaaccatc | 1260 | |
| gcctacgggc cagaactcca agccaatgtc actgcagggc cagccgaggg gtccccagga | 1320 | |
| tctccaagaa atgtccttgt caccaaatct gcctctgagc tgacccttca gtggacagaa | 1380 | |
| gggaacacag gaacacacc cactacaggc tacgtcatag aagccagacc atcagatgaa | 1440 | |
| ggcttatggg acatgtttgc aaaggacatt cccaggagtg ctacgtcata caccgtgggt | 1500 | |
| ctggacaagc tgcggcaagg ggtgacctac gagttccggg tggtggccgt gaacaaggca | 1560 | |
| ggctttgggg aacccagccg cccttccatt gcagtgtcag cacaagctga agcccgttc | 1620 | |
| tatgaggagt ggtggttcct gctggtgata gcgctctcca gcctcctcct cgtcctcctg | 1680 | |
| gtggtcttcg tgctggtcct gcatgggcaa agcaagaagt acaagaactg tggctcaggt | 1740 | |
| aagggcatct ccaacatgga ggagacagtg accctggata tggagggtt tgccgccttg | 1800 | |
| gaactcaaca gtcgtcacct caatgtcaag agcaccttct caaagaagaa cggaaccaga | 1860 | |
| tcccccacccc gaccaagccc cggaggtctg cactactctg acgaagacat ctgcaacaaa | 1920 | |
| tacaacggtg cggtgctgac agagagtgtg aacctcaagg agaaatcggt ggatgggtcg | 1980 | |
| gaatcggagg cttctgactc agactacgag gaagccctgc ccaagcactc ctttgtcaac | 2040 | |
| cactacatga gcgaccccac ctactacaac ttttggaagc ggcgtccccc tgccgcagca | 2100 | |
| ccgcacaggt acgaggcggt ggcaggggcc gaagctggcc cgcacctgca cacagtcatc | 2160 | |
| accacacaga gcgcgggcgg agtttacaca ccagctggcc ccggagcccg ggccccctc | 2220 | |
| accggcttct cctccttcgt gtgacgtcac gcctccatca gggtagacgg gtgcagaact | 2280 | |
| tctggagtct atttttgtta agacaatcaa ctccgataac tgagctgaat tttttttgtt | 2340 | |
| taaaaaata ataataattt tgataagcga aaaaaaaaa aaaaaaaaa aaaaaaaaa | 2400 | |
| a | 2401 | |

<210> SEQ ID NO 2
<211> LENGTH: 1258
<212> TYPE: DNA
<213> ORGANISM: Mouse

<400> SEQUENCE: 2

| | | |
|---|---|---|
| cacacgcccc gcgtgtgcgg agcccttatt tacttcgcag aagagccttc agaccccctc | 60 | |
| ctaacaagtg tggaaagcat cacggcgacg cgatgttggg gacactggtc tggatgctcg | 120 | |
| cggtcggctt cctgctggca ctggcgccgg ccgcgcggc gggcgcgctg aggaccggga | 180 | |
| ggcgccggc gcgccgcgg gactcgcgcg gaccggccga ggagctcctg gagcagctgt | 240 | |
| acggcggct ggcggccggc gtgctcagcg ccttccacca cacgctgcag ctcgggccgc | 300 | |
| gcgagcaggc gcgcaatgcc agctgccgg ccggggcag ggccgccgac cgccgcttcc | 360 | |
| ggccacccac caacctgcgc agcgtgtcgc cctgggcgta caggatttcc tacgaccctg | 420 | |
| ctcgcttcc gaggtacctg cccgaagcct actgcctgtg ccgaggctgc ctgaccgggc | 480 | |

-continued

```
tctacgggga ggaggacttc cgctttcgca gcacacccgt cttctctcca gccgtggtgc      540
tgcggcgcac agcggcctgc gcgggcggcc gctctgtgta cgccgaacac tacatcacca      600
tcccgtgggg ctgcacctgc gtgcccgagc cggacaagtc cgcggacagt gcgaactcca      660
gcatggacaa gctgctgctg gggcccgccg acaggcctgc ggggcgctga tgccggggac      720
tgcccgccat ggcccagctt cctgcatgca tcaggtcccc tggccctgac aaacccacc      780 ccatgatccc tggccgctgc ctaattttt caaaaggaca gctacataag ctttaaatat      840
atttttcaaa gtagacacta catatctaca actattttga atagtggcag aaactatttt      900
catattagta atttagagca agcatgttgt ttttaaactt ctttgatata caagcacatc      960
acacacatcc cgttttcctc tagtaggatt cttgagtgca taattgtagt gctcagatga     1020
acttccttct gctgcactgt gccctgtccc tgagtctctc ctgtggccca agcttactaa     1080
ggtgataatg agtgctccgg atctgggcac ctaaggtctc caggtccctg gagagggagg     1140
gatgtggggg ggctaggaac caagcgcccc tttgttcttt agcttatgga tggtcttaac     1200
tttataaaga ttaaagtttt tggtgttatt ctttcaaaaa aaaaaaaaaa aaaaaaa       1258
```

<210> SEQ ID NO 3
<211> LENGTH: 3043
<212> TYPE: DNA
<213> ORGANISM: Mouse

<400> SEQUENCE: 3

```
cgcgtctccc gccgcaccca cccgtcgctg tatcaagcaa aagcgaaagg aagccgagcg       60
gtcccgcgtg gcgtggcgtg ggcggggagg tggctgcgcg ctctagctcc gcgggaccag      120
gctgccgctt tgtgacttca ccggtttcgc aacaagccag gaccgcccgc gccccaccca      180
cccggctgcc cgtccgccct ccgccctcgg gtctctgagc gcttccctcc ctccggggct      240
gggcctgtcc cggccgtccc ggagtctctg tcccgccgcg ccgttagctg tctgtgtctt      300
ggccaccgcc tccaggcagt ccgcagcaag ccagcttctt ggtccgacga gctcagcgcc      360
ctctcaccgc gatgctgtgc ttcctcaggg gaatggcttt cgtccccttc ctcctggtga      420
cttggtcgtc cgcagccttc atcatctcct acgtggtcgc ggtgctctct gggcacgtca      480
acccctttct cccctatatc agtgacacag gaacaactcc tccagagagt ggtattttg      540 gattcatgat aaacttctct gcatttcttg gcgcagctac gatgtacaca agatacaaga      600
tagtggagaa gcagaatgag acctgctact tcagcactcc cgttttaac ttggtgtcct      660 tggcgcttgg attggtggga tgcatcggaa tgggcatcgt agccaacttc caggagttag      720
ccgtgcctgt ggtccatgat ggcggtgcgc ttctggcttt cgtctgcggg gtggtgtaca      780
cgctcctgca atcgatcatc tcctacaaat cctgtcccca gtggaacagt ctcaccacgt      840
gccatgtcag gatggccatc tccgctgttt cgtgcgcagc tgtcgtcccc atgattgcct      900
gtgcttcact catttctata accaagctgg aatggaatcc aaaagaaaag gattatatat      960
atcacgtggt gagcgccatc tgtgagtgga ccgtggcttt tggttttatt ttctatttcc     1020
taacattcat ccaagatttc cagagtgtca ctctaaggat atccacagaa atcaatgacg     1080
acttttgaaa gatcgagaat cctgtctcat tcagggagtg tcgcagacag tttctggaag     1140
tggacagagg acggacgggc ttggatgtca ccctgatggg gactttatct gtggcacatc     1200
cgggacttga atttcattaa gagttcctag tagttcaatt tacaaaggta tgtttccctg     1260
gaggatggat agcaccaacg acactgtagc aatatttta tattttctaa aacaatcttt     1320
```

-continued

| | | |
|---|---|---|
| tatgaacaaa ttcatatgca aagaagacga ggcattgcag aaaggggagg attattcttg | 1380 |
| tatagattct ttagacttt tatgtaataa tgatttatga aaatacacta agagaaaaaa | 1440 |
| atgttaagtt tagtactttt tattaaagaa gccaaatcag ggcatattca ctttaaaatt | 1500 |
| tcattttta aatacagtga cctgcataca ttttcatcac aagagcactt atacaattca | 1560 |
| attcatagtg attatatacc ctaatggtat agatttaggt aataaacgaa cactttaaag | 1620 |
| cactctgaat tttcagtgca ttaaacaaat gcttttatag tgaaggactc aaaaccattt | 1680 |
| acagtgcaca ttaaccagcg aatgtggaag acctcggttc gaaaatttag cccctcatt | 1740 |
| tacttctcca agggacccac agctttactg ccgctgttaa tggtgggccc gggaactaat | 1800 |
| tccaggtagg atgggctcat caggccagct tagaaatgat caaactgccc ttctctgtga | 1860 |
| ccgggcagca caagttcaat tcacttctca gtttccctgt aagccaaaga gaatgcagat | 1920 |
| ccaagtcagg gagaaaggag agcgctcata gaaacttcca gatgtgggct gctgcctatc | 1980 |
| tgctcctatc aatgcctgtg ggccactata agggagtcag gcccttccg aagcaaggcc | 2040 |
| tggagactct acctttcatg cagttccacca atggcaaaga aacgccagct gttgtggagg | 2100 |
| aagaagtgga taacaagacc ccccagtctg ggccagtagg agctgcccca agggcacgtt | 2160 |
| ccaaggacag agaccatttg acagccttta gtgaaagggt acctggcgat gaaggggcac | 2220 |
| acagcagtgc ctcctttggc tgctaagtga agggtgctgc tcagcaggca cttctgccat | 2280 |
| gacatcctgt gtcttcttcc tcagtgtgca gtggtggcaa ccaacgtcca tttctgagtc | 2340 |
| ccctgtaact tttcacagta ccgaacatgc ccattgtaac actggaacag aaagacagtg | 2400 |
| gctgtcattc tgatgagtga gagggagtc gatacatttc ctgtggaagc tggggcggac | 2460 |
| tgaatgcatg ctgttctttg ctttgagcgg gagccttggt tgatgccttc ccagaatgca | 2520 |
| cttggctctc ttcgcttcca ctggagaccc gaccacgtgc ctttacccat agtggaacac | 2580 |
| agtgccttgt ggcatgcaat aggtgcttaa taaatactca ttgaatgtat gcacgcataa | 2640 |
| atggatgaac aagtaacgac tagggatgtt tgaggtgcta agggtttttt ttactctagt | 2700 |
| tcacgggtat tctaaggtca acagctagtc tgtgccaatt agtaatgttg tctgttttgc | 2760 |
| tttgtgaact attctcgttt ccacctgttc cagctgtgtg agcttcatga ttgtgtgaca | 2820 |
| actctctcct ggacagatag cacagaaatt gttacatggg ctaaacctgt cttggcaaac | 2880 |
| cgaggaggcc cccaaatcac actctgcaga ttccatgcga cttctagttt tatccctgtt | 2940 |
| ttggtgttat ttttaatttc tacaaatatg tatttccttg gactttgtac ccgagaaagt | 3000 |
| aaaataaaat atttctttat tttaaaaaaa aaaaaaaaaa aaa | 3043 |

<210> SEQ ID NO 4
<211> LENGTH: 2515
<212> TYPE: DNA
<213> ORGANISM: Mouse

<400> SEQUENCE: 4

| | | |
|---|---|---|
| gctgcgcctg ctgctggcct gggtggccgc ggtgcccgca ctgggccagg tcccctggac | 60 |
| gccggagcct cgagccgcgt gcggcccag cagctgctac gcgctctttc cccggcgccg | 120 |
| cacattcctg gaagcttggc gggcgtgccg cgaattgggg ggcaacctgg ccacaccgcg | 180 |
| gaccccagag gaggcccagc gtgtggacag cctggtgggg gtcgggccgg ccaacgggct | 240 |
| gctatggatt gggttgcagc ggcaggctag gcaatgccag ccgcacgcc cactgcgggg | 300 |
| cttcatatgg accacgggag accaggacac cgccttcacc aactgggccc agccggctac | 360 |
| ggaaggaccc tgcccagccc agcgctgtgc agcccttgag gccagcggag agcatcgctg | 420 |

-continued

```
gctcgaaggc tcgtgcacac tggctgtcga cggctacctc tgccagtttg gttttgaggg    480
tgcctgccct gccttgccgc ttgaggtggg tcaggccggt cccgctgtct acaccacacc    540
cttcaacctg gtttccagcg agttcgaatg gctgcccttt ggctccgtgg cagctgtgca    600
gtgccaagct ggcaggggag cttctctgct gtgcgtgaaa cagccttcag gtggcgtggg    660
ctggtcccag actggcccgc tgtgcccagg gactggctgt ggtcctgaca atgggggttg    720
cgaacatgag tgtgtggaag aggtggacgg tgctgtgtcc tgccgctgca gtgaaggctt    780
ccgtctagca gcagatgggc acagttgtga agacccctgt gcccaggccc ctgtgagca    840 gcagtgtgaa cctggagggc acaaggcta tagctgccac tgtcgccttg gcttccggcc    900
agctgaggat gatccacacc gctgcgtgga cacggatgag tgccagattg ctggtgtgtg    960
ccagcagatg tgtgtcaact atgttggtgg ctttgagtgt tactgcagcg agggtcacga   1020
gcttgaggca gatggtatca gctgtagccc tgcaggagcc atgggtgccc aggcttccca   1080
ggatctcaga gatgagttgc tggatgatgg agaagaaggg gaggatgaag aggagccctg   1140
ggaggacttt gatggcacct ggacagagga acagggatc ctatggctgg cacctacaca   1200
tccacctgac tttggcctgc cctataggcc caacttccca caggatggag agcctcagag   1260
attgcacctg gagcctacct ggccaccccc acttaaggcc cccaagggcc ccaacaacc    1320 cccaagggg gccgccaaaa cgcccaaggg gaaccccgcc aacccaaccc acactacctt    1380
ctgcccacaa gacctctgtt atttcagcta cacgcccacc cctgagccct gtccaccca    1440 ctgccatggc ccctgccaca cctccagctg tgttctctga gcaccagatc cccaaaatca   1500
aggccaatta tccagacctg ccttttggcc acaagcctgg gataacctcg gccactcacc   1560
cagcacggcc tcctccgtac cagccccca ttatctcaac caactatccc caagtcttcc   1620
ctccccacca ggccctatg tctccagata cccacactat cacttatttg cctccagtcc   1680 ccctcacct tgatcctggg gataccactt ctaaagccca tcaacaccct ttgctcccag   1740
atgctccagg tatcagaacc caggcccccc agctttctgt ctcagctctc cagccccctc   1800
ttcctaccaa ctccaggtct tctgtccatg aaactcctgt gcctgctgcc aaccagcccc   1860
cagccttccc ttcttctccc ctccccctc agaggcccac taaccagacc tcatctatca   1920
gccctacaca ttcctattcc agagccctc tagtcccaag ggaaggagtt cccagtccca   1980
aatcagtgcc acagctgccc tcggtgccct ccacagcagc tccaacagcc ctggcagagt   2040
caggtcttgc aggccaaagc caaagggatg accgctggct gctggtggca ctcctggtgc   2100
caacatgtgt cttcttggtg gtgctgcttg ccctgggcat tgtgtactgc actcgctgtg   2160
gctcccacgc acccaacaag cggatcacgg actgctatcg ctgggtcaca catgctggga   2220
acaagagctc aacagaaccc atgcccccca gaggcagcct tacagggta cagacctgta   2280 gaaccagtgt gtgatgggt gcagatgccc ctttgtggga tagaagaaaa ggacttgctt   2340
tggacacatg gctgagacca caccaaggac ttatgggggc tgcccagctg acagaggagg   2400
ttctgttctt tgagcccagc atccatggca aaggacacac caggactcca ggacctcaag   2460
gggtgggtgc tgggatcttc tccaataaat ggggtgccaa cctctaaaaa aaaaa         2515
```

<210> SEQ ID NO 5
<211> LENGTH: 1587
<212> TYPE: DNA
<213> ORGANISM: Mouse

<400> SEQUENCE: 5

-continued

| | |
|---|---|
| gcggcgcggg tagagggcgg tgggcggcga gcggcgatgg gccgcgcctg gggcttgctc | 60 |
| gttggactcc tgggcgtcgt gtggctgctg cgcttgggcc acggcgagga gcggcggccg | 120 |
| gagacagcgg cacagcgctg cttctgccag gttagtggtt acctggacga ctgtacctgt | 180 |
| gatgtcgaga ccatcgataa gtttaataac tacagacttt tcccaagact acaaaagctt | 240 |
| cttgaaagtg actactttag atattacaag gtgaacttga agaagccttg tccttctgg | 300 |
| aatgacatca accagtgtgg aagaagagac tgtgccgtca aaccctgcca ttctgatgaa | 360 |
| gttcctgatg gaattaagtc tgcgagctac aagtattctg aggaagccaa ccgcattgaa | 420 |
| gaatgtgagc aagctgagcg acttggagcc gtggatgagt ctctgagtga ggagacccag | 480 |
| aaagctgtac ttcagtggac caagcatgat gattcgtcag acagcttctg cgaaattgac | 540 |
| gatatacagt cccccgatgc tgagtatgtg gacttactcc ttaaccctga gcgctacaca | 600 |
| ggctacaagg ggccagacgc ttggaggata tggagtgtca tctatgaaga aaactgtttt | 660 |
| aagccacaga caattcaaag gcctttggct tctgggcgag gaaaaagtaa agagaacaca | 720 |
| ttttacaact ggctagaagg cctctgtgta gaaaagagag cattctacag acttatatct | 780 |
| ggcctgcacg caagcattaa tgtgcatttg agtgcaaggt atcttttaca agatacttgg | 840 |
| ctggaaaaga aatggggtca caatgtcaca gagttccagc agcgctttga tgggattctg | 900 |
| actgaaggag aaggcccacg aaggctgagg aacttgtact tcctgtacct gatagagtta | 960 |
| agggctctct ccaaagtgct tccatttttt gagcgtccag attttcagct cttcactggg | 1020 |
| aataaagttc aggatgcaga aaacaaagcg ttacttctgg agatacttca tgaaatcaag | 1080 |
| tcatttcctt tgcacttcga tgagaattct ttttttgctg gggataaaaa cgaagcacat | 1140 |
| aaactaaagg aggacttccg gctacacttt aggaacattt caagaatcat ggactgtgtt | 1200 |
| ggctgcttca gtgccgcct gtggggcaag cttcagacgc aggggctggg cactgctctg | 1260 |
| aagatcttgt tttccgaaaa actgatcgca aatatgccgg aaagcggacc aagttatgag | 1320 |
| ttccagctaa ccagacaaga aatagtatca ctgtttaatg catttggaag gatttccaca | 1380 |
| agtgtgagag aactagagaa cttcaggcac ttgttacaga atgttcactg aggaggacgg | 1440 |
| ttggaatgtg cctgtttctg cacagggaa tttgaagggc aaaatctctt ttagccccat | 1500 |
| ggttgcaatg tactgtccta agcccaacgt ttatataaac ctgcttttgt taagaaaaaa | 1560 |
| aaaaaaaaaa aaaaaaaaa aaaaaaa | 1587 |

<210> SEQ ID NO 6
<211> LENGTH: 2494
<212> TYPE: DNA
<213> ORGANISM: Rat

<400> SEQUENCE: 6

| | |
|---|---|
| acttgaactg gcagataaaa aagtatgaca ccaaggcagc ttactgccag agcaagttgg | 60 |
| ctgttgtcct cttcaccaag gagctgagtc gccggctgca aggcactggt gtgactgtca | 120 |
| atgcgctgca ccctggcgtg gccaggacgg agctggggcg acatacaggc atgcacaact | 180 |
| ctgcgttctc tggcttcatg cttgggccct tcttctggct gctgttcaag agtccccagc | 240 |
| tggcggccca gcccagcaca tacctggctg tggcagagga actggagagt gtctctggga | 300 |
| agtactttga tggactcaga gagaaggctc catctcctga ggctgaagat gaggaagtag | 360 |
| cccggaggct ttggactgaa agtgcccatt tggtgggctt ggacatggct catgggtcct | 420 |
| ctgggagagg acattccatc tccagataac cttcagaaat ccagatggag cctcatcatc | 480 |
| ctctagggc agtgttggta ttgttagaat ctcaagactg tggatgttgg ctgccatgac | 540 |

| | |
|---|---|
| cctcatcatc ctctaggagc agtgttgtac tactcgaact gaagactgtg gatgctggct | 600 |
| gccatcctct gggtggctgt gttggtccta gcattattgt tagctggctg ctttggtttg | 660 |
| gaccacggga tggcaggcac atgtactctt ttggttactg gggagatagt ccattggtgc | 720 |
| ctcctacagg aatctaaaag cggggaagct gatggaggag tcagtcactc tagttatggg | 780 |
| cagtgtccaa agacagtgga caccaaagct gcagtagtgg actgattgat ccactgtgaa | 840 |
| agagcaagta atcagacaaa tatgctgta gagctttgtg ggcccttgca catgtctgcc | 900 |
| tcctctctga cttggctgtt gttctagttt gctttctgtt gctgtgataa ataccatgac | 960 |
| caaaatcaac ttggggagga aagggctta tttaacttac aggttatagt ttaccatgga | 1020 |
| agagggaaac cagggaagga actcaggaca agaacttgaa gcagatacca gatacaacgg | 1080 |
| aggtttgctc ccaggcatac atcagatacc tttatttat ttttattatt gttatttttt | 1140 |
| tatagagagg gtctcacttt gtaaccctgg cctccctgga acttgctatg tagatcaggc | 1200 |
| tggcctcaaa ctcacagaga cctgccttct gggattaaag gcttgaatta ttaggcttgg | 1260 |
| cccaggtacc agtgcagcct acctgcccag ggatggcacc atctgcagtg gggttctacc | 1320 |
| tcccatatca actagcaatc aagaaaatgc tccacaaaca ttccctcagg gcagtctggt | 1380 |
| ctaagcagtt cttcaggcga gggtctgtct gtctatcttc taggtatgcc aggttgacaa | 1440 |
| acaaatgaac cagacggctc ttgattgcaa actgcaaagg gtgtctgcta cctcagggat | 1500 |
| ggtgtgggcc tgaagctctt gcccaactca gtaaagggca gctgtggaca cttgtgtact | 1560 |
| ggacactggc tgagggctg ggatccagtg gaaaccctgg cctttgttag ccctgaagta | 1620 |
| atcaggacag aatggagtga aaagctgcta gctgctgcct cagaaaatga gtgtgacctg | 1680 |
| ggatcacgat ctctccagtt cctgtgtaat tttaaccta gcctctcaag catgttgttt | 1740 |
| gattataata acaagctaga tagaggtagt ggcacacttc agtagctcca gcacttaaga | 1800 |
| gggagaggca ggagtatcaa aagtccaagg tcatccgagg ccagcctggg ctatatgaga | 1860 |
| ttctgccgaa acaaagcaaa acggtgagat ctccaaatgg ctgattcata gatttaaaat | 1920 |
| aaagacatac atttagtgtg cgagtgtgta tactatgtgt gtgtatgtgt acgggtatgt | 1980 |
| gcacgtgccc ttgtatgtgc attacatgat ggaggtcaga ggacaacctg tgggaatcag | 2040 |
| ttctctcttc gtgaatcccg aggatccaac tcagtttgtc aggcttggtg gcaagggcct | 2100 |
| tcacctctga accatagtgc cagccctgag tcatagggtt ttttttatc ctttctgtat | 2160 |
| gggatttatt ccacatacaa cttattcttt attccttta agaaactaag acattcaatt | 2220 |
| gttgacaaga caatgatttt ccaacaactc cctcgtattt ctcatctatc ctgttctgct | 2280 |
| taaattaggc tagatcaact tcccctttcc cccctttctt tgttttgaga cagagtttca | 2340 |
| ctctatagat caggctaaac ttgggctctc aggctccttg tctaagcctc tggagtccag | 2400 |
| agatgacggg tctgccacac cctgcgttta caatcagtgt ttacaatcaa ataaatggaa | 2460 |
| ataaacattt ctatcaaaaa aaaaaaaaaa aaaa | 2494 |

<210> SEQ ID NO 7
<211> LENGTH: 1859
<212> TYPE: DNA
<213> ORGANISM: Mouse

<400> SEQUENCE: 7

| | |
|---|---|
| gctcaaagtg gccaactaca gcaactcagg cagattcaag aagaggttca tgtatcctgt | 60 |
| aggatatggg cttcctgctt ttattgttgc tgcatgctgc aatagctggc cacaagaatt | 120 |

-continued

| | |
|---|---|
| atggaacaca caaccactgc tggctcagcc ttcatcgagg attcatctgg agcttcttgg | 180 |
| ggccagcggc agccattatc ttgataaacc tggtgttcta ctttctaata atatggattt | 240 |
| tgagaagcaa actttcttct ctcaataaag aagtttctac acttcaagac acaaaggtta | 300 |
| tgacatttaa agccattgtc cagttatttg tgttgggatg ttcttggggc attggcttgt | 360 |
| ttattttcat tgaagttggg aagacagtga gactgatcgt tgcctatctg ttcaccatca | 420 |
| tcaatgtcct gcagggtgtt ttgatattta tggtacattg tctgcttaat cgccaggtgc | 480 |
| ggatggaata taagaagtgg tttcatagac tgcggaagga agttgaaagt gaaagcactg | 540 |
| aagtgtctca ttctactact cacacaaaaa tgggtctttc tctgaacctg gaaaatttct | 600 |
| gcccaacagg aaacctccat gatccttctg actccatcct tccaagtact gaagtagcag | 660 |
| gtgtatatct aagcacaccc aggtctcaca tgggtgctga ggatgtgaac tcaggtactc | 720 |
| acgcttactg gagcagaact attagtgatt gaatcagctc cttcccccaa gcctcttaca | 780 |
| gtacatttta acttgtactg tgccatgcac atgaagctat aattgctagt ctggtaaaac | 840 |
| aactgttgca tattccatga tcatttcatt ttatctctac ttgcaaaagt tagctttctt | 900 |
| tttatatcat ttttatttct ctttcttttg tttatatata gcttcagttg agtgggtttc | 960 |
| tagtcttaat gttctagatc actatttcct tttcagttaa cctttattgg tatttagttc | 1020 |
| ctgtgtagtg tataccactg gaatatttt atttctttaa ttttgaggtt aaaatatagt | 1080 |
| tacatcattt ttccttttt tctttcccac aatcctcctg tatactttt ccctggtgtc | 1140 |
| tatttattg tttctacatg catatatatt ttatgcaaaa catatatatg tataaatata | 1200 |
| aatatatatt cttatatgca tgaaaaccat ctacttcatc caaataatgt tccttctatg | 1260 |
| tatgttttca ggacagggac aacaatagct atggtagcat ggcaggggaa agcccacagg | 1320 |
| acctcagcct tatacaaaga atcagaggca actgaggagt gctgagttga aggaattgtc | 1380 |
| ttacccaggg gagggcacat taattggtta tctaatacaa aatgttcagc cccaaaactg | 1440 |
| ttaagataaa agcctatatg catcttagga agtatctacc ttgatacacc tttattggaa | 1500 |
| tatcatccac atgtttattg tgtgttctga agagggtctg ttgaatttct aagggttgat | 1560 |
| cagtttaatt gtgccatttt atattcaggg tgtttggctt tgttgtagtg aataatgcta | 1620 |
| tatttccctg tatgtgtcat ctttgactgt tatttttcc tggcaatact ttattcaaca | 1680 |
| agaacctaga gccttggttt attactttt cttccataga aaaactattt gtcttccagg | 1740 |
| attagatatg atcaatattt cttatatgca tgtatcaaat atcatgatga aatatattac | 1800 |
| tgtgtataat taataactgg caataaagtc caagggaaaa ggaaaaaaaa aaaaaaaa | 1859 |

<210> SEQ ID NO 8
<211> LENGTH: 2305
<212> TYPE: DNA
<213> ORGANISM: Mouse

<400> SEQUENCE: 8

| | |
|---|---|
| gaatctgtgg aagcagttta ttccagtatc acccaggagc agccacacag aggctggtag | 60 |
| gagggctgga tttttgttct cttttttct tttctttaaa tgtaacactt ctttattttt | 120 |
| tcttcttgaa gagtcttgag gatacttaca ttgcagttaa gtagtacagg gtggataaat | 180 |
| tctactttga agaaaacttc tctcctctga caaggttgga cttgtacaca ggccagcatg | 240 |
| aaggagtatg tgatgctact gcttttggcg gtgtgctctg ccaaacccct ctttagccct | 300 |
| tcccacacag cactgaagaa tatgatgttg aaggatatgt aagacacaga tgatgacgat | 360 |
| aacgatgatg acgacaactc tctttttcca acgaaagagc cagtgaaccc ttttttccct | 420 |

-continued

```
ttcgatttgt ttccaacatg tccatttggg tgccaatgtt actctcgagt tgttcactgc        480
tctgatctag gtctgacatc ggttccaaac aacattccat ttgatactcg aatggttgac        540
cttcaaaata ataaaatcaa ggaaattaaa gaaaatgact ttaaaggact cacttcactt        600
tatgctctga ttctgaacaa caacaagcta acaaagattc acccaaaaac ctttctaacc        660
acaaagaaat tgagaaggct atatttatcc cacaaccaac taagtgaaat tccacttaat        720
cttcccaaat cattagcaga actcagaatt catgataata aagttaagaa gatacaaaag        780
gacacgttca agggaatgaa tgctttacat gttttggaaa tgagtgcaaa ccctcttgag        840
aacaacggga tagaaccagg ggcatttgaa ggggtgacag tattccatat caggatcgct        900
gaagcaaaac taacctcaat tccaaaaggc ctaccaccaa ctttgctgga gcttcattta        960
gattttaata aaatttcaac ggtggaactt gaagatctta aacggtacag ggaactgcaa       1020
aggctgggtc ttggaaacaa cagaatcaca gatattgaaa atggaacttt tgctaatata       1080
ccacgtgtga gagagataca cttggaacac aataaactaa aaaaaatccc ttcaggatta       1140
caggagttga ataccctcca gataatcttc cttcattata attcaattgc aaaagtggga       1200
gtgaatgact tctgtccaac agtgccaaag atgaagaaat ctttatacag tgcaataagt       1260
ttattcaaca acccaatgaa gtactgggaa atacaacctg caacatttcg ttgtgttctt       1320
ggcagaatga gtgttcagct tgggaatgtt ggaaaataat tcatgacatc cattaaatat       1380
aaaattcaaa aatgtataca tttggaatac ttgaactgtc ctagtaatgg tagtattata       1440 cataagca aaattctatt ctatatggtc aatgacaaaa aatttcaaca gaattttgcc         1500
taattattga tgctcagaat aaatttctat tgcagtgtcc ttctgcacat gaatgattct       1560
tgcgtaaatc ttttgcttga acattctttt tttcggcaaa aaagatatt tagtatttaa        1620 cccttcatta tcaagtcagt caaacagaat tgtactgtaa acagaatgct tgacttagta       1680
acatttgtgt catatctttg ctgttagaaa aacaaaactg gcaagaacag cattttgaag       1740
agtacatata ttttttagtag tttttttaaaa aaaacttgga cagtactgta atgtttccaa    1800
taatgttgga atacatatag tttgacagaa tcaaaattct caactcataa taaagcttca      1860
agtattcaca gataatattc atcagagttg gtttgggcta taacacatga atatctttt        1920 taaattatta actggctata aaattgtaaa aatataatga ctgctaatat aaaatctata      1980
atgtgcattt tatgatcagt tatataagct ttgaagaaca cagtaactgt taggttacat      2040
agtgttatta cttcaactag gaatatttca ggatatccct ttggaacagt atggacgcca       2100 atcaattta tatcaactta tctcttcaaa tatgcacatt gggtaatgcc tggaaacata       2160
gctaaggtga caaaaactga aaactgaaca aaacttaata gtactttcat gtgttttttt       2220
taaactgata ttcattatga attaagtaaa aagtgacaat aaggaaaaca ttaaatactg       2280
gttttcaata aaaaaaaaaa aaaaa                                             2305
```

```
<210> SEQ ID NO 9
<211> LENGTH: 1930
<212> TYPE: DNA
<213> ORGANISM: Mouse

<400> SEQUENCE: 9
gcggaggcgc gcagggcagc ctgggtccag cccacacccc tcaccaggag gcaccatgtg         60
gggatgttgg ctggggctgc tcttgctgct gctggctggc caggctgccc tggaggcccg        120
gcggagtcgt tggcgcaggg agctggcgcc agggctgcac ctgcggggca tccgggacgc        180
```

-continued

| | |
|---|---|
| cggtggcaga tactgccaag agcaggacat gtgctgtcga ggccgtgctg acgagtgtgc | 240 |
| cctgccctac ctgggagcca cctgttactg tgacctcttc tgcaaccgca ccgtctctga | 300 |
| ctgctgcccc gacttctggg acttctgcct cgggattcca ccccccttcc ctcccgtcca | 360 |
| agggtgcatg catgggggcc ggatctaccc agtcttcgga acctactggg acaactgcaa | 420 |
| tcgatgcacc tgccatgagg gagggcattg ggagtgcgac caggagccgt gtctagtgga | 480 |
| cccagacatg attaaagcca tcaaccgagg caactacggg tggcaggctg ggaaccacag | 540 |
| tgccttctgg ggcatgaccc tggatgaggg cattcgctac cgcctgggca caatccgccc | 600 |
| atcctccact gtcatgaata tgaatgagat ttatacggtg ctgggccaag gggaagtgct | 660 |
| acccactgcc tttgaagctt cagagaagtg gcccaacctg atccacgagc cattggacca | 720 |
| gggcaattgt gcaggttcct gggctttctc cacagcagct gtcgcatctg atcgcgtctc | 780 |
| tatccattct ttgggacaca tgacacccat cctatcaccg caaaacctgc tgtcctgtga | 840 |
| tacccaccac cagcagggct gccgaggtgg gcgtcttgat ggcgcttggt ggttcctgcg | 900 |
| gcgccgcggg gtggtgtctg acaactgtta cccattctcc ggccgtgagc agaacgaggc | 960 |
| cagccccact cctcgttgta tgatgcacag ccgcgccatg gggcggggca agcgccaagc | 1020 |
| cacttcccgc tgccccaatg gtcaggttga ttccaacgac atctaccagg tcacgcctgc | 1080 |
| ctaccgcctg ggctctgatg agaaggagat catgaaggag ctaatggaaa acggccctgt | 1140 |
| tcaagcactc atggaagtac acgaggactt cttcttgtac cagcgtggca tctacagcca | 1200 |
| cacacctgta agcaggggga ggccggagca gtaccgcaga catgggactc actcagtcaa | 1260 |
| gatcactggg tggggagaag agacgctgcc agacggaagg accattaagt actggactgc | 1320 |
| tgccaactcg tggggcccat ggtgggtgtga aggggccac ttccggatcg tgcgtggcac | 1380 |
| caacgagtgc gacatcgaga ccttcgtgct gggcgtctgg ggtcgcgtgg aatggagga | 1440 |
| catgggcac cactgagtct cagccactag gcgaggtggg atccacagcc acagaagagg | 1500 |
| ccttggggc catgcccgat gaagccttgt gtgcacttcg ggaccaggtg ctaatctcta | 1560 |
| cagactcaga tccgcgcgtg cgcgctaagg cagaatccca cctaggagac aaagatgcac | 1620 |
| caggctggcg gaagccccca gatatcacag ccggaactgg aagggccct gtttggaaac | 1680 |
| tgcagggagt atagacagat tccaggtccc tggtcagcca ggccaagacc acaggagcta | 1740 |
| agacacccca acctcatcac cctcctaccc accctctctc tcatcttctt tttgatgaat | 1800 |
| tctgtccatc tccctagcct ccattttggt tgtaccttc cattctcagt actgcttcct | 1860 |
| tattctttaa agatatttat ttttcttttc attaaaataa aaccaaagta ttgataaaaa | 1920 |
| aaaaaaaaaa | 1930 |

<210> SEQ ID NO 10
<211> LENGTH: 2617
<212> TYPE: DNA
<213> ORGANISM: Mouse

<400> SEQUENCE: 10

| | |
|---|---|
| ggcggcggga agatgcggtt gcggctccta gcgctggcgg cggccgtgct gctgggtccg | 60 |
| gcccccggaag tctgtggtgc tctcaatgtc acggtgtccc caggacctgt ggtggactac | 120 |
| ttggaagggg aaaatgccac cctcctctgc cacgtctccc agaagagacg gaaggacagc | 180 |
| tgctggccgt gcgctggttc ttcgcccctg acggctccca ggaggccttg atggtgaaga | 240 |
| tgacgaagct ccggataatt cagtactatg gaacttcag ccggactgcc aaccagcaga | 300 |
| ggctacgcct gctcgaggag cgtcgagggg tgctgtacag gctgtctgtc ctgacgctcc | 360 |

```
ggcccacaga tcaagggcag tatgtctgca aagtgcaaga atcagcaag  caccgcaaca    420
agtggacagc ctggtccaat ggctcctcgg cgacggaaat gagagtgatc tccctcaaag    480
ctggcgaaga ttcatcattt gagaaaaaga aggtgacttg ggcattttt  gaagatctct    540
atgtgtacgc tgtccttgtg tgctgcgtgg ggatcctcag tgttctgctc ttcaccctgg    600
tcattgcctg cagtctgtgt tcacaagag  gaaatcaaga gtgagacatt atttggtgaa    660
gtgccctcag aacagctcag gggagactgt caccagtgtg accagcttgg ccccactgca    720
gccacagaag ggtaagaggc agaagaagaa ggtagatgtt ccacctgcag tccctgccaa    780
agcgccgata gccaccactt tccacaaacc aaagctgctg aaaccacaga ggaaagtcgc    840
cctgcccaag atcaccgagg aaaacttgac ctatgccgag ctggagctga tcaaaccaca    900
cagggctgcc aaaggcgtcc ccaccagcac cgtgtatgca cagatcctct tcgaggagaa    960
ccagctgtag cgatacctcc tctctggctg tcatgtgttc tcccagttgt ttatgacact   1020
cagaaacaaa ctccctagtt ttgtattttc accgtgcct  tcagtgtgat ggggagcccc   1080
ttcccacagc gttctgatgt cttctaagag gtacacactt cccagaagag aagggaccag   1140
ctcttggcca tgcctcccaa gataagaggc ccctggcctg attctgagca caaggactct   1200
gcttctgaga gcattgctga gccaaccgta ccaacttctc ctcttcttaa gccttaaagt   1260
tttgagggaa aaatcaaatc ttaattttaa tcagccccc  ttgttctgta taacaagcat   1320
ccagtttata gccacaggaa atgctgtaaa ggtcacagag agaaatggga tatatggact   1380
gacaagttct ctaaggctct gggacaccca ggacagagca aacccctgga ggtggtggca   1440
ggagccactt atgatgacat ccattgcttt taatagatgc tctgaaactg ccatgtgag    1500
ggcagagatg ctgatggttg aaagccggag atctggctca gaaaattctg gtcttatgtc   1560
tttagagcca tacttcacca gggctgtaga tctacaagaa cacccttgta agtgttgt    1620
cccctttag cagaatggac ctagagagac atattgttct ctcttttcca aagacttgag   1680
tatggctcca gtgggtacat cgggtaagtg agcaaagcat gcaagctcag tcaactccat   1740
tcaagataga gtggagcctt tcaccattcc ctcagcagag aaatgaaagc acaaggcatg   1800
ccgggaaact atgtccagga ggactcaacc cttggcaagt gctttgaccg tctcaatctt   1860
ggatgagaac catgattgcc ttgggtggat gtcagggac  catgggacat aagtccgtgg   1920
ggaagtgact ctgtggaccc taaacaatgta caaaaatgtc agacttaatg gaagtaagag   1980
agtcaccttg atttccgcag tgctattgat gcttcttgat gtatactctg gtggccactt   2040
actgcacttt ataaacattg tctggctttg taatttaca  atgtatatat gataaattat   2100
ctattttaaa cacagctagg gtgtgcattg tgccctctgt ctcactgtgg gacttgagtt   2160
ttttattacc ttaacttgga tcacagctac acaagttgtg ggaatggggg aacccactga   2220
acattgcctt ttaatgggga atagaagcct cacagcatcc ctgccgagct tgtctctctg   2280
acttttcaa  agggaaaccg cagcagcacc ctcagagcag ggacaatgag cagtttgtac   2340
ctggtgcttg tttgaagtaa catatttgg  ggttcttgat cagaaaatgt gtctagtcgc   2400
tcttccttta ccacatagac cactaaccgt gaattgacat ttctgaagct aagtgaggag   2460
aagcatccat catctggaaa gtgcaaaggg ttcttcttgc gacaaggcat caataggagc   2520
ggtgatgtaa tcactgagta gttccccaaa tggacagctg cttccagtgt tccatgcaat   2580
taaagcaagc atgacctcaa aaaaagaaaa aaaaaaa                             2617
```

<210> SEQ ID NO 11

-continued

```
<211> LENGTH: 1480
<212> TYPE: DNA
<213> ORGANISM: Mouse

<400> SEQUENCE: 11
gggctcccag gtgatcggtg tgtgtcagcc tcactccagg gcctccaggg aaccatggac      60
ttttggcttt ggttacttta cttcctgcca gtgtctgggg ccctgagagt cctcccagaa     120
gtacagctga atgtagagtg gggtggatcc attatcatcg aatgcccact ccctcaacta     180
cacgtaagga tgtatctgtg tcggcagatg gccaaacctg gatatgctc cactgtggtg      240 tccaacacct ttgtcaagaa ggaatatgaa aggcgagtca ccctgacgcc atgcttggat     300
aagaagctat tcctagtgga gatgacacag ctgacggaaa atgacgatgg aatctatgcc     360
tgtggtgtgg gcatgaagac agacaaaggc aagacccaga aaatcaccct gaatgtccat     420
aatgaatacc agaaccatt ctgggaagat gaatggacct ctgagcggcc aagatggttg      480
cacagatttc tgcagcacca gatgccctgg ctccacggga gtgaacatcc cagctcttct     540
ggagtcatag ccaaagttac cacgccagct tcaaagactg aggcccctcc ggttcaccag     600
ccctccagca tcacttcagt aacccaacat cccagagttt acagagcatt ttctgtgtca     660
gctaccaagt ccccagcgct cctgccagca accacagcct caaagacttc cactcagcaa     720
gcaatcaggc ccctagaggc cagctacagc caccacacca gacttcatga gcaaaggaca     780
cgccaccatg gcccacacta tgggagagaa gaccgagggc ttcacatccc catcccagaa     840
tttcacatcc tgattccgac cttcctgggc tttctcttgc tggttctttt gggactggtg     900
gtaaaaagag ccattcaaag gaggagagcc tcctccagac gtgcgggccg actggcgatg     960
aggaggcgag gccgggggc ttcccgcccg ttccccacac agcgccggga tgccccgcag    1020
aggccgcgct cgcagaacaa cgtctacagc gcctgccccc ggcgcgcacg gggaccagac    1080
agcttgggtc cagcggaggc tccgctcctc aacgccccag cctcagcgtc ccccgcttct    1140
ccgcaggtac ttgaagctcc ttggccccac accccatctc tgaagatgag ctgtgaatac    1200
gtgagcttgg gctaccagcc tgctgtcaac ctggaagacc ctgattcaga tgattacatc    1260
aatattcctg acccatctca tctccctagc tatgccccag ggcccagatc ttcatgccaa    1320
tgagttctgc ctgtttgctg atgtctagca cgttttcctt ataggatccc tgtcatggcg    1380
tatgtcctat accctaagtc gactctcacc tgactatctg aatgccttga gaatgatcaa    1440
ttacaggcta attttcacc ccaaaaaaaa aaaaaaaaa                              1480

<210> SEQ ID NO 12
<211> LENGTH: 802
<212> TYPE: DNA
<213> ORGANISM: Mouse

<400> SEQUENCE: 12
gctgagccag gatgaaggct ctcagggctg tcctcctgat cttgctacta agtggacagc      60
cagggagtgg ctgggcacaa gaagatggt atgcggaccc ggagccagag aactacaact      120
acgatgatga cgatgatgaa gaggaagagg aggagaccaa catgatccct ggaagcaggg     180
acagagcacc tctacaatgc tacttctgtc aagtgcttca cagcggggag agctgcaatc     240
agacacagag ctgctccagc agcaaaccct tctgcatcac gctcgtctcc cacagcggaa     300
ccgacaaagg ttacctgact acctactcca tgtggtgtac tgatacctgc agcccatca     360 tcaagacagt ggaggcacc cagatgactc agacctgttg ccagtccaca ctgtgcaata     420
ttccaccctg gcagaacccc caagtccaga accctctggg tggccgggca gacagccccc     480
```

-continued

```
tggaaagtgg gactagacat cctcaggtg gcaagtttag ccaccccag gttgtcaagg      540 ctgctcatcc tcagagcgat ggggctaact tgcctaagag tggcaaggct aaccagcccc    600
agggaagtgg ggcaggatac ccttcaggct ggaccaaatt tggtaatata gccctcctgc    660
tcagcttctt cacttgtctg tgggcgtcag gggcctgaag acccgttctc ctccaaccag    720
gacgccctgg cctctccttc ctgacaacca gcttcagaga ataaacttga atgtcgtttg    780
ccatctaaaa aaaaaaaaaa aa                                             802
```

<210> SEQ ID NO 13
<211> LENGTH: 2112
<212> TYPE: DNA
<213> ORGANISM: Mouse

<400> SEQUENCE: 13

```
gggtgctcag acggtgaaaa tcagagatca ggccaccttt ctgtgagcct tcagctgagt     60
ctaaaggtgt tattgatcag aatggcttca ggatggtttt acctgtcctg catggtgctg    120
ggatcgctgg gatcgatgtg catcctcttc actgcctact ggatgcagta ctggcgcggt    180
ggctttgcct gggatggcac ggtgctcatg tttaactggc acccagtgct catggttgcc    240
ggcatggtgt tgctctatgg agctgcctca ctggtgtacc gctgccttc atcgtgggtg    300 gggcccaggc tgccctggaa agttctccat gcagcactgc acctgctggc cttcacctgc    360
actgtggtgg ggctgattgc cgtctttcgg tttcacaacc actcgagaat cgcacacctc    420
tactccctgc acagctggct gggtatcacc actgtagtcc tcttcgcctg ccagtggttc    480
ctgggctttg ctgtcttcct cctgcccgg gcatcccagt ggctgcgaag cctcctgaaa    540
cctctgcatg tattctttgg agcctgcatc ctttccctgt ccatcacatc tgttatttcc    600
ggcatcaatg agaagctttt cttgttttg aaaaatgcca ccaagcccta ctccagcctg    660
cctggtgagg ctgtctttgc caacagcaca gggctcttgg tggtggcttt tggcttgctg    720
gttctctatg ttcttctggc ttcatcatg aagcgtccag atccaggagc tctgactgat    780
agacagcccc tgttgcatga cagggaatga agcgggcagg ggctcctggg aacggtcagc    840
gatgcggtct ctgctccctc agaagttctg ctgtactggg gctcctggct ggtttcagca    900
acagacttct cttgggccag agacccaacc ttgctactcc agttgcaggc tctcgctgtc    960
cagccactag ctgttcctct gcttttcttg tggctttggc ttattgccgt ttttttctgg   1020
tcctccattg gcacaaagac cttcttgcct tggtcacaca tgtctcttct gctggtctgc   1080
agatttgggc tgcttttcctt accactccta gggatgtggg agaagccaaa gctgggttc    1140 aaatgcagtc tacacgtgta aaatacaaag tctgctctct gtgggagcat ttgtcttagt   1200
taggtatgct tcccctctg ctctgtcctg gatgtgtatt tgggtgggca gttgcattga    1260
ggggtcattc atgggacagt ggcagccgga gaagcctctg ctgtaaagtc aggtgcccag   1320
tactctgctc ttttcacttt gatgtgctgt attgtgtgga ttgtgaccttg tgattcccc    1380 ctcttctagc tgctgctcca gctgcttcct ggatcccgcc ctttccctgt gacttacatg   1440
cctgttcccc tcaggtagca tgacgagccg ttaaacagtt ctcccaagaa cacatgtcct   1500
gtccctagag tccctcccag tgatgagtct gaggtttctt tggccttcct ttctgtccct   1560
ttgtgggtat gggctttcct gcctcctcta gttatgctct cccctgacag ggccccagcc   1620
cactatgaaa ttgaaaccag cattatgaag caatttgctg ggagccattc actgctgctg   1680
ccttcagaga tgttccttag tgagtagtgg gtgcttctgt tccccaaaag gtcactcagc   1740
```

-continued

| | |
|---|---|
| tacccctctat gctataccag aatgtgagct tgctcttct gaatagaaac tgggtagaga | 1800 |
| gggaggagtc ttgccccact cctttgtgtt agccctgcca ggtccctcaa caggcaggca | 1860 |
| ggcaggcaag caggcagaca ggcaggcaga gttgggttcc tgaactctct gcagacagtg | 1920 |
| gccaggctgc cagacgttgg gaggagggct ggcatggatt tgctgactaa atggaagcct | 1980 |
| gaacacatag cgatgactct tggcacccac atgaacatct tcctggttca ctcatgagtg | 2040 |
| ggtattttac ttcatgaatc ttatttttat taaatatgtt tttaaacatc agaaaaaaaa | 2100 |
| aaaaaaaaaa aa | 2112 |

<210> SEQ ID NO 14
<211> LENGTH: 915
<212> TYPE: DNA
<213> ORGANISM: Mouse

<400> SEQUENCE: 14

| | |
|---|---|
| ggaagtaagt tcagaggcca tgagactgcc tctgccactg ttgctactgt tcgggtgcag | 60 |
| ggctatcctg gggagcgccg gggatagggt ttccctctcg gcttcggctc ccacactgga | 120 |
| tgatgaagag aagtactcgg ctcatatgcc ggctcacctg cgctgcgatg cctgccgggc | 180 |
| tgtggccttc cagatggggc aacgtctggc gaaagcagag gctaaatctc acactccaga | 240 |
| cgccagtgga ttgcaggagc tgagtgaatc cacgtacaca gatgtcctgg accagacctg | 300 |
| ctctcagaac tggcagtcct atggagttca tgaagtgaac cagatgaagc gtctcacggg | 360 |
| cccaggactt agcaaggggc cagagccaag aatcagcgtg atgatttctg ggggtccctg | 420 |
| gcccaatagg ctctccaaga cgtgtttcca ctacctgggt gagtttggag aggaccagat | 480 |
| ctatgaagcc taccgccaag gccaagcgaa tctggaggcg ctgctctgtg ggggcaccca | 540 |
| tgggccctgc tcacaggaga tcctggccca gagagaagag ctttagtcca acctgctgca | 600 |
| cttctggatc ttctctaatt ttattattat taatggctga ttagaggcag gctctcatca | 660 |
| tgtaggccag gctggcctta aacttgtcat cctgctcagc ctcgaaagtg ctgcatttaa | 720 |
| gtcctgagcc ttttgtgct tgaccctcct atataatttt tcaactgtg gtggtgggga | 780 |
| ggggacaggg aagcctgact ctagctgtca atcttctccc tccacctctc gatggggtac | 840 |
| tgggactgag gctgccttc tactttcaaa taaagctttg aaagacaaaa aaaaaaaaa | 900 |
| aaaaaaaaaa aaaaa | 915 |

<210> SEQ ID NO 15
<211> LENGTH: 1308
<212> TYPE: DNA
<213> ORGANISM: Mouse

<400> SEQUENCE: 15

| | |
|---|---|
| gtgagagctc agctggaagt gactgggtga caaggcgcac aggctcagcc gtggaagctc | 60 |
| catcatgatt ccacaagtag tgaccagtga gactgtcaca gtgatttcac caatggaat | 120 |
| cagctttccc caaacagaca aaccccagcc ttcccaccag agccaagaca gactgaagaa | 180 |
| acatctaaag gctgagatca aagtgatggc ggcaatccag atcatgtgtg ctgtgatggt | 240 |
| gttgagtctg ggaatcattt tggcatctgt tccctccaat ctacactta cctcagtgtt | 300 |
| ttccatcctg ttagaatctg gctacccatt tgtaggagct tgtttttg ccatctctgg | 360 |
| aattctgtct attgtcacag agaaaaagat gactaagcct ttggttcaca gcagcctagc | 420 |
| cctgagcatc ctgagtgtcc tctctgctct tacaggcatc gctattctct ctgtcagttt | 480 |
| ggctgctttta gagcctgcct tgcagcaatg taagctggct ttcacacaac tagacacaac | 540 |

```
ccaagacgct tatcatttct ttagccctga gccattaaac agctgcttcg tggccaaagc    600
tgctctgact ggagtctttt cactgatgct aatcagcagt gtgttggagc ttggcctggc    660
tgtcctcact gccacactgt ggtggaaaca gagctcctct gctttctctg ggaatgtgat    720
tttcctgtct cagaactcaa agaataaatc cagtgtatct tcagagtcac tttgtaaccc    780
tacatatgaa aacatattga cttcataaga attaagtaga ggttatatag cagaaaaatc    840
tgtctttaac atgatttaga aaagccattt actgtgtgac aacaatgctt aatatcttaa    900
tatcttaatg tgtgtattgg ttaatcagca accatgaaaa acatactaac tggctgggtt    960
cagtagcacg ctcttgattt ggcgtcagtc aaaacacaga cctgtaaatt ccaatttatg   1020
tagtggtcaa agagccccaa ttattttctc aaaaaactgg aagaatgttt cataggatca   1080
tggtggagcc aatgggcaac agttcttctt atccttgtca cttggctgca ggaggtactg   1140
actagggcct gagatcatat tctgtgtgcg tggcatggac ttcatggcat ctattttatt   1200
cataagcaca tgaaaacaag tcatctctta tgaagtctca aagagcataa aaaagttagc   1260
ctccaaataa agtctttatg taatcccaaa aaaaaaaaaa aaaaaaaa                1308

<210> SEQ ID NO 16
<211> LENGTH: 1288
<212> TYPE: DNA
<213> ORGANISM: Mouse

<400> SEQUENCE: 16
gctccagctc ctccatcctg tagtttacag ggtgtaccct atgtcgggac caatgtgacc     60
ctgaactgca gtccccaag gagtaaacct actgctcagt accagtggga gaggctggcc    120
ccatcctccc aggtcttctt tggaccagcc ttagatgctg ttcgtggatc tttaaagctc    180
actaaccttt ccattgccat gtctggagtc tatgtctgca aggctcaaaa cagagtgggc    240
tttgccaagt gcaacgtgac cttggacgtg atgacaggtc agtaaggggg tccaaggctg    300
cagtggtcgc tggagcagtt gtgggcactt ttgttgggtt ggtgctgata gctgggctgg    360
tcctgttgta ccagcgccgg agcaagacct tggaagagct ggccaatgat atcaaggaag    420
atgccattgc tccccggacc ttgccttgga ccaaaggctc agacacaatc tccaagaatg    480
ggacactttc ttcggtcacc tcagcacgag ctctgcggcc acccaaggct gctcctccaa    540
gacctggcac atttactccc acacccagtg tctctagcca ggccctgtcc tcaccaagac    600
tgcccagggt agatgaaccc ccacctcagg cagtgtccct gaccccaggt gggtttctt    660 cttctgctct gagccgcatg ggtgctgtgc ctgtgatggt gcctgcacag agtcaggctg    720
ggtctcttgt gtgatagccc aggcactcat tagctacatc tggtatctga cctttctgta    780
aaggtctcct tgtggcacag aggactcaat cttgggagga tgcccacatt ctagacctcc    840
agtcctttgc tcctacctcc ttctattgtt ggaatactgg gcctcagtaa gactaaaatc    900
tgggtcaaag gacaaaagga ggaaatggac ctgaggtagg gggttgggag tgaggaggct    960
tcacttcctc cctgcttctc cctgaagcca atgaatgct cgggaagatc ggctaccctc   1020
caagggctct ggaggagact gccagtcagt gatgcccctg gctctgtgat ctgtacaaca   1080
cccttatcta atgctgtcct ttgccgttcg ctccatctcc ctgtattaat ataacctgtc   1140
ctgctggctt ggctgggttt tgttgtagca gggggatagg aaagacattt taaatctga   1200 cttgaaattg atgttttgtt ttatttttg caaattccaa taaagataca tcgcatttgc   1260
atggccaaaa aaaaaaaaaa aaaaaaaa                                      1288
```

<210> SEQ ID NO 17
<211> LENGTH: 999
<212> TYPE: DNA
<213> ORGANISM: Mouse

<400> SEQUENCE: 17

| | | | | | |
|---|---|---|---|---|---|
| gccagctttt | tcctccgcag | ccatgtcctg | gtctccgatc | ctaccatttt | tgtcccttct | 60 |
| gcttctgctg | ttcccactcg | aggttcccag | agcagccact | gcgtccctt | cgcaagcatc | 120 |
| ctccgaaggc | acaaccacct | gcaaggtcca | cgatgtgtgc | ctcttgggc | cacgcccatt | 180 |
| gccccttca | ccacctgtca | gagtcagcct | gtattatgag | tccctgtgtg | gagcttgtcg | 240 |
| ctacttcctc | gtccgggatt | tgttcccaac | ctggctgatg | gtgatggaaa | tcatgaacat | 300 |
| caccctggtg | ccctacggga | atgcacagga | gagaaatgtc | agcggtacgt | gggagttcac | 360 |
| gtgccagcac | ggggagctgg | agtgtagact | aacatggtg | gaggcctgtc | tgctggataa | 420 |
| gctggaaaag | gaggcagcgt | tcctaaccat | cgtctgtatg | gaggagatgg | atgatatgga | 480 |
| gaagaaactg | ggaccgtgcc | tgcaggtgta | tgctcctgag | gtgtcaccag | agagtatcat | 540 |
| ggagtgcgcc | acaggaaaac | ggggcacaca | gctcatgcat | gagaatgccc | agctcacaga | 600 |
| tgccctacac | ccaccccacg | agtatgtgcc | ctgggtgctg | gtcaatgaga | accttgaa | 660 |
| ggaccccagc | gagctcctga | gcatagtctg | tcagctggac | cagggaacgg | agaagccaga | 720 |
| catctgctcc | tccattgccg | actccccag | gaaggtctgc | tataagtaaa | ggcataacct | 780 |
| caaactcgtc | ccagaaaact | gcccagcttc | ttcaaattgc | caacctgcaa | gagctgctgc | 840 |
| ctcgctatga | aaaccttgca | catgtcccac | aaagcccaga | ctccagactt | ctcagagaca | 900 |
| aggatcttgc | cttattttca | aatggtgcta | aatttaaatt | catagaataa | atcatctata | 960 |
| ctcctgtgat | tccttttcc | taaaaaaaa | aaaaaaaa | | | 999 |

<210> SEQ ID NO 18
<211> LENGTH: 2123
<212> TYPE: DNA
<213> ORGANISM: Mouse

<400> SEQUENCE: 18

| | | | | | |
|---|---|---|---|---|---|
| gctgtcccgt | gtcctgctgt | ggaaactgct | gcttcttcag | agctctgcag | tcctgtcctc | 60 |
| agggccttca | gggaccgcag | cagccagcaa | ctctctggtg | tctgagtctg | tggtgagctt | 120 |
| ggcagccgga | acccaggctg | tgctacgctg | ccagagcccc | cgcatggtgt | ggacccaaga | 180 |
| ccggctgcat | gatcgccagc | gcgtggtcca | ctgggacctc | agcggggacc | cgggcagcca | 240 |
| acggcgccga | cttgtggata | tgtattcggc | gggtgaacag | cgcgtgtacg | agccgcgcga | 300 |
| tcgcgaccgc | ctcctgctgt | cgccttctgc | tttccacgac | ggcaacttct | cgctgctcat | 360 |
| tcgcgctgtg | gagagaggcg | atgaaggggt | gtacacctgc | aacctgcacc | atcactactg | 420 |
| ccacctcgat | gagagcctgg | ctgtgcgcct | cgaggttaca | gacgatcccc | tattaagtcg | 480 |
| cgcatactgg | gacggtgaga | aggaagtgtt | ggtggtggcc | catggcgcgc | ggcactgat | 540 |
| gacctgcatc | aaccgtgcgc | acgtgtggac | tgaccgccat | ttagaggagg | cgcagcaggt | 600 |
| ggtccattgg | gaccgacagc | tacctggagt | gtcacacgac | cgcgccgacc | gcctgcttga | 660 |
| cctgtatgca | tctggcgagc | gccgcgccta | tgggccgccc | ttcctgcgtg | atcgcgtgtc | 720 |
| agtgaacacc | aacgcttttg | cacgcggtga | cttctcccta | cgcatcgatg | agctggagcg | 780 |
| agctgatgag | ggcatctatt | cctgccacct | gcaccatcac | tactgtggcc | tccacgagcg | 840 |
| ccgagtcttc | cacctacagg | tcacagagcc | tgcctttgag | ccaccagctc | gtgcttctcc | 900 |

-continued

```
tggcaatggg tctggtcaca gcagtgctcc tagcccagat cccaccctga cccgaggcca      960
cagcatcatc aatgtcattg tcccagagga ccacacacat ttcttccagc aactgggcta     1020
cgtgttggcc acgctgctgc tcttcatctt gctgctcatc actgtagtcc tggctacacg     1080
acatcgtcac agcggaggat gcaagacgtc ggacaaaaaa gctgggaagt caaaggggaa     1140
ggatgtgaac atggtggagt ttgctgtagc cacaagggat caggctccat ataggactga     1200
ggacatccag ctagattaca aaacaaacat cctgaaggag agggctgagc tggcccatag     1260
tcctctgcct gccaaggatg tggatctgga taaagagttc aggaaggagt actgcaaata     1320
aatggaccct gagcttctgg ctgggccagc agctctgtat caaaggacat ctccctgacc     1380
ctcctgcggt attcctggct cttctcagcg gctggtccga cttacctaga aacttggcct     1440
aaacttggca gagcagctgc ctgtactttg cccttcctag aatcgccacc cctcatcttg     1500
gtgagcaact gtgggttccc tagagactct ggtatagtac gattgctgcc cttcagtcac     1560
ctgtgcccac tgatggtcgg accccaact taaacacaac aaagatccct tgttaatatc      1620
caccaaatgc aaagtccctc gtggcctctt actgctaggg tcaggaagac acttaaaaat     1680
tccaggtaaa actccctagc caccagttaa acacattagc cattgtcctg ggggggggg      1740
ggtcttcctg agctgcatcg tgcctgtgtc ctgctcagag ccctgctgtt ataggttgtg     1800
actcatgggc ccgccttgct gctttgggca acttgaggct agcccagggc cctttctctg     1860
cttctgattc ctttctgccc aatgcctccc aagagctaca ccagcagttt ctgggtaccg     1920
tatgacccct ggccttgaca tccctcccta ggctggagtc tggggttggg gccccatttg     1980
tcctctgttt tggctgaaga tggggtgaag atttggctga gtggcctatg ctgtcacatc     2040
aaacagctat catttactcc tacttggaaa gttgtcatgt gacaataaaa gatacatttg     2100
acttttaaaa aaaaaaaaa aaa                                              2123
```

<210> SEQ ID NO 19
<211> LENGTH: 1391
<212> TYPE: DNA
<213> ORGANISM: Mouse

<400> SEQUENCE: 19

```
gctggcaggc tgctgtgcag tccacgagga aggcttcggt cgacaggaca ggcgtgcaga       60
cttcaggagg gaccctgggc agcagacatt ccctggaagg gcaggttgca ttgcatggtt      120
ggctcatgga ggcagcagag gtggcctcag ccaggcctgg gcagcatcag ccccggcag       180
cagcaagacg ctggctgttc cacctgccca caagaacagc caccaccagt acccagggga     240
tgactagcgg ccgaccaca ggccacaaaa agaagaaggc tacccacctt acagatgcag      300
accatgtggg gctccggaga actgcttgta gcatggtttc tagtgttggc agcagatggt     360
actactgagc atgtctacag acccagccgt agagtgtgta ctgtggggat ttccggaggt     420
tccatctcgg agacctttgt gcagcgtgta taccagcctt acctcaccac ttgcgacgga     480
cacagagcct gcagcaccta ccgaaccatc taccggactg cctatcgccg tagccctggg     540
gtgactcccg caaggcctcg ctatgcttgc tgccctggtt ggaagaggac cagtgggctc     600
cctgggggctt gtggagcagc aatatgccag cctccatgtg ggaatggagg gagttgcatc     660
cgcccaggac actgccgctg ccctgtggga tggcaggag atacttgcca gacagatgtt     720
gatgaatgca gtacaggaga ggccagttgt cccagcgct gtgtcaatac tgtgggaagt     780
tactggtgcc agggatggga gggacaaagc ccatctgcag atgggacgcg ctgcctgtct     840
```

-continued

```
aaggaggggc cctccccggt ggccccaaac cccacagcag gagtggacag catggcgaga      900
gaggaggtgt acaggctgca ggctcggggtt gatgtgctag aacagaaact gcagttggtg     960
ctggccccac tgcacagcct ggcctctcgg tccacagagc atgggctaca agatcctggc     1020
agcctgctgg cccattcctt ccagcagctg gaccgaattg attcactgag tgagcaggtg     1080
tccttcttgg aggaacatct ggggtcctgc tcctgcaaaa aagatctgtg ataacctctc     1140
accacccagg ctggatagag cagtcatccc tagatccctt gtagccagag ttcaggcgct     1200
gtctggtggt gcctatgagc agaaggccct gcctcattgt ccctctttct taggaggttc     1260
ctaggacttg ggcatgggga gtggggtctt gtgtgactct tcagtggggc tccctgtcta     1320
agtggtaagg tggggattgt ctccatcttt gtcataataa agctgagact tgaaaaaaaa     1380
aaaaaaaaaa a                                                          1391
```

<210> SEQ ID NO 20
<211> LENGTH: 1864
<212> TYPE: DNA
<213> ORGANISM: Mouse

<400> SEQUENCE: 20

```
ggcaccgcgc gggcggctat ggagcgagcc tgaggcccgc caggatatga attggctccc      60
tctgaccgcc atttcagtgc ttgtaagtgt gaggtcagca actgcagcct acagattgat     120
aactgtcgaa cccctggaat tgtggaggca ctgcagtgaa gaaatatgta atcatggaat     180
ctccttgcta atcgtcacca cctgttccct gtgataagcc agccaggacg tgggctgagg     240
agaaggaaaa gaggccacca tgaagctgaa gcagcgagtt gtgctgttag caatactcct     300
cgtcattttt atcttcacca aagttttcct gatagacaat ttagatacat cagctgccaa     360
ccgagaggac cagagggctt ttcaccgaat gatgactggc ttgcgggtgg agctggtgcc     420
caagttggac catacccctgc agtctccttg ggagattgca gcccagtggg tggtgccccg     480
ggaagtgtat cctgaagaga caccagagct gggagcaatc atgcatgcca tggccactaa     540
gaaaatcatt aaagctgacg tgggctataa agggacacag ctaaaagctt tactgattct     600
tgaaggagga cagaaagttg tctttaagcc taagcggtac agcagagact atgtggtaga     660
aggggagcca tacgctggtt atgacagaca caatgcagag gtggcggcct tccatttgga     720
caggattctg ggtttccgcc gagctcccctt ggtggtgggc agatatgtta atctgcgaac     780
agaagttaag cctgttgcca cggagcagct gctgagcacc ttcctaactg tagggaacaa     840
tacttgtttc tatgggaagt gctactactg ccgagaaaca gagccagcat gtgctgacgg     900
tgacatgatg gagggctctg tcacacttttg gcttccagat gtgtggcctc tgcagaaaca     960
tcgacatccc tggggcagga cctaccgaga aggcaaactg gccaggtggg aatatgatga    1020
gagctactgc gatgctgtga agaaaacatc ccctatgac tcaggcccgc gtctcctgga    1080
catcattgac acggctgtct ttgattactt gattggcaat gctgatcgcc atcactacga    1140
gagctttcaa gatgatgaag cgcgagcat gcttattctt cttgataatg ccaaaagctt    1200
tggaaacccc tcgctggatg agagaagcat tcttgcccct ctctatcagt gttgcatcat    1260
tcgggtttca acctgaata gactgaatta tctaaagaat ggagtactaa agtctgcctt    1320
aaaatctgcc atgcccacg accccatctc ccctgtgctc tccgatccac acttggacac    1380
tgtggaccag cggcttctga atgtcttggc caccatcaag cagtgtactg accagttttgg    1440 gacggatact gtgctggtgg aagacaggat gccactctcc cacttgtaat tctcaatgcg    1500
aaacaagtgg aactgatttt acaaagatag agaaacagca caatcaattc cgaatggcat    1560
```

-continued

| | |
|---|---|
| gcgatggtct gcaggtggcc acagtgggtg ctggtggcag aagacggtgg cggccctggg | 1620 |
| agtgctcggt gttttctgca gtgcaagcta cggaccacag ttcagctgcc tcacctctca | 1680 |
| ggctgccagc agcagctctg ctcagtcttt attcccacac cagagggcga gcaggtgtga | 1740 |
| cataggctaa ggaagtgttt ccagagtgtg cgtctcgggt gacccttgct gtcttttctc | 1800 |
| tacacccatg gattctctga aaacactttg cagttccttg tgtcttaaaa aaaaaaaaaa | 1860 |
| aaaa | 1864 |

<210> SEQ ID NO 21
<211> LENGTH: 2324
<212> TYPE: DNA
<213> ORGANISM: Mouse

<400> SEQUENCE: 21

| | |
|---|---|
| gggtctgtac tccccgctcc tcgccacaca cacaccgaga ggatgaggct caccgtgggt | 60 |
| gccctgctgg cctgcgccgc cctggggctg tgtctggctg tccccgacaa aacggtcaaa | 120 |
| tggtgcgcag tgtcagagca cgagaatacc aaatgcatca gcttccgtga ccacatgaag | 180 |
| accgtccttc cgcctgatgg cccccggctt gcctgtgtga agaaaacctc ctatccggat | 240 |
| tgcatcaagg ccatttctgc aagtgaagcc gatgctatga ccttggatgg gggttggggt | 300 |
| tacgatgccg gcctgactcc gaacaacctg aagcccgtgg cggcggagtt ttatggatca | 360 |
| gtggaacatc cacagaccta ctactacgct gtggctgtgg taagaagggg aacagacttc | 420 |
| cagctgaacc agctcgaagg caagaagtcc tgccacacag gcctgggaag gtctgcaggc | 480 |
| tgggtcatcc ccattggctt gctcttctgt aagctgtcgg agcccgcag tcctcttgag | 540 |
| aaagctgtgt ccagtttctt ctcgggcagt tgtgtcccct gtgcagatcc agtggccttc | 600 |
| cccaaactgt gtcaactgtg cccaggctgt ggctgctcct ccactcaacc gttctttggc | 660 |
| tacgtaggcg cattcaagtg tctgaaagat ggcggtgggg atgtggcctt tgtcaagcac | 720 |
| acaaccatat ttgaggtctt gccggagaag gctgacaggg accaatatga actgctctgc | 780 |
| cttgacaata cccgcaagcc agtggatcag tatgaggatt gctacctggc tcggatccct | 840 |
| tctcatgctg ttgtggctcg aaaaaacaat ggcaaggaag acttgatctg ggagattctc | 900 |
| aaagtggcac aggaacactt tggcaaaggc aaatcaaaag acttccaact gttcagctct | 960 |
| cctcttggga agacctgct gttaaagat tctgcctttg ggctgttaag ggtcccccca | 1020 |
| aggatggact acaggctgta ccttggccat aactatgtca ctgccattcg gaatcagcag | 1080 |
| gaaggcgtgt gcccggaggg ctcgatcgac aactcgccag tgaagtggtg tgcactgagt | 1140 |
| cacctggaga gaaccaagtg tgacgagtgg agcatcatca gtgagggaaa gatagagtgt | 1200 |
| gagtcagcag agaccactga ggactgcatt gaaaagattg tgaacggaga agcggacgcc | 1260 |
| atgactttgg atgaggaca tgcctacatt gcaggccagt gtggtctagt gcctgtcatg | 1320 |
| gcagagtact acgagagctc taattgtgcc atcccatcac aacaaggtat ctttcctaaa | 1380 |
| gggtattatg ccgtggctgt ggtgaaggca tcggacacta gcatcacctg gaacaacctg | 1440 |
| aaaggcaaga agtcctgcca cactgggta gacagaaccg ctggttggaa catccctatg | 1500 |
| ggcatgctgt acaacaggat caaccactgc aaattcgatg aattttttcag tcaaggctgc | 1560 |
| gctcccgggt atgagaagaa ttccacccta tgtgacctgt gtattggccc actcaaatgt | 1620 |
| gctccgaaca acaaagagga atataatggt tacacaggg ctttcaggtg tctcgttgag | 1680 |
| aaaggagatg tagcctttgt gaaacaccag actgtcctgg ataacaccga aggaaagaac | 1740 |

-continued

| | |
|---|---|
| cctgccgaat gggctaagaa tctgaagcag gaagacttcg agttgctctg ccctgatggc | 1800 |
| accaggaagc ctgtgaaaga ttttgccagc tgccacctgg cccaagctcc aaaccatgtt | 1860 |
| gtggtctcac gaaaagagaa ggcagcccgg gttaaggctg tactgactag ccaggagact | 1920 |
| ttatttgggg gaagtgactg caccggcaat tctgttttgt tcaagtctac caccaaggac | 1980 |
| cttctgttca gggatgacac caaatgtttc gttaaacttc cagagggtac cacacctgaa | 2040 |
| aaatacttag gagcggagta catgcaatct gtcggtaaca tgaggaagtg ctcaacctca | 2100 |
| cgactcctgg aagcctgcac tttccacaaa cattaaaatc caagaggtgg gttgccactg | 2160 |
| tggtggagac agatgctccc tcccgtggcc catgggcttc tcttggtctt catgccctga | 2220 |
| gggggttgggg ctaactggtg tagtcttcgc tgctgtgcct taccacatac acagagcaca | 2280 |
| aaataaaaac gactgctgac tttaaaaaaa aaaaaaaaaa aaaa | 2324 |

<210> SEQ ID NO 22
<211> LENGTH: 1859
<212> TYPE: DNA
<213> ORGANISM: Mouse

<400> SEQUENCE: 22

| | |
|---|---|
| ggcgcaccta ccccagccta tgtgcgctcc gcaaggagaa ccgagccgct cgccagcggg | 60 |
| gcgcgctccc ggctgtgcca gtgcagaagg gtgcctgcga ggaagcaggg accacaagag | 120 |
| cagggcggct ccggagaaag tacaacttca tcgccgcagt ggtggagaag gtggcgccgt | 180 |
| ctgtggtcca cttgcagctg ttccgcagat gacagacaca caggttccca cactgatcta | 240 |
| aaggaggaga caccatcctg gacccagatc tcagttgtgt tcagaaaaga tggccaggac | 300 |
| gagcttcagg cagctcacaa agcacatgga agtggatcac ctctcaccaa ccaggaaatc | 360 |
| ccttcctcca gcggctctgg gttcatagtg tctgaggatg ggctcattgt caccaatgcc | 420 |
| cacgtcctca ccaaccagca gaagatccag gtagagctcc agagcggggc ccggtatgaa | 480 |
| gccaccgtca agacatcga ccataaactg gaccttgcac tgattaagat cgagccagat | 540 |
| actgagcttc cagtactgct gctgggccga tcctctgacc tccgggctgg agagtttgtg | 600 |
| gtagctttgg gcagcccatt ttctctgcag aacaccgtga ctgcagggat tgtcagcacc | 660 |
| acacagagag gcggcagaga gctgggactg aagaattcag acatagacta tatccagacg | 720 |
| gatgccatca ttaaccatgg aaattctggg ggtccgctgg tgaacttgga tggcgacgtg | 780 |
| attggtataa acactctgaa ggtgactgca gggatctctt ttgcgatccc ctctgatcgg | 840 |
| atcagacagt tcctggaaga ctatcatgag cgccagttga aaggcaaggc ccctttgcag | 900 |
| aagaaatacc tgggtcttcg aatgctgcct ctcactctga acctccttca ggaaatgaag | 960 |
| aggcaagatc cagagttccc tgatgtgagt tctggagttt ttgtatatga agtgattcag | 1020 |
| ggatcggctg ctgcaagctc ggggttgaga gaccatgatg taattgtcag cataaacggg | 1080 |
| caacctgtca ccaccacaac tgatgtcatt gaagctgtta aggacaatga ctttctctcc | 1140 |
| atcattgtgc ttcgaggaag tcaaaccttg tttctgacag tcacacctga ataatcaat | 1200 |
| taagtatctt actttgagaa actgcctagc aaaaccagtt atattacctg ttttgtatc | 1260 |
| gaagaggtgc cagagatggc agggtcttct ggagatcaag aaaaatggat gctttaaatg | 1320 |
| cagaagttca tgtttgtgtg catacatcaa cacacacaca cacacacaca cactcatgga | 1380 |
| tcctgaggtt gagagtgctc ttctgccgca aaaccttcct aactcaaatg gaaacagcta | 1440 |
| tggtgatctg ataaaacttg atgacagtaa gaactggaaa gcaggcaatt cctaactaaa | 1500 |
| tcttgatagg aaactttagt tacctccta t acagccacaa actggtatgt cacgcacatg | 1560 |

| | |
|---|---:|
| tacacataat tacctaccaa atattaagaa cctgaatctg gagtaaagag gtaatcacat | 1620 |
| tttaaataat accctttgt atactgaatt tcccaggtta tatccactct gggccagggt | 1680 |
| ttgtggatag aaaggtcatc acctataaga catcttggag ctgatgacat catactacca | 1740 |
| cacaggagtg tgatcatttt ggaggtagaa acaatttcgg acctttagag tttctgagaa | 1800 |
| tgtcttctat ttctattaaa ataattttc gaaccgttaa aaaaaaaaa aaaaaaaa | 1859 |

<210> SEQ ID NO 23
<211> LENGTH: 724
<212> TYPE: DNA
<213> ORGANISM: Mouse

<400> SEQUENCE: 23

| | |
|---|---:|
| atgcctgcct gtcgcctctg cttgctggcc gctggcctcc tactagggtt gctactgttc | 60 |
| accccccatct cagccacagg caccgatgca gagaaacccg gcgagtgccc ccagctcgaa | 120 |
| ccaattacgg actgtgtgtt ggagtgcact ttggacaagg actgtgcgga caaccgcaag | 180 |
| tgctgccagg cggctgcag ctctgtctgc tccaagccta atggaccgag cgaaggagag | 240 |
| ctctcaggga cagatactaa actctcagag actgggacta ctactcaatc agcgggcctt | 300 |
| gaccacacta ctaaaccacc gggaggtcaa gtctccacga agccaccggc tgtgaccagg | 360 |
| gaaggcttag gtgtccgaga aaagcagggc acctgcccca gcgtggacat acccaagctc | 420 |
| ggcctctgtg aggaccagtg tcaggtggac agccagtgtt ctggcaacat gaaatgctgc | 480 |
| cgcaatggat gtgggaagat ggcctgcacc acacccaaat tctgagcttc agcctccagc | 540 |
| agcctgagga acgagagag gttgtttctg ccggactgtg catctggagt cgttcctgtg | 600 |
| gcctcctttc tctctggtct ttgcatttct tcctggtccg acgaaagcat ctcctttttc | 660 |
| taaccaataa agtgatcgtt ttcagcaatg gagaagctat aaaaaaaaaa aaaaaaaaa | 720 |
| aaaa | 724 |

<210> SEQ ID NO 24
<211> LENGTH: 2395
<212> TYPE: DNA
<213> ORGANISM: Mouse

<400> SEQUENCE: 24

| | |
|---|---:|
| gaaagaatag agacagagaa ggagtttctg cattcttggg atcacaaacc agaccatgaa | 60 |
| agctggcatt cagaatgcct gcctaccaaa agtctcagca aggcccagca agctccacag | 120 |
| gatgcttttc aagggtggct ctgtggtgtg ggtacggcca aggtggggaa agccagtct | 180 |
| ttgggagcag actctttgta ggagtctgcc cttccctctt cccctgccca ctccactctg | 240 |
| acagccacag gtggaatgat gagggcccaa atgtgggaca tctatgctca gatattaaac | 300 |
| ctaagctcac gtaagaagtg ggcaaagact ggccctggtt tgtctgtaag agacccagag | 360 |
| tttcccaacc cccctgccat gagctaggtc atcacactaa tttgttgatg tttgctcctg | 420 |
| tttgccttaa ggatagtgac ccttgcctga cgcagatgtc atgtttaggc attaagtgtc | 480 |
| cataggtcat tccgtagggc atctagtaca cgtcggttca caaatctact tccaagaccc | 540 |
| tcagaatcct tcattaaagg gctgggcctg ggtgtctgaa tttctgatga gctccctgca | 600 |
| atatggttaa atgcactata actggaggtc agagccttag aaccgggggg agcagagcca | 660 |
| ccttgtaaat gttatcaggc taatcacaat gagatggccc cactgctagc tacgtctcag | 720 |
| cctccatcag ctcttgctgc ctcttccaca gctgcttaca tctgggacac ttgtgcccca | 780 |

-continued

```
ttcccaggcc atacaagcct ggaaggtggg ctggacagcc tcctccctga cctacatggg      840
aaggtctctc ctttttcttcc cgcccttttt tctaatgtgg atgcttccat taatcctctg     900
tttctggagc cttggaagat ctgtcttcca ttcattcatc cacccatcca tcattcaaca     960
tgaatgggtc atgtcacgtg ttgggtgcaa gggatactct ttcaaaacaa tccctcacga    1020
gactcacagt ctagtgaaga gcacacgcca gaaaccaatt agagaagcta ccaaccacga    1080
tggaacatca gggattcaaa acctcgggt gagagggagc ctactttctc tgtgttcttc    1140
taagagccct gatggctctc gattgctctg aacagaggtc cacttggtcc agtgctatca    1200
tgggtagtgc ccacgaggtt tccccagaga atactactgt agagcattct atactcccca    1260
cagggagaca ggaaaggatt cccagagcca tggctcttaa gatggtcctc gaaggaaaat    1320
ccagtcattt ccaagtgggc cctgaaccct gaggctatgg ggaggtcttc agaagtcctg    1380
gaagagtgac aacacccgag tcccaggagc tctgtgatgg caaccttctc ccttgaacac    1440
ccttttccat ttttgagcat cgagttggag aggtgattct gggacagggt gtgtatattt    1500
gtgttgttta aacacattca catgtaagct gcctgagggg aggggatgtt tgcctctagc    1560
tcagtcccag tggagctggg gggatgatga gtctgagtgg ctttagggcc atcattgaca    1620
ccacctcagt acaaacggac tcccctccct tcctccctct cttctatcct cctttccttc    1680
cttcccttag cagggctgcc aaggtgatat gggacagcga cagggcaaac gatcacctgt    1740
tgccttaatg aactttccac agctcactgc tggctaggtc gtagagtttc tccttgtctt    1800
gtgaggccca aggaaggagg ccaatctaaa gtgtcctcca taccttcccc ttgggggctt    1860
ttctgtaata cttgtttaaa aattgttctg atgatcatga tggaaacaga cagaccacct    1920
tagaaccaga ggcctgaaag cctgacctga ccagcacaga ttcccacttc agaaccccag    1980
ggctatggaa gtgcccttgt ccaacgctat gggaatagtc ctgtgggttg tctctgcttg    2040
ccactgtggc cagcattcca gtgcctacag ccacctgtgc ctacagccac ctgtgccatg    2100
agaagtgcct ctcctgctct atgccctgca tttgggatgc taagaagagg tgagggtgtg    2160
agcgagaaca gatccaccct tctcctaggt aggatcagct ctcaattggt gcttatcact    2220
agttatcaaa gaacagcaga gacagctgcg ttatccaaga gcaagtatt aggaccaaaa    2280 cctgttactg tatttaaagg aactttagtt tgcgtatctt acatttttat aaagtactgt    2340
aattcagggg gtggggtatg caacagagac agactaaccc atgtttgtca tttgc         2395
```

```
<210> SEQ ID NO 25
<211> LENGTH: 881
<212> TYPE: DNA
<213> ORGANISM: Mouse

<400> SEQUENCE: 25
gtgaggaatg gcgacctttt ttttaaaaag gtgcaggtcg aggatggggg tgtgtatacc       60
tgttacgcca tgggggagac tttcaacgag acactgtctg tggagttgaa agtgtataac     120
ttcaccttgc acggacacca tgacaccctc aacacagcct acactaccct ggtgggctgt    180
atcctcagtg tggttctggt cctcatatac ttgtacctca ccccttgccg ctgctggtgt    240
cggggtgtgg agaaaccttc cagccaccaa ggagatagcc tcagctcttc tatgctcagt    300
accacaccca accacgaccc tatggctggt ggggacaaag atgatggttt tgaccggcgg    360
gtggccttcc tggaacctgc tggacccggg cagggtcaaa atggcaaact caagccaggc    420
aacactctgc cggtgcccga agctacaggc aagggccaac ggaggatgtc cgatccagag    480
tcggtcagct cggtcttttc tgatacaccc attgtggtgt gagcagcgta ggctgatggg    540
```

-continued

```
gaggttctgc cccaggagag gtaccnctga gggatatgac agggtggaag agagggctgg      600
atgcccaagg gagtgggttc ctcctgacca ccagggaatc ggtcacaggc gccggaggag      660
gcaagacccc agtgagggtg tggatgctgc gagtttcacc tatggatatc ctcaggcaga      720
tgccacaccc ctacccaaag ccttggctat tctcagtgtg ggggaggggg acaggaacga      780
ggaaagggcg gaggggagga gcaaattccc taaactttt tgaggtcatc cctagctcct       840
taagagaaaa ccatttgaaa acaaaaaaaa aaaaaaaaa a                           881
```

<210> SEQ ID NO 26
<211> LENGTH: 556
<212> TYPE: DNA
<213> ORGANISM: Mouse

<400> SEQUENCE: 26

```
gcaccactcc cctggctcga gtcatctccc gggacactga acacagaga tattacctgc       60 taagtcacac acctgcctgc agtctcaccc tgggtcctga tatggaggaa atcacctgtg      120
cctttctcct gctgctagca gtctgccgg ccttggaagc cagtgaccca gttgataaag       180
acagtccctt ctactatgac tgggagagcc tgcagctggg aggattgatt tttggagggc      240
tcctgtgcat cgctggaatt gccatggccc tgagtggcaa gtgcaaatgt aggcgtaccc      300
ataagcccag ttccttacct ggaaaagcca ctccactcat cattccaggc tctgccaata      360
cctgctgaac tgaacacagg accaagtttg gaggcaggtt tttgacaact ttctgccgta      420
cttctcctct ggagaccttc ctctccagga tggcttccct agaacatact gttaagtctt      480
cattgacagg aaagggtgtg gcaaagctga ttttatatta aactggtctt gctgctcaaa      540
aaaaaaaaaa aaaaaa                                                      556
```

<210> SEQ ID NO 27
<211> LENGTH: 750
<212> TYPE: DNA
<213> ORGANISM: Mouse

<400> SEQUENCE: 27

```
gctgagtgtg gttctgggtg gaaccctcta cataggccat tatttagcca tgtattccga      60
aggcgccccc ttctggactg ggatcgtggc tatgctggct ggagctgttg ccttccttca      120
caagaaacgg ggtggtacct gctgggccct gatgaggacc cttcttgtgc tggcaagttt      180
ctgcaccgct gtggctgcca tcgttattgg gtctcgtgag ttgaattatt actggtattt      240
tctcggagat gatgtctgtc aaagagactc ttcatatgga tggtccacca tgcctagaac      300
cactccagtt cccgaagaag ctgataggat tgccttgtgc atatactaca caagcatgct      360
aaagaccctg ctcatgagcc tccaagctat gctcttgggt atctgggtgc tgctgctcct      420
ggcttctctc acccctgtat gtgtctacat ctggaaaaga ttttcacaa aggcggaaac       480 agaggagaag aaactgctgg gtgcagctgt gatctagcct ttcctcttgc tccgggcgtc      540
cctcctactg aagcctgaaa gaagaatcag gcaggactaa aagagccctc ccccactagc      600
agggccatgg ccactgcctg gttctgccca gcaccacagc agctctcagc agcacttgct      660
tgtctctcca tccttcaccg tcctatatcc ctcctcaggc agcaacttga taataaactc      720
tcctgttatt gctggcaaaa aaaaaaaaaa                                       750
```

<210> SEQ ID NO 28
<211> LENGTH: 1896
<212> TYPE: DNA

<213> ORGANISM: Mouse

<400> SEQUENCE: 28

| | | | | | |
|---|---|---|---|---|---|
| gtgaacatct | gtctcccttc | ctgcgggtgg | ccagccacag | tgccccggag | ggatctgcac | 60 |
| aatgctccag | cacactagcc | tggtgttact | cctcgcctct | atttggacca | ctaggcaccc | 120 |
| agtccaaggt | gccgacctcg | tgcaagacct | ttccatttct | acatgcagaa | tcatgggcgt | 180 |
| tgccttgtg | ggcagaaaca | aaaacccaca | gatgaatttc | acagaagcca | acgaggcctg | 240 |
| taagatgctg | ggactgactc | tggccagcag | ggaccaggta | gagtcagcgc | agaaatctgg | 300 |
| ctttgagact | tgcagctatg | gatgggttgg | agaacagttc | tctgtcatcc | ctcggatttt | 360 |
| ctcaaacccc | aggtgtggga | agaatggcaa | aggtgtcctg | atttggaatg | ctccctccag | 420 |
| ccaaaagttc | aaagcctatt | gccacaactc | atccgacacc | tgggttaact | cctgcattcc | 480 |
| agaaatcgtt | accacatttt | accccgtgtt | ggacactcaa | acaccgcaa | cagagttttc | 540 |
| tgtcagcagc | agcgcctact | tggcttcatc | ccctgactcc | acaacacctg | tttctgccac | 600 |
| cacccgggct | ccacctttga | cctccatggc | acggaagaca | aaaagattt | gtatcacgga | 660 |
| agtttataca | gaacctatca | ccatggctac | agaaacagaa | gcatttgttg | caagtggagc | 720 |
| agcattcaag | aacgaagcag | ctgggttttgg | aggtgtcccc | accgccctgc | tggtgctggc | 780 |
| tctcctcttc | tttggtgctg | ccgctgtgct | ggctgtttgc | tacgtgaaaa | ggtatgtgaa | 840 |
| ggccttccct | ttcacaacca | gaatcaaca | gaaggaaatg | atcgaaacca | aggttgtaaa | 900 |
| ggaagagaag | gctgatgacg | tcaacgctaa | tgaagaatca | aagaaaacca | ttaaaaaccc | 960 |
| agaggaggcc | aagagtccac | ccaaaactac | ggtgcgatgc | ttagaagctg | aagtttagat | 1020 |
| gcaagagagt | ggagaaggtg | cacacgaggc | aagtttcatg | ccccgggaac | caaagaagca | 1080 |
| agccactgtc | agttcctgca | gaaaaagact | gcagagttca | ccagaaggag | ccctctcctt | 1140 |
| actgcagtct | tctctggact | ctaccctctg | gcctccaacc | ttcccacagc | ctccctaacc | 1200 |
| cttctgtggc | tcacagcaga | ccagagagta | gagggagctt | tcaaagtacc | aggtcctaaa | 1260 |
| acagctccta | agctcacact | cagagacagg | cttccaggtt | gcctgacccc | catgaaaggc | 1320 |
| cagagtccct | gagacatggc | cagccccata | gttcaaaatc | ttcccacagg | gaaatacacc | 1380 |
| acctggccgt | gctcttttgga | accaggcaca | tgtaaaataa | ggaaaggaaa | acaacagaag | 1440 |
| gtcatggaga | gcctgggtga | cttgagactt | aatctctgga | aagccaaaat | aaacagagca | 1500 |
| tgagatggga | gctggggcca | cagatagcag | ccttgttggc | tgagactgta | aatacaggct | 1560 |
| ggggctgaga | agcctctcgg | ttaattgatc | tgcagcacgt | agacagactt | tcttttcttt | 1620 |
| ttactgttgc | tggtgttctc | tagagacaaa | tacacgttta | taagaaacct | aaaagcagga | 1680 |
| gagcccagga | gctgactcag | tggtaaagca | cttgcccggc | atgtacaaac | aaggcttcca | 1740 |
| gtccaatccc | cagaatccac | tgaccccaca | cacacaaaga | aacaaacaca | agtatgcatt | 1800 |
| tccattttt | acttgaatta | caggacccat | ggctgagaaa | ataactgtgt | taaaaggtta | 1860 |
| aaaaaaagga | gaaagtaca | aaaaaaaaa | aaaaaa | | | 1896 |

<210> SEQ ID NO 29
<211> LENGTH: 1854
<212> TYPE: DNA
<213> ORGANISM: Mouse

<400> SEQUENCE: 29

| | | | | | |
|---|---|---|---|---|---|
| gcccacatgg | tctgggccaa | cttggctgtg | tttgtcatct | gcttcctgcc | cttgcatgtg | 60 |
| gtcctgaccg | tgcaggtctc | cctgaacctc | aatacctgtg | ctgcccgaga | cacttcagc | 120 |

```
cgtgccctgt ccatcacagg taaactctca gacaccaact gctgcctgga tgccatctgt    180
tactactaca tggccagaga gttccaggaa gcgtccaagc cagccacgtc ttccaacaca    240
ccccacaaga gccaagattc ccagatcctg agcctcacct agaagaagtg aacacatgcc    300
aagggccaga ggaacctgtg atgtgagcaa ggagccctgg atcagcctga acctcctgtg    360
gggtctgagc actctaggag acccagttgg actagagagg ctgcatctgc tcccctgaaa    420
ggaccagagg actcaggctc taacgtccga cctgagggac cctggaacaa gaccacatat    480
ctcccattcc agatctagaa accctgggca ccagaatggg gccttgatgg ctagccactg    540
agtttaggat acacccctcc ccagagttgg tcctggcaag gtcctctgtc acctagatgc    600
aagtgatgag agataaagga cagacatacg gctcagagaa ccaggagaca tctttccaga    660
ggaccctcaa atggcttctt ccttttagga cctttaaact tcatgccaca tgtagggttg    720
ggcaaaaggg cagcagctgt ggtctggcag gctgtcctcc aaggcccatg actgtcactg    780
ttgctccagc tctgtattat gagggttcca gctcaggaga cccagtggtc ataacatcat    840
gttgagcaat cggacctgag cctcttctgg ttatttccat tctatagtgg gactgttgat    900
tcctgaggac agtggctatg gtagaggtct ctggagttta ttgtgaggaa gattgctgtt    960
tggtattcat gctctctgag gatgtggccc caggcttcga ggatctctgg agtaaaggat   1020
gagccacaaa gccagctttg agtcaggagc acatttggag atgtggtagc cctgggcttc   1080
cccctcaatg ctttgatttt tgtcttggtc caaatgctac agctgtaccc agagccagag   1140
cccctccagc tcagggagg ggggtactgg ctctccctac tctctacccc tacttcatcc   1200
aaggcctact gcctaactga ccccttttt tgtatgacct tttctacaaa accaaaaat   1260 ctgttcatcc ttcagacacc agagaaagga ttccactcaa gtataaattg gtgaactgat   1320
ttcctggagt tacttacaaa agcacggtga ctcttgggtg ctcagtcact gaaaagcctc   1380
actcagcata gataacaatc cccaaactgc accgctagat taccaatccc cactaaactt   1440
ccacctcaca cacacacttg gacacctgac ctgctccaga caaaaatgtg cctagggtgt   1500
gaggaagctg tggctgcgac ccaaggtgtg ctgaccctct tcgctctgcc aaggactact   1560
aacagcttca tgatcatcag cctattcgcc acagccgtat tttgcttgtt tcactggcat   1620
gactgtaggc cgagctgttc tgtggatcag agcagcgctt ttcctgttca ctgctgatga   1680
tcatcctaag ccagagaaat ggcttctctg ccacactggc ccactctccc tccagttctc   1740
acatcccctc caccctctgt tctgcagtat tatctaaacc ttccacttgg aaggaaggga   1800
tggtgtatct atataatatc aagatatagg atccacaaaa aaaaaaaaa aaaa          1854
```

<210> SEQ ID NO 30
<211> LENGTH: 2866
<212> TYPE: DNA
<213> ORGANISM: Mouse

<400> SEQUENCE: 30

```
ggtttcggag agataaggcg cttggccgtt actaactgga ctacaaagag ctggatcgga     60
ccggaaccac atggctcaac tcgcccgagc caccgctcc ccgctgtcat ggctgctgct    120
gctgttctgc tatgcactcc ggaaagcggg tggggatata cgtgtgctgg tgccctacaa    180
ttcgacaggc gtcttgggag ggtcgaccac cttgcactgt agtctgactt ctaatgagaa    240
tgtgactatc actcaaataa cctggatgaa gaaggattca ggtggatccc acgctcttgt    300
ggctgtcttc caccccaaga aggggcccaa catcaaagag ccagagaggg tgaaattctt    360
```

-continued

```
ggctgcccaa caggatctga ggaacgcatc tctggccatc tcgaacttaa gtgtagaaga    420
cgaaggcatc tatgaatgtc agattgccac attccccaga ggcagtagaa gcaccaatgc    480
ctggctgaag gtgcaagccc gacctaagaa cactgcagag ccctggagc  cctctcccac    540 cttgatactg caggatgtgg ctaaatgcat ctctgccaat ggtcaccctc ctggacgaat    600
ctcttggccc tcgaatgtga atggaagtca ccgtgaaatg aaggaaccag ggtcccagcc    660
gggcaccacc acagttacca gctacctctc catggtacct tctcgccagg cagacggcaa    720
gaacatcacc tgcacggtgg agcatgaaag cttacaggag ctggaccagc tgctggtgac    780
cctttcccaa ccctatccac ctgaaaacgt gtccatctct ggctatgacg gcaactggta    840
tgttggcctc actaacttga ccctgacctg tgaagctcac agcaaaccag cgcctgacat    900
ggctggatat aactggagca cgaacacggg tgactttccc aactctgtta gcgccaggg    960 caatatgctt ctaatctcca ccgtagagga tggtctcaat aacacggtca ttgtgtgcga   1020
agtcaccaat gccctagggt ctgggcaggg ccaagtgcac atcattgtta aagagaaacc   1080
tgagaatatg cagcaaaata caagattaca cctaggctac atctttctta tcgtctttgt   1140
cctcgctgta gtcatcatca tcgcagcact atacactata cgaagatgca ggcatggtcg   1200
tgctctgcag tccaatccct cagagaggga gaacgtccag tattcatctg tgaacggcga   1260
ctgtagactg aacatggagc caaacagcac aaggtgacgg tgctgggtag acagaactaa   1320
ggaacttgaa ggcatagcaa ctggaaccct actctcataa atgaagaagc ctccagagag   1380
actggctgct cagtgtgatg agcatagcaa gtttgggggg tctcccagga tgctgccgaa   1440
ttccacgttg tcaaaaggac ccatggaggc cagtgtgttg gctcactctt gacatctcag   1500
caagctgggg ggggggggg  gagcataaag caaggttgag tctagcttgg gctatagagc   1560
aaagccctgt ccatacacaa acaagctaag gggctttgag acggtcagaa actgaagtct   1620
tgctttgggt aaggtaaatc ctctaccgca tgtatgtgct agacttgaaa gacttccaca   1680
cagacctctt tataagttga ctccattggg gctatcccct cctctctgga caaggtctct   1740
gtatgtagcc aaggctaggc tcaaactcac agagatatgt ctgcttctac ctccccagtg   1800
ctagagttga aagtatttgt gccactgcac ttttctaggt cttcttttaa tgaagtaaag   1860
tatatattta taaaaagcta tttagttata tatatatata tttttgagac tatttcatag   1920
agcccaagct aacctcaaac ttactatgta gccaagagtg atggtaaact aatttatttt   1980
aatttatttg tcttcaattt taaccatcac ccaaccctg  ctcccttcca tatcttcttt   2040
caatccattt cattgtcttt ttcttcccag acactattct gacttacgtc tccattacaa   2100
acattttatt gaactacata aaaatgtgtg aaccacaaaa aaaaaatgta tttgtcaaaa   2160
ttgtagttgt ctttctgagg ctgacctgag ttctctgata ccattctctc cagttgtatc   2220
cagtttcctg taaacaatgt gactttgttt ttctcagtag ctaaaacatc ccaattatgt   2280
gagtgtacac tttctttact cattcctctg tgggccacca gctgggttgg ttccatatct   2340
gagctattgt gcatggaatt gtctctgtgg tgggtttagt aaactcccag gaatgcctgt   2400
acatgtttgt agaggccaga agaaggcaca aaatcttgag ccaggcttac atgcacttgt   2460
gagtagcccc acataggtgc taagaaccca gttcaggtcc tctgctgtgg gatggtgggc   2520
tgtgcacaga aagcctggtc ccggtctagc aaaggtctgg aactccggag ccggtgggct   2580
gtgatttaca ccagcatggg atggaaggag ttggacctcg cctcctgggc acctggctcc   2640
tgtcacatag ctacagcctc ccacagcccc cctatagggga ggtatgcagc atcaatcaca   2700
tagtagctgc actaagccct cccacatgca aataaggttt ccccaaactc tcagtccaag   2760
```

```
ccaatgaaaa gtacctgctg tcaaaccta  aatcatcccc aaaactctgt aagtcctatc   2820
agggaataaa atgtgtgtga aaactaaaaa aaaaaaaaaa aaaaaa                  2866

<210> SEQ ID NO 31
<211> LENGTH: 1093
<212> TYPE: DNA
<213> ORGANISM: Mouse

<400> SEQUENCE: 31
gcgaccactg agaccttgag actcagacac caagagagat gtttctagtt gggagcctcg    60
ttgtcctctg tgggctgctg gcccacagca cagcacagct ggcaggcttg ccattgcccc   120
tgggccaggg tccacccttg ccactgaacc agggcccacc gttgccactg aaccagggcc   180
agctgttgcc cctggctcag ggtctgcctt tggctgtaag cccagcactg ccttcaaatc   240
ccacagatct tcttgctgga aaattcacag atgctctcag cggtggcctg ctgtctgggg   300
ggctgctggg cattttggaa aatattccac tcctggatgt tataaagtct ggaggaggca   360
attctaatgg ccttgtgg ggcctgctgg gaaaactgac gtcatcagtt cctctcctga    420
acaacatcct cgacataaaa atcactgatc cgcagctgct agaacttggt cttgtgcaga   480
gtcctgatgg ccatcgtctc tatgtcacca tccctctggg cttgacactc aacgtaaata   540
tgcccgtagt tggaagtctt ttgcaattgg ctgtgaagct gaacattact gcagaagtct   600
tagccgtgaa agacaatcag gggaggattc atctggttct tggtgactgc acccactccc   660
ctggcagcct gaaaatcagc ttgctcaatg gagtcactcc tgttcaaagc tttttagaca   720
acctcacagg gatattgact aaagtccttc ctgagctgat ccagggcaag gtatgtcctc   780
tggtcaatgg gattctcagc ggtttggatg tcaccctggt gcacaacatt gctgaattac   840
tgatccatgg actacagttt gtcatcaaag tttaggcatc ccaggaagga aggctatctt   900
ggctgagctg aatcatttct tgctgctcag tctcctgcct cttgcccagt ctcccatggc   960
tcacagaaag gggcccacat cctggaaaat tatgtcttcc ttctcctcac ggagcctgat  1020
ctcttcccat caggcacgat taatcctgtg atcctcacta aataaaatag ctcttcatct  1080
gcaaaaaaaa aaa                                                    1093

<210> SEQ ID NO 32
<211> LENGTH: 1353
<212> TYPE: DNA
<213> ORGANISM: Mouse

<400> SEQUENCE: 32
gaaacagtat gagcaaacac tgagctgagg ggagcttctg attaagagcg ctccccagcg    60
aggcccgagg ccgtgaacct tcccagcaag agggtggtgg ttgctcctgg aagcctgcgc   120
ccagcagctg aagccatggc caccaccacg tgccaggtgt tagggcttct cctgtccctc   180
ctgggtctgg ccggctgcat agccgccact gggatggaca tgtggagcac tcaagacctg   240
tatgacaacc cagtcaccgc cgtgttccag catgaagggc tctggaggag ttgcgtgcaa   300
cagagctcgg ggttcaccga gtgccggcca tacttcacca tcctgggcct tccagccatg   360
ctgcaagctg tacgagccct gatgatcgtg gcattgttc tgggggtcat cggtatcctc   420
gtgtccatct tcgccctgaa gtgcattcgc attggtagca tggatgactc tgccaaggcc   480
aagatgactc tgacttctgg gatcttgttc atcatctccg gcatctgtgc aatcattggt   540
gtgtctgtgt ttgccaacat gctggtgacc aacttctgga tgtccacagc taacatgtac   600
```

-continued

| | |
|---|---|
| agcggcatgg gcggcatggg tggcatggtg cagaccgttc agaccaggta caccttcggt | 660 |
| gcagctctgt tcgtgggctg ggttgctgga ggcctcaccc tgattggggg agtgatgatg | 720 |
| tgcatcgcct gccgtggcct gacaccagat gacagcaact tcaaagctgt gtcttaccat | 780 |
| gcctctggcc aaaatgttgc ctacaggcct ggaggcttta aggccagcac tggctttggg | 840 |
| tccaacacca gaaacaagaa gatctacgat ggggtgccc gcacagaaga cgatgaacag | 900 |
| tctcatccta ccaagtatga ctatgtgtag tgctctaaga cccgccaacc tgtgtgcagg | 960 |
| aggaacccctt ccccaagaag agctcacccc aaagcaacgg gagtctacct tgttcccttg | 1020 |
| ttgatttcaa ctgacatctg aaagttggta aagcctgatt ttcatccata gggaggctag | 1080 |
| acagtcttgg ccacatgtgt ctgcctctaa atatcccatc acaaaacagc tgagttatcg | 1140 |
| tttatgagtt agaggccata acactcactt tagcccaacc ctctgctttt taccgtagac | 1200 |
| tttcttttca tctggtgatg gaatggaatt tgactcacag actaatactt taatggttta | 1260 |
| gagaaacttt ccttcctcgt acttaataag cctgctgatg gtcgattttc cagcttgacc | 1320 |
| accaagggaa attttaaaaa aaaaaaaaaa aaa | 1353 |

<210> SEQ ID NO 33
<211> LENGTH: 1046
<212> TYPE: DNA
<213> ORGANISM: Mouse

<400> SEQUENCE: 33

| | |
|---|---|
| gcctcagtcc acagctgtct ccccagctgc ttccagtgaa caccccggca gtctaggctc | 60 |
| ccacagcaat gagttggtgg agggacaact tctggatcat cttagctatg tccatcatct | 120 |
| tcatctccct ggtcctgggt ctcatcctgt actgtgtctg caggtggcag cttagacaag | 180 |
| gcaggaactg ggaaattgct aagccctcaa acaggatgg aagagatgaa gaaaagatgt | 240 |
| atgagaatgt tcttaattct tcaccaggcc agttacctgc tctgccaccc aggggttcac | 300 |
| cttttccagg agacctagcc ccacaggaag ctccaagaca accctcagct tggtactcat | 360 |
| cagtgaagaa agttaggaac aagaaggtct ttgctatctc gggctccacc gagccagaaa | 420 |
| atgattatga tgatgttgag attccagcaa ccaccgaaac ccagcactct aaaaccacac | 480 |
| cttttttggca agctgaagtg ggtttacaca gctcgtttta gaatactcta gaatagccgg | 540 |
| attataacac aagcacttcc taatccccag aggaagccac ctcagccatg tgaaagctac | 600 |
| agcagaagac aggacagctt gatgttcccg aggctccaga tgtttctgtt gctccagatg | 660 |
| tttctgctgc tccagatgtt tctgttgctc caaatatttc tgctgctcca gatgtttctg | 720 |
| ttgctccaga tgtttctgtt gctccagatg ctcctgttgc tccagatgct cctgatgttt | 780 |
| ctgacactgc agaagctcta ccccaagatt ctgaggatgt ggccttggca cctttgtgga | 840 |
| ggaagtttcc ttagtgcaga ccactgggcc tgtgagaact gactcatttc tcaacatttt | 900 |
| ctttcgttcc ctgggtgaat gtagctgtaa ggcagtgact ctcaaccttc ctaatgcagg | 960 |
| gatccttcaa tacaattcct tatttgtggt gatcctcaac cataaaatta ttttgttgct | 1020 |
| acttcaaaaa aaaaaaaaa aaaaaa | 1046 |

<210> SEQ ID NO 34
<211> LENGTH: 1261
<212> TYPE: DNA
<213> ORGANISM: Mouse

<400> SEQUENCE: 34

| | |
|---|---|
| gcacagacgg gtaaaccgct tgggaacctc gaggaaaaag aggctacgaa aaccttttcc | 60 |

```
taagaggcta caaatttgga agcagggaaa acccagacat gagatgtttt tagtttattt      120
ctccagaagg gggcactgta tcaattatgt gaagggacat gcagacagcc tagctccatg      180
gtgctgtggg gtaggactga ggagccctct ggccagaccc cagcacggcc atgtctctcc      240
caaggatcat gttcctggag gtcacgcccc tggtccttct cataagtggc tgtgcacagc      300
agctctctgg aggtatttgg aacattctgc tgtcacacat gggactgctc ttcctgaagc      360
ccacgctgtt cgtgggaaac atgggaagaa aggaagacgt gttgtgtgct gctcagtaga      420
cttcccacaa gccacctctc tcttctgaaa cgtcactgaa tggactggag aggactgcgg      480
gtttataaaa ctgcttttta tctgagaaca atgggtttgg aaactagtct cttttcttcc      540
cacttttaca gagcttctca aatcattcct ccaggccctg acttggacag gtaggggggc      600
agaccctggg tcccaaggtg cactgtccag gcacactgcc cacattgcta agagaagagg      660
ccctgctgcc agtggaccct tcaccccaca cgagacacct gtcttgcctt taggacaccc      720
tcctctagag agtggtgttg aaggaggggg acctatgtaa ggagttgggg caggcatgaa      780
tctgccaaat actggatatg gatccaaggc tgcccaggc acctgcacct ccagtgagtg       840
gtcagcaggt ggcgctgctg cccgccaggc ttcacagagt ccctttaggg agtctgctcc      900 cagatcccctt ctggtgcaca cttactggat gtcactgcaa gctctaccct ctgagcaggt     960
gttgcaccac agtggcgctg accctggccc cgcaacggca actgctgaag cagccattg      1020 cctcagccat tctcaagacc cttcaatttt taaaagcagt tcgattctgt aatatttatt     1080 tttcttttg aggatgtttc gttgccccgc agactgactg cagtgtgcac cattgcatga      1140
gccctgcctc agtgccctgt ggctccctgg gcactgctgc ccctctgtct aaagctgact     1200
gtggcagcac tgcccaacaa taaagctgac ctaaaagctg aaaaaaaaaa aaaaaaaaa      1260 a                                                                    1261
```

<210> SEQ ID NO 35
<211> LENGTH: 995
<212> TYPE: DNA
<213> ORGANISM: Mouse

<400> SEQUENCE: 35

```
gctcacccgc gtccgggcgc gcgcaggccc cgtctccttg ccttccaggc ctcatgcgct       60
cccgcgcctg gctcccgcga ccgctgcccg gaggaggggg gccgcgttg tctgcgcgtc       120 tacgcaggcc tcataggcac cgtggtcacc cccaactacc tggacaacgt gagcgcgcgc      180
gttgcgccct ggtgcggctg tgcggccagt ggaaaccggc gcgaagaatg cgaagccttc      240
cgcaagctct ttacaaggaa cccctgcttg gatggtgcca tacaagcctt tgacagcttg      300
cagccatcag ttctgcagga ccagactgct gggtgctgtt tccgcgggt gtcctggctg       360 tatgcactca ctgccctggc tctccaggcc ctgctctgat taggaacatg aaccgtggac      420
gacacagctg actgccatgt ctcccgatga ctgctcactg agctgaaact cccttgccct      480
caggtctgct gccctttgca ggcctggacc cttgtgtggc tgtcctctgg attggggct      540 ggaggctagg gtctgactga aaagcctgtg ttccctgtc agtaggcatc ttgtccgttt       600
tcttccccat cctagagctg agcacccata gatgaggcct cattgggtcc cctgggctta     660
cagagcagga cagagactag ccccgctcc tagaattcgg aactgtcctt ttccaagatg      720
acaaggcact aaggagatca tatgaacagg ctgacagaca aggctgccta aatacccctcc    780 cagttagcca ttattcacca ttaagcttac ccgtgtcaca gcactgacgt ggcttgtcac      840
```

-continued

```
ctatgacaca gtgtgtagac attaaggaga gactgaggtc cctcctgctc agcaccccac    900
tggcttccca ggctttccct gccatggttt ccccagcacc tgcagggct caataaaccc     960 atgtgcactg agaaaaaaaa aaaaaaaaaa aaaaa                               995
```

<210> SEQ ID NO 36
<211> LENGTH: 747
<212> TYPE: PRT
<213> ORGANISM: Rat

<400> SEQUENCE: 36

```
Glu Ala Thr Val Ile Thr Thr Glu Lys Arg Glu Arg Pro Ala Pro Pro
 1               5                  10                  15

Arg Glu Leu Leu Val Pro Gln Ala Glu Val Thr Ala Arg Ser Leu Arg
             20                  25                  30

Leu Gln Trp Val Pro Gly Ser Asp Gly Ala Ser Pro Ile Arg Tyr Phe
         35                  40                  45

Thr Val Gln Val Arg Glu Leu Pro Gly Gly Glu Trp Gln Thr Tyr Ser
     50                  55                  60

Ser Ser Ile Ser His Glu Ala Thr Leu Cys Ala Val Glu Arg Leu Arg
 65                  70                  75                  80

Pro Phe Thr Ser Tyr Lys Leu Arg Leu Lys Ala Thr Asn Asp Ile Gly
                 85                  90                  95

Asp Ser Asp Phe Ser Ala Glu Thr Glu Ala Val Thr Thr Leu Gln Asp
            100                 105                 110

Val Pro Gly Glu Pro Pro Gly Ser Val Ser Ala Thr Pro His Thr Thr
        115                 120                 125

Ser Ser Val Leu Ile Gln Trp Gln Pro Pro Arg Asp Glu Ser Leu Asn
    130                 135                 140

Gly Leu Leu Gln Gly Tyr Arg Ile Tyr Tyr Arg Glu Leu Glu Ser Glu
145                 150                 155                 160

Thr Gly Leu Ser Pro Glu Pro Lys Thr Leu Lys Ser Pro Ser Ala Leu
                165                 170                 175

Arg Ala Glu Leu Thr Ala Gln Ser Ser Phe Lys Thr Val Asn Ser Ser
            180                 185                 190

Ser Thr Leu Thr Thr Tyr Glu Leu Thr His Leu Lys Lys Tyr Arg Arg
        195                 200                 205

Tyr Glu Val Ile Met Thr Ala Tyr Asn Ile Ile Gly Glu Ser Pro Ala
    210                 215                 220

Ser Val Pro Val Glu Val Phe Val Gly Glu Ala Ala Pro Ala Met Ala
225                 230                 235                 240

Pro Gln Asn Ile Gln Val Thr Pro Leu Thr Ala Ser Gln Leu Glu Val
                245                 250                 255

Thr Trp Asp Pro Pro Pro Glu Ser Gln Asn Gly Asn Ile Gln Gly
            260                 265                 270

Tyr Lys Val Tyr Tyr Trp Glu Ala Asp Ser Arg Asn Glu Thr Glu Lys
        275                 280                 285

Met Lys Val Leu Phe Leu Pro Glu Pro Val Val Lys Ile Lys Asp Leu
    290                 295                 300

Thr Ser His Thr Lys Tyr Leu Val Ser Ile Ser Ala Phe Asn Ala Ala
305                 310                 315                 320

Gly Asp Gly Pro Arg Ser Asp Pro Cys Gln Gly Arg Thr His Gln Ala
                325                 330                 335

Ala Pro Gly Pro Pro Ser Phe Leu Glu Phe Ser Glu Ile Thr Ser Thr
            340                 345                 350
```

-continued

```
Thr Leu Asn Val Ser Trp Gly Glu Pro Ser Ala Ala Asn Gly Ile Leu
            355                 360                 365
Gln Gly Tyr Arg Val Val Tyr Glu Pro Leu Ala Pro Val Gln Gly Val
    370                 375                 380
Ser Lys Val Val Thr Val Asp Val Lys Gly Asn Trp Gln Arg Trp Leu
385                 390                 395                 400
Lys Val Arg Asp Leu Thr Lys Gly Val Thr Tyr Phe Phe Arg Val Gln
                405                 410                 415
Ala Arg Thr Ile Ala Tyr Gly Pro Glu Leu Gln Ala Asn Val Thr Ala
            420                 425                 430
Gly Pro Ala Glu Gly Ser Pro Gly Ser Pro Arg Asn Val Leu Val Thr
    435                 440                 445
Lys Ser Ala Ser Glu Leu Thr Leu Gln Trp Thr Glu Gly Asn Thr Gly
450                 455                 460
Asn Thr Pro Thr Thr Gly Tyr Val Ile Glu Ala Arg Pro Ser Asp Glu
465                 470                 475                 480
Gly Leu Trp Asp Met Phe Ala Lys Asp Ile Pro Arg Ser Ala Thr Ser
                485                 490                 495
Tyr Thr Val Gly Leu Asp Lys Leu Arg Gln Gly Val Thr Tyr Glu Phe
            500                 505                 510
Arg Val Val Ala Val Asn Lys Ala Gly Phe Gly Glu Pro Ser Arg Pro
    515                 520                 525
Ser Ile Ala Val Ser Ala Gln Ala Glu Ala Pro Phe Tyr Glu Glu Trp
530                 535                 540
Trp Phe Leu Leu Val Ile Ala Leu Ser Ser Leu Leu Leu Val Leu Leu
545                 550                 555                 560
Val Val Phe Val Leu Val Leu His Gly Gln Ser Lys Lys Tyr Lys Asn
                565                 570                 575
Cys Gly Ser Gly Lys Gly Ile Ser Asn Met Glu Glu Thr Val Thr Leu
            580                 585                 590
Asp Asn Gly Gly Phe Ala Ala Leu Glu Leu Asn Ser Arg His Leu Asn
    595                 600                 605
Val Lys Ser Thr Phe Ser Lys Lys Asn Gly Thr Arg Ser Pro Pro Arg
610                 615                 620
Pro Ser Pro Gly Gly Leu His Tyr Ser Asp Glu Asp Ile Cys Asn Lys
625                 630                 635                 640
Tyr Asn Gly Ala Val Leu Thr Glu Ser Val Asn Leu Lys Glu Lys Ser
                645                 650                 655
Val Asp Gly Ser Glu Ser Glu Ala Ser Asp Ser Asp Tyr Glu Glu Ala
            660                 665                 670
Leu Pro Lys His Ser Phe Val Asn His Tyr Met Ser Asp Pro Thr Tyr
    675                 680                 685
Tyr Asn Phe Trp Lys Arg Arg Pro Pro Ala Ala Ala Pro His Arg Tyr
690                 695                 700
Glu Ala Val Ala Gly Ala Glu Ala Gly Pro His Leu His Thr Val Ile
705                 710                 715                 720
Thr Thr Gln Ser Ala Gly Gly Val Tyr Thr Pro Ala Gly Pro Gly Ala
                725                 730                 735
Arg Ala Pro Leu Thr Gly Phe Ser Ser Phe Val
            740                 745

<210> SEQ ID NO 37
<211> LENGTH: 205
```

```
<212> TYPE: PRT
<213> ORGANISM: Mouse

<400> SEQUENCE: 37

Met Leu Gly Thr Leu Val Trp Met Leu Ala Val Gly Phe Leu Leu Ala
 1               5                  10                  15

Leu Ala Pro Gly Arg Ala Ala Gly Ala Leu Arg Thr Gly Arg Arg Pro
            20                  25                  30

Ala Arg Pro Arg Asp Cys Ala Asp Arg Pro Glu Glu Leu Leu Glu Gln
        35                  40                  45

Leu Tyr Gly Arg Leu Ala Ala Gly Val Leu Ser Ala Phe His His Thr
    50                  55                  60

Leu Gln Leu Gly Pro Arg Glu Gln Ala Arg Asn Ala Ser Cys Pro Ala
65                  70                  75                  80

Gly Gly Arg Ala Ala Asp Arg Arg Phe Arg Pro Thr Asn Leu Arg
                85                  90                  95

Ser Val Ser Pro Trp Ala Tyr Arg Ile Ser Tyr Asp Pro Ala Arg Phe
                100                 105                 110

Pro Arg Tyr Leu Pro Glu Ala Tyr Cys Leu Cys Arg Gly Cys Leu Thr
            115                 120                 125

Gly Leu Tyr Gly Glu Glu Asp Phe Arg Phe Arg Ser Thr Pro Val Phe
130                 135                 140

Ser Pro Ala Val Val Leu Arg Arg Thr Ala Ala Cys Ala Gly Gly Arg
145                 150                 155                 160

Ser Val Tyr Ala Glu His Tyr Ile Thr Ile Pro Val Gly Cys Thr Cys
                165                 170                 175

Val Pro Glu Pro Asp Lys Ser Ala Asp Ser Ala Asn Ser Ser Met Asp
            180                 185                 190

Lys Leu Leu Leu Gly Pro Ala Asp Arg Pro Ala Gly Arg
            195                 200                 205

<210> SEQ ID NO 38
<211> LENGTH: 238
<212> TYPE: PRT
<213> ORGANISM: Mouse

<400> SEQUENCE: 38

Met Leu Cys Phe Leu Arg Gly Met Ala Phe Val Pro Phe Leu Leu Val
 1               5                  10                  15

Thr Trp Ser Ser Ala Ala Phe Ile Ile Ser Tyr Val Val Ala Val Leu
            20                  25                  30

Ser Gly His Val Asn Pro Phe Leu Pro Tyr Ile Ser Asp Thr Gly Thr
        35                  40                  45

Thr Pro Pro Glu Ser Gly Ile Phe Gly Phe Met Ile Asn Phe Ser Ala
    50                  55                  60

Phe Leu Gly Ala Ala Thr Met Tyr Thr Arg Tyr Lys Ile Val Glu Lys
65                  70                  75                  80

Gln Asn Glu Thr Cys Tyr Phe Ser Thr Pro Val Phe Asn Leu Val Ser
                85                  90                  95

Leu Ala Leu Gly Leu Val Gly Cys Ile Gly Met Gly Ile Val Ala Asn
                100                 105                 110

Phe Gln Glu Leu Ala Val Pro Val His Asp Gly Ala Leu Leu
            115                 120                 125

Ala Phe Val Cys Gly Val Val Tyr Thr Leu Leu Gln Ser Ile Ile Ser
130                 135                 140
```

-continued

```
Tyr Lys Ser Cys Pro Gln Trp Asn Ser Leu Thr Thr Cys His Val Arg
145                 150                 155                 160

Met Ala Ile Ser Ala Val Ser Cys Ala Ala Val Val Pro Met Ile Ala
            165                 170                 175

Cys Ala Ser Leu Ile Ser Ile Thr Lys Leu Glu Trp Asn Pro Lys Glu
            180                 185                 190

Lys Asp Tyr Ile Tyr His Val Val Ser Ala Ile Cys Glu Trp Thr Val
            195                 200                 205

Ala Phe Gly Phe Ile Phe Tyr Phe Leu Thr Phe Ile Gln Asp Phe Gln
            210                 215                 220

Ser Val Thr Leu Arg Ile Ser Thr Glu Ile Asn Asp Asp Phe
225                 230                 235

<210> SEQ ID NO 39
<211> LENGTH: 492
<212> TYPE: PRT
<213> ORGANISM: Mouse

<400> SEQUENCE: 39

Leu Arg Leu Leu Leu Ala Trp Val Ala Ala Val Pro Ala Leu Gly Gln
1               5                   10                  15

Val Pro Trp Thr Pro Glu Pro Arg Ala Ala Cys Gly Pro Ser Ser Cys
            20                  25                  30

Tyr Ala Leu Phe Pro Arg Arg Arg Thr Phe Leu Glu Ala Trp Arg Ala
            35                  40                  45

Cys Arg Glu Leu Gly Gly Asn Leu Ala Thr Pro Arg Thr Pro Glu Glu
        50                  55                  60

Ala Gln Arg Val Asp Ser Leu Val Gly Val Gly Pro Ala Asn Gly Leu
65                  70                  75                  80

Leu Trp Ile Gly Leu Gln Arg Gln Ala Arg Gln Cys Gln Pro Gln Arg
                85                  90                  95

Pro Leu Arg Gly Phe Ile Trp Thr Thr Gly Asp Gln Asp Thr Ala Phe
            100                 105                 110

Thr Asn Trp Ala Gln Pro Ala Thr Glu Gly Pro Cys Pro Ala Gln Arg
        115                 120                 125

Cys Ala Ala Leu Glu Ala Ser Gly Glu His Arg Trp Leu Glu Gly Ser
145                 150                 155                 160

Cys Thr Leu Ala Val Asp Gly Tyr Leu Cys Gln Phe Gly Phe Glu Gly
145                 150                 155                 160

Ala Cys Pro Ala Leu Pro Leu Glu Val Gly Gln Ala Gly Pro Ala Val
            165                 170                 175

Tyr Thr Thr Pro Phe Asn Leu Val Ser Ser Glu Phe Glu Trp Leu Pro
            180                 185                 190

Phe Gly Ser Val Ala Ala Val Gln Cys Gln Ala Gly Arg Gly Ala Ser
            195                 200                 205

Leu Leu Cys Val Lys Gln Pro Ser Gly Gly Val Gly Trp Ser Gln Thr
            210                 215                 220

Gly Pro Leu Cys Pro Gly Thr Gly Cys Gly Pro Asp Asn Gly Gly Cys
225                 230                 235                 240

Glu His Glu Cys Val Glu Glu Val Asp Gly Ala Val Ser Cys Arg Cys
            245                 250                 255

Ser Glu Gly Phe Arg Leu Ala Ala Asp Gly His Ser Cys Glu Asp Pro
            260                 265                 270

Cys Ala Gln Ala Pro Cys Glu Gln Gln Cys Glu Pro Gly Gly Pro Gln
            275                 280                 285
```

-continued

```
Gly Tyr Ser Cys His Cys Arg Leu Gly Phe Arg Pro Ala Glu Asp Asp
            290                 295                 300
Pro His Arg Cys Val Asp Thr Asp Glu Cys Gln Ile Ala Gly Val Cys
305                 310                 315                 320
Gln Gln Met Cys Val Asn Tyr Val Gly Phe Glu Cys Tyr Cys Ser
                325                 330                 335
Glu Gly His Glu Leu Glu Ala Asp Gly Ile Ser Cys Ser Pro Ala Gly
            340                 345                 350
Ala Met Gly Ala Gln Ala Ser Gln Asp Leu Arg Asp Glu Leu Leu Asp
            355                 360                 365
Asp Gly Glu Glu Gly Glu Asp Glu Glu Pro Trp Glu Asp Phe Asp
370                 375                 380
Gly Thr Trp Thr Glu Glu Gln Gly Ile Leu Trp Leu Ala Pro Thr His
385                 390                 395                 400
Pro Pro Asp Phe Gly Leu Pro Tyr Arg Pro Asn Phe Pro Gln Asp Gly
                405                 410                 415
Glu Pro Gln Arg Leu His Leu Glu Pro Thr Trp Pro Pro Leu Lys
            420                 425                 430
Ala Pro Lys Gly Pro Gln Gln Pro Arg Gly Ala Ala Lys Thr Pro
            435                 440                 445
Lys Gly Asn Pro Ala Asn Pro Thr His Thr Thr Phe Cys Pro Gln Asp
            450                 455                 460
Leu Cys Tyr Phe Ser Tyr Thr Pro Thr Glu Pro Cys Pro Pro Thr
465                 470                 475                 480
Cys His Gly Pro Cys His Thr Ser Ser Cys Val Leu
                485                 490

<210> SEQ ID NO 40
<211> LENGTH: 464
<212> TYPE: PRT
<213> ORGANISM: Mouse

<400> SEQUENCE: 40

Met Gly Arg Ala Trp Gly Leu Leu Val Gly Leu Leu Gly Val Val Trp
1               5                   10                  15
Leu Leu Arg Leu Gly His Gly Glu Glu Arg Arg Pro Glu Thr Ala Ala
            20                  25                  30
Gln Arg Cys Phe Cys Gln Val Ser Gly Tyr Leu Asp Asp Cys Thr Cys
        35                  40                  45
Asp Val Glu Thr Ile Asp Lys Phe Asn Asn Tyr Arg Leu Phe Pro Arg
    50                  55                  60
Leu Gln Lys Leu Leu Glu Ser Asp Tyr Phe Arg Tyr Tyr Lys Val Asn
65                  70                  75                  80
Leu Lys Lys Pro Cys Pro Phe Trp Asn Asp Ile Asn Gln Cys Gly Arg
                85                  90                  95
Arg Asp Cys Ala Val Lys Pro Cys His Ser Asp Glu Val Pro Asp Gly
            100                 105                 110
Ile Lys Ser Ala Ser Tyr Lys Tyr Ser Glu Glu Ala Asn Arg Ile Glu
        115                 120                 125
Glu Cys Glu Gln Ala Glu Arg Leu Gly Ala Val Asp Glu Ser Leu Ser
    130                 135                 140
Glu Glu Thr Gln Lys Ala Val Leu Gln Trp Thr Lys His Asp Asp Ser
145                 150                 155                 160
Ser Asp Ser Phe Cys Glu Ile Asp Asp Ile Gln Ser Pro Asp Ala Glu
```

-continued

```
                165                 170                 175
Tyr Val Asp Leu Leu Asn Pro Glu Arg Tyr Thr Gly Tyr Lys Gly
                180                 185                 190

Pro Asp Ala Trp Arg Ile Trp Ser Val Ile Tyr Glu Glu Asn Cys Phe
            195                 200                 205

Lys Pro Gln Thr Ile Gln Arg Pro Leu Ala Ser Gly Arg Gly Lys Ser
        210                 215                 220

Lys Glu Asn Thr Phe Tyr Asn Trp Leu Glu Gly Leu Cys Val Glu Lys
225                 230                 235                 240

Arg Ala Phe Tyr Arg Leu Ile Ser Gly Leu His Ala Ser Ile Asn Val
                245                 250                 255

His Leu Ser Ala Arg Tyr Leu Leu Gln Asp Thr Trp Leu Glu Lys Lys
            260                 265                 270

Trp Gly His Asn Val Thr Glu Phe Gln Gln Arg Phe Asp Gly Ile Leu
        275                 280                 285

Thr Glu Gly Glu Gly Pro Arg Arg Leu Arg Asn Leu Tyr Phe Leu Tyr
        290                 295                 300

Leu Ile Glu Leu Arg Ala Leu Ser Lys Val Leu Pro Phe Phe Glu Arg
305                 310                 315                 320

Pro Asp Phe Gln Leu Phe Thr Gly Asn Lys Val Gln Asp Ala Glu Asn
                325                 330                 335

Lys Ala Leu Leu Glu Ile Leu His Glu Ile Lys Ser Phe Pro Leu
            340                 345                 350

His Phe Asp Glu Asn Ser Phe Ala Gly Asp Lys Asn Glu Ala His
        355                 360                 365

Lys Leu Lys Glu Asp Phe Arg Leu His Phe Arg Asn Ile Ser Arg Ile
370                 375                 380

Met Asp Cys Val Gly Cys Phe Lys Cys Arg Leu Trp Gly Lys Leu Gln
385                 390                 395                 400

Thr Gln Gly Leu Gly Thr Ala Leu Lys Ile Leu Phe Ser Glu Lys Leu
                405                 410                 415

Ile Ala Asn Met Pro Glu Ser Gly Pro Ser Tyr Glu Phe Gln Leu Thr
            420                 425                 430

Arg Gln Glu Ile Val Ser Leu Phe Asn Ala Phe Gly Arg Ile Ser Thr
        435                 440                 445

Ser Val Arg Glu Leu Glu Asn Phe Arg His Leu Leu Gln Asn Val His
    450                 455                 460

<210> SEQ ID NO 41
<211> LENGTH: 148
<212> TYPE: PRT
<213> ORGANISM: Rat

<400> SEQUENCE: 41

Leu Asn Trp Gln Ile Lys Lys Tyr Asp Thr Lys Ala Ala Tyr Cys Gln
1               5                   10                  15

Ser Lys Leu Ala Val Val Leu Phe Thr Lys Glu Leu Ser Arg Arg Leu
            20                  25                  30

Gln Gly Thr Gly Val Thr Val Asn Ala Leu His Pro Gly Val Ala Arg
        35                  40                  45

Thr Glu Leu Gly Arg His Thr Gly Met His Asn Ser Ala Phe Ser Gly
    50                  55                  60

Phe Met Leu Gly Pro Phe Phe Trp Leu Leu Phe Lys Ser Pro Gln Leu
65                  70                  75                  80
```

Ala Ala Gln Pro Ser Thr Tyr Leu Ala Val Ala Glu Glu Leu Glu Ser
                85                  90                  95

Val Ser Gly Lys Tyr Phe Asp Gly Leu Arg Glu Lys Ala Pro Ser Pro
            100                 105                 110

Glu Ala Glu Asp Glu Glu Val Ala Arg Arg Leu Trp Thr Glu Ser Ala
        115                 120                 125

His Leu Val Gly Leu Asp Met Ala His Gly Ser Ser Gly Arg Gly His
    130                 135                 140

Ser Ile Ser Arg
145

<210> SEQ ID NO 42
<211> LENGTH: 228
<212> TYPE: PRT
<213> ORGANISM: Mouse

<400> SEQUENCE: 42

Met Gly Phe Leu Leu Leu Leu Leu His Ala Ala Ile Ala Gly His
 1               5                  10                  15

Lys Asn Tyr Gly Thr His Asn His Cys Trp Leu Ser Leu His Arg Gly
             20                  25                  30

Phe Ile Trp Ser Phe Leu Gly Pro Ala Ala Ala Ile Ile Leu Ile Asn
         35                  40                  45

Leu Val Phe Tyr Phe Leu Ile Ile Trp Ile Leu Arg Ser Lys Leu Ser
 50                  55                  60

Ser Leu Asn Lys Glu Val Ser Thr Leu Gln Asp Thr Lys Val Met Thr
 65                  70                  75                  80

Phe Lys Ala Ile Val Gln Leu Phe Val Leu Gly Cys Ser Trp Gly Ile
             85                  90                  95

Gly Leu Phe Ile Phe Ile Glu Val Gly Lys Thr Val Arg Leu Ile Val
            100                 105                 110

Ala Tyr Leu Phe Thr Ile Ile Asn Val Leu Gln Gly Val Leu Ile Phe
        115                 120                 125

Met Val His Cys Leu Leu Asn Arg Gln Val Arg Met Glu Tyr Lys Lys
    130                 135                 140

Trp Phe His Arg Leu Arg Lys Glu Val Glu Ser Glu Ser Thr Glu Val
145                 150                 155                 160

Ser His Ser Thr Thr His Thr Lys Met Gly Leu Ser Leu Asn Leu Glu
                165                 170                 175

Asn Phe Cys Pro Thr Gly Asn Leu His Asp Pro Ser Asp Ser Ile Leu
            180                 185                 190

Pro Ser Thr Glu Val Ala Gly Val Tyr Leu Ser Thr Pro Arg Ser His
        195                 200                 205

Met Gly Ala Glu Asp Val Asn Ser Gly Thr His Ala Tyr Trp Ser Arg
    210                 215                 220

Thr Ile Ser Asp
225

<210> SEQ ID NO 43
<211> LENGTH: 373
<212> TYPE: PRT
<213> ORGANISM: Mouse

<400> SEQUENCE: 43

Met Lys Glu Tyr Val Met Leu Leu Leu Leu Ala Val Cys Ser Ala Lys
 1               5                  10                  15

```
Pro Phe Phe Ser Pro Ser His Thr Ala Leu Lys Asn Met Met Leu Lys
             20                  25                  30

Asp Met Glu Asp Thr Asp Asp Asp Asn Asp Asp Asp Asp Asn Ser
         35                  40                  45

Leu Phe Pro Thr Lys Glu Pro Val Asn Pro Phe Phe Pro Phe Asp Leu
 50                  55                  60

Phe Pro Thr Cys Pro Phe Gly Cys Gln Cys Tyr Ser Arg Val Val His
 65                  70                  75                  80

Cys Ser Asp Leu Gly Leu Thr Ser Val Pro Asn Asn Ile Pro Phe Asp
                 85                  90                  95

Thr Arg Met Val Asp Leu Gln Asn Asn Lys Ile Lys Glu Ile Lys Glu
                 100                 105                 110

Asn Asp Phe Lys Gly Leu Thr Ser Leu Tyr Ala Leu Ile Leu Asn Asn
             115                 120                 125

Asn Lys Leu Thr Lys Ile His Pro Lys Thr Phe Leu Thr Thr Lys Lys
         130                 135                 140

Leu Arg Arg Leu Tyr Leu Ser His Asn Gln Leu Ser Glu Ile Pro Leu
145                 150                 155                 160

Asn Leu Pro Lys Ser Leu Ala Glu Leu Arg Ile His Asp Asn Lys Val
                 165                 170                 175

Lys Lys Ile Gln Lys Asp Thr Phe Lys Gly Met Asn Ala Leu His Val
             180                 185                 190

Leu Glu Met Ser Ala Asn Pro Leu Glu Asn Asn Gly Ile Glu Pro Gly
         195                 200                 205

Ala Phe Glu Gly Val Thr Val Phe His Ile Arg Ile Ala Glu Ala Lys
     210                 215                 220

Leu Thr Ser Ile Pro Lys Gly Leu Pro Pro Thr Leu Leu Glu Leu His
225                 230                 235                 240

Leu Asp Phe Asn Lys Ile Ser Thr Val Glu Leu Glu Asp Leu Lys Arg
                 245                 250                 255

Tyr Arg Glu Leu Gln Arg Leu Gly Leu Gly Asn Asn Arg Ile Thr Asp
             260                 265                 270

Ile Glu Asn Gly Thr Phe Ala Asn Ile Pro Arg Val Arg Glu Ile His
         275                 280                 285

Leu Glu His Asn Lys Leu Lys Lys Ile Pro Ser Gly Leu Gln Glu Leu
     290                 295                 300

Lys Tyr Leu Gln Ile Ile Phe Leu His Tyr Asn Ser Ile Ala Lys Val
305                 310                 315                 320

Gly Val Asn Asp Phe Cys Pro Thr Val Pro Lys Met Lys Lys Ser Leu
                 325                 330                 335

Tyr Ser Ala Ile Ser Leu Phe Asn Asn Pro Met Lys Tyr Trp Glu Ile
             340                 345                 350

Gln Pro Ala Thr Phe Arg Cys Val Leu Gly Arg Met Ser Val Gln Leu
         355                 360                 365

Gly Asn Val Gly Lys
    370

<210> SEQ ID NO 44
<211> LENGTH: 466
<212> TYPE: PRT
<213> ORGANISM: Mouse

<400> SEQUENCE: 44

Met Trp Gly Cys Trp Leu Gly Leu Leu Leu Leu Leu Ala Gly Gln
 1               5                  10                  15
```

-continued

```
Ala Ala Leu Glu Ala Arg Arg Ser Arg Trp Arg Arg Glu Leu Ala Pro
             20                  25                  30

Gly Leu His Leu Arg Gly Ile Arg Asp Ala Gly Gly Arg Tyr Cys Gln
             35                  40                  45

Glu Gln Asp Met Cys Cys Arg Gly Arg Ala Asp Glu Cys Ala Leu Pro
         50                  55                  60

Tyr Leu Gly Ala Thr Cys Tyr Cys Asp Leu Phe Cys Asn Arg Thr Val
 65                  70                  75                  80

Ser Asp Cys Cys Pro Asp Phe Trp Asp Phe Cys Leu Gly Ile Pro Pro
                 85                  90                  95

Pro Phe Pro Pro Val Gln Gly Cys Met His Gly Gly Arg Ile Tyr Pro
             100                 105                 110

Val Phe Gly Thr Tyr Trp Asp Asn Cys Asn Arg Cys Thr Cys His Glu
             115                 120                 125

Gly Gly His Trp Glu Cys Asp Gln Glu Pro Cys Leu Val Asp Pro Asp
         130                 135                 140

Met Ile Lys Ala Ile Asn Arg Gly Asn Tyr Gly Trp Gln Ala Gly Asn
145                 150                 155                 160

His Ser Ala Phe Trp Gly Met Thr Leu Asp Glu Gly Ile Arg Tyr Arg
                 165                 170                 175

Leu Gly Thr Ile Arg Pro Ser Ser Thr Val Met Asn Met Asn Glu Ile
             180                 185                 190

Tyr Thr Val Leu Gly Gln Gly Glu Val Leu Pro Thr Ala Phe Glu Ala
             195                 200                 205

Ser Glu Lys Trp Pro Asn Leu Ile His Glu Pro Leu Asp Gln Gly Asn
         210                 215                 220

Cys Ala Gly Ser Trp Ala Phe Ser Thr Ala Ala Val Ala Ser Asp Arg
225                 230                 235                 240

Val Ser Ile His Ser Leu Gly His Met Thr Pro Ile Leu Ser Pro Gln
                 245                 250                 255

Asn Leu Leu Ser Cys Asp Thr His His Gln Gln Gly Cys Arg Gly Gly
             260                 265                 270

Arg Leu Asp Gly Ala Trp Trp Phe Leu Arg Arg Arg Gly Val Val Ser
             275                 280                 285

Asp Asn Cys Tyr Pro Phe Ser Gly Arg Glu Gln Asn Glu Ala Ser Pro
290                 295                 300

Thr Pro Arg Cys Met Met His Ser Arg Ala Met Gly Arg Gly Lys Arg
305                 310                 315                 320

Gln Ala Thr Ser Arg Cys Pro Asn Gly Gln Val Asp Ser Asn Asp Ile
                 325                 330                 335

Tyr Gln Val Thr Pro Ala Tyr Arg Leu Gly Ser Asp Glu Lys Glu Ile
             340                 345                 350

Met Lys Glu Leu Met Glu Asn Gly Pro Val Gln Ala Leu Met Glu Val
         355                 360                 365

His Glu Asp Phe Phe Leu Tyr Gln Arg Gly Ile Tyr Ser His Thr Pro
         370                 375                 380

Val Ser Gln Gly Arg Pro Glu Gln Tyr Arg Arg His Gly Thr His Ser
385                 390                 395                 400

Val Lys Ile Thr Gly Trp Gly Glu Glu Thr Leu Pro Asp Gly Arg Thr
                 405                 410                 415

Ile Lys Tyr Trp Thr Ala Ala Asn Ser Trp Gly Pro Trp Trp Gly Glu
             420                 425                 430
```

```
Arg Gly His Phe Arg Ile Val Arg Gly Thr Asn Glu Cys Asp Ile Glu
            435                 440                 445

Thr Phe Val Leu Gly Val Trp Gly Arg Val Gly Met Glu Asp Met Gly
    450                 455                 460

His His
465

<210> SEQ ID NO 45
<211> LENGTH: 422
<212> TYPE: PRT
<213> ORGANISM: Mouse

<400> SEQUENCE: 45

Met Asp Phe Trp Leu Trp Leu Leu Tyr Phe Leu Pro Val Ser Gly Ala
1               5                   10                  15

Leu Arg Val Leu Pro Glu Val Gln Leu Asn Val Glu Trp Gly Gly Ser
            20                  25                  30

Ile Ile Ile Glu Cys Pro Leu Pro Gln Leu His Val Arg Met Tyr Leu
            35                  40                  45

Cys Arg Gln Met Ala Lys Pro Gly Ile Cys Ser Thr Val Val Ser Asn
50                  55                  60

Thr Phe Val Lys Lys Glu Tyr Glu Arg Arg Val Thr Leu Thr Pro Cys
65                  70                  75                  80

Leu Asp Lys Lys Leu Phe Leu Val Glu Met Thr Gln Leu Thr Glu Asn
                85                  90                  95

Asp Asp Gly Ile Tyr Ala Cys Gly Val Gly Met Lys Thr Asp Lys Gly
            100                 105                 110

Lys Thr Gln Lys Ile Thr Leu Asn Val His Asn Glu Tyr Pro Glu Pro
            115                 120                 125

Phe Trp Glu Asp Glu Trp Thr Ser Glu Arg Pro Arg Trp Leu His Arg
130                 135                 140

Phe Leu Gln His Gln Met Pro Trp Leu His Gly Ser Glu His Pro Ser
145                 150                 155                 160

Ser Ser Gly Val Ile Ala Lys Val Thr Thr Pro Ala Ser Lys Thr Glu
                165                 170                 175

Ala Pro Pro Val His Gln Pro Ser Ser Ile Thr Ser Val Thr Gln His
            180                 185                 190

Pro Arg Val Tyr Arg Ala Phe Ser Val Ser Ala Thr Lys Ser Pro Ala
            195                 200                 205

Leu Leu Pro Ala Thr Thr Ala Ser Lys Thr Ser Thr Gln Gln Ala Ile
210                 215                 220

Arg Pro Leu Glu Ala Ser Tyr Ser His His Thr Arg Leu His Glu Gln
225                 230                 235                 240

Arg Thr Arg His His Gly Pro His Tyr Gly Arg Glu Asp Arg Gly Leu
                245                 250                 255

His Ile Pro Ile Pro Glu Phe His Ile Leu Ile Pro Thr Phe Leu Gly
            260                 265                 270

Phe Leu Leu Leu Val Leu Leu Gly Leu Val Val Lys Arg Ala Ile Gln
            275                 280                 285

Arg Arg Arg Ala Ser Ser Arg Arg Ala Gly Arg Leu Ala Met Arg Arg
290                 295                 300

Arg Gly Arg Gly Ala Ser Arg Pro Phe Pro Thr Gln Arg Arg Asp Ala
305                 310                 315                 320

Pro Gln Arg Pro Arg Ser Gln Asn Asn Val Tyr Ser Ala Cys Pro Arg
                325                 330                 335
```

```
Arg Ala Arg Gly Pro Asp Ser Leu Gly Pro Ala Glu Ala Pro Leu Leu
            340                 345                 350

Asn Ala Pro Ala Ser Ala Ser Pro Ala Ser Pro Gln Val Leu Glu Ala
            355                 360                 365

Pro Trp Pro His Thr Pro Ser Leu Lys Met Ser Cys Glu Tyr Val Ser
            370                 375                 380

Leu Gly Tyr Gln Pro Ala Val Asn Leu Glu Asp Pro Asp Ser Asp Asp
385                 390                 395                 400

Tyr Ile Asn Ile Pro Asp Pro Ser His Leu Pro Ser Tyr Ala Pro Gly
                405                 410                 415

Pro Arg Ser Ser Cys Gln
            420

<210> SEQ ID NO 46
<211> LENGTH: 228
<212> TYPE: PRT
<213> ORGANISM: Mouse

<400> SEQUENCE: 46

Met Lys Ala Leu Arg Ala Val Leu Leu Ile Leu Leu Leu Ser Gly Gln
1               5                   10                  15

Pro Gly Ser Gly Trp Ala Gln Glu Asp Gly Asp Ala Asp Pro Glu Pro
            20                  25                  30

Glu Asn Tyr Asn Tyr Asp Asp Asp Asp Glu Glu Glu Glu Glu Glu Glu
            35                  40                  45

Thr Asn Met Ile Pro Gly Ser Arg Asp Arg Ala Pro Leu Gln Cys Tyr
    50                  55                  60

Phe Cys Gln Val Leu His Ser Gly Glu Ser Cys Asn Gln Thr Gln Ser
65                  70                  75                  80

Cys Ser Ser Lys Pro Phe Cys Ile Thr Leu Val Ser His Ser Gly
            85                  90                  95

Thr Asp Lys Gly Tyr Leu Thr Thr Tyr Ser Met Trp Cys Thr Asp Thr
            100                 105                 110

Cys Gln Pro Ile Ile Lys Thr Val Gly Gly Thr Gln Met Thr Gln Thr
            115                 120                 125

Cys Cys Gln Ser Thr Leu Cys Asn Ile Pro Pro Trp Gln Asn Pro Gln
            130                 135                 140

Val Gln Asn Pro Leu Gly Gly Arg Ala Asp Ser Pro Leu Glu Ser Gly
145                 150                 155                 160

Thr Arg His Pro Gln Gly Gly Lys Phe Ser His Pro Gln Val Val Lys
            165                 170                 175

Ala Ala His Pro Gln Ser Asp Gly Ala Asn Leu Pro Lys Ser Gly Lys
            180                 185                 190

Ala Asn Gln Pro Gln Gly Ser Gly Ala Gly Tyr Pro Ser Gly Trp Thr
            195                 200                 205

Lys Phe Gly Asn Ile Ala Leu Leu Leu Ser Phe Phe Thr Cys Leu Trp
        210                 215                 220

Ala Ser Gly Ala
225

<210> SEQ ID NO 47
<211> LENGTH: 269
<212> TYPE: PRT
<213> ORGANISM: Mouse

<400> SEQUENCE: 47
```

-continued

Gly Cys Ser Asp Gly Glu Asn Gln Arg Ser Gly His Leu Ser Val Ser
1               5                   10                  15

Leu Gln Leu Ser Leu Lys Val Leu Leu Ile Arg Met Ala Ser Gly Trp
            20                  25                  30

Phe Tyr Leu Ser Cys Met Val Leu Gly Ser Leu Gly Ser Met Cys Ile
            35                  40                  45

Leu Phe Thr Ala Tyr Trp Met Gln Tyr Trp Arg Gly Gly Phe Ala Trp
        50                  55                  60

Asp Gly Thr Val Leu Met Phe Asn Trp His Pro Val Leu Met Val Ala
65                  70                  75                  80

Gly Met Val Val Leu Tyr Gly Ala Ala Ser Leu Val Tyr Arg Leu Pro
                85                  90                  95

Ser Ser Trp Val Gly Pro Arg Leu Pro Trp Lys Val Leu His Ala Ala
                100                 105                 110

Leu His Leu Leu Ala Phe Thr Cys Thr Val Val Gly Leu Ile Ala Val
            115                 120                 125

Phe Arg Phe His Asn His Ser Arg Ile Ala His Leu Tyr Ser Leu His
        130                 135                 140

Ser Trp Leu Gly Ile Thr Thr Val Leu Phe Ala Cys Gln Trp Phe
145                 150                 155                 160

Leu Gly Phe Ala Val Phe Leu Leu Pro Trp Ala Ser Gln Trp Leu Arg
                165                 170                 175

Ser Leu Leu Lys Pro Leu His Val Phe Phe Gly Ala Cys Ile Leu Ser
            180                 185                 190

Leu Ser Ile Thr Ser Val Ile Ser Gly Ile Asn Glu Lys Leu Phe Phe
        195                 200                 205

Val Leu Lys Asn Ala Thr Lys Pro Tyr Ser Ser Leu Pro Gly Glu Ala
        210                 215                 220

Val Phe Ala Asn Ser Thr Gly Leu Leu Val Val Ala Phe Gly Leu Leu
225                 230                 235                 240

Val Leu Tyr Val Leu Leu Ala Ser Ser Trp Lys Arg Pro Asp Pro Gly
                245                 250                 255

Ala Leu Thr Asp Arg Gln Pro Leu Leu His Asp Arg Glu
            260                 265

<210> SEQ ID NO 48
<211> LENGTH: 188
<212> TYPE: PRT
<213> ORGANISM: Mouse

<400> SEQUENCE: 48

Met Arg Leu Pro Leu Pro Leu Leu Leu Phe Gly Cys Arg Ala Ile
1               5                   10                  15

Leu Gly Ser Ala Gly Asp Arg Val Ser Leu Ser Ala Ser Ala Pro Thr
            20                  25                  30

Leu Asp Asp Glu Glu Lys Tyr Ser Ala His Met Pro Ala His Leu Arg
        35                  40                  45

Cys Asp Ala Cys Arg Ala Val Ala Phe Gln Met Gly Gln Arg Leu Ala
    50                  55                  60

Lys Ala Glu Ala Lys Ser His Thr Pro Asp Ala Ser Gly Leu Gln Glu
65                  70                  75                  80

Leu Ser Glu Ser Thr Tyr Thr Asp Val Leu Asp Gln Thr Cys Ser Gln
            85                  90                  95

Asn Trp Gln Ser Tyr Gly Val His Glu Val Asn Gln Met Lys Arg Leu

-continued

```
                100                 105                 110
Thr Gly Pro Gly Leu Ser Lys Gly Pro Glu Pro Arg Ile Ser Val Met
            115                 120                 125

Ile Ser Gly Gly Pro Trp Pro Asn Arg Leu Ser Lys Thr Cys Phe His
        130                 135                 140

Tyr Leu Gly Glu Phe Gly Glu Asp Gln Ile Tyr Glu Ala Tyr Arg Gln
145                 150                 155                 160

Gly Gln Ala Asn Leu Glu Ala Leu Leu Cys Gly Gly Thr His Gly Pro
                165                 170                 175

Cys Ser Gln Glu Ile Leu Ala Gln Arg Glu Glu Leu
                180                 185

<210> SEQ ID NO 49
<211> LENGTH: 247
<212> TYPE: PRT
<213> ORGANISM: Mouse

<400> SEQUENCE: 49

Met Ile Pro Gln Val Val Thr Ser Glu Thr Val Thr Val Ile Ser Pro
1               5                   10                  15

Asn Gly Ile Ser Phe Pro Gln Thr Asp Lys Pro Gln Pro Ser His Gln
            20                  25                  30

Ser Gln Asp Arg Leu Lys Lys His Leu Lys Ala Glu Ile Lys Val Met
        35                  40                  45

Ala Ala Ile Gln Ile Met Cys Ala Val Met Val Leu Ser Leu Gly Ile
    50                  55                  60

Ile Leu Ala Ser Val Pro Ser Asn Leu His Phe Thr Ser Val Phe Ser
65                  70                  75                  80

Ile Leu Leu Glu Ser Gly Tyr Pro Phe Val Gly Ala Leu Phe Phe Ala
                85                  90                  95

Ile Ser Gly Ile Leu Ser Ile Val Thr Glu Lys Lys Met Thr Lys Pro
            100                 105                 110

Leu Val His Ser Ser Leu Ala Leu Ser Ile Leu Ser Val Leu Ser Ala
        115                 120                 125

Leu Thr Gly Ile Ala Ile Leu Ser Val Ser Leu Ala Ala Leu Glu Pro
    130                 135                 140

Ala Leu Gln Gln Cys Lys Leu Ala Phe Thr Gln Leu Asp Thr Thr Gln
145                 150                 155                 160

Asp Ala Tyr His Phe Phe Ser Pro Glu Pro Leu Asn Ser Cys Phe Val
                165                 170                 175

Ala Lys Ala Ala Leu Thr Gly Val Phe Ser Leu Met Leu Ile Ser Ser
            180                 185                 190

Val Leu Glu Leu Gly Leu Ala Val Leu Thr Ala Thr Leu Trp Trp Lys
        195                 200                 205

Gln Ser Ser Ser Ala Phe Ser Gly Asn Val Ile Phe Leu Ser Gln Asn
    210                 215                 220

Ser Lys Asn Lys Ser Ser Val Ser Ser Glu Ser Leu Cys Asn Pro Thr
225                 230                 235                 240

Tyr Glu Asn Ile Leu Thr Ser
                245

<210> SEQ ID NO 50
<211> LENGTH: 182
<212> TYPE: PRT
<213> ORGANISM: Mouse
```

```
<400> SEQUENCE: 50

Pro Phe His Cys His Val Trp Ser Leu Cys Leu Gln Gly Ser Lys Gln
 1               5                  10                  15

Ser Gly Leu Cys Gln Val Gln Arg Asp Leu Gly Arg Asp Asp Arg Ser
                20                  25                  30

Val Arg Gly Ser Lys Ala Ala Val Val Ala Gly Ala Val Val Gly Thr
            35                  40                  45

Phe Val Gly Leu Val Leu Ile Ala Gly Leu Val Leu Leu Tyr Gln Arg
 50                  55                  60

Arg Ser Lys Thr Leu Glu Glu Leu Ala Asn Asp Ile Lys Glu Asp Ala
 65                  70                  75                  80

Ile Ala Pro Arg Thr Leu Pro Trp Thr Lys Gly Ser Asp Thr Ile Ser
                85                  90                  95

Lys Asn Gly Thr Leu Ser Ser Val Thr Ser Ala Arg Ala Leu Arg Pro
            100                 105                 110

Pro Lys Ala Ala Pro Pro Arg Pro Gly Thr Phe Thr Pro Thr Pro Ser
        115                 120                 125

Val Ser Ser Gln Ala Leu Ser Ser Pro Arg Leu Pro Arg Val Asp Glu
130                 135                 140

Pro Pro Pro Gln Ala Val Ser Leu Thr Pro Gly Gly Val Ser Ser Ser
145                 150                 155                 160

Ala Leu Ser Arg Met Gly Ala Val Pro Val Met Val Pro Ala Gln Ser
                165                 170                 175

Gln Ala Gly Ser Leu Val
            180

<210> SEQ ID NO 51
<211> LENGTH: 248
<212> TYPE: PRT
<213> ORGANISM: Mouse

<400> SEQUENCE: 51

Met Ser Trp Ser Pro Ile Leu Pro Phe Leu Ser Leu Leu Leu Leu Leu
 1               5                  10                  15

Phe Pro Leu Glu Val Pro Arg Ala Ala Thr Ala Ser Leu Ser Gln Ala
                20                  25                  30

Ser Ser Glu Gly Thr Thr Thr Cys Lys Val His Asp Val Cys Leu Leu
            35                  40                  45

Gly Pro Arg Pro Leu Pro Pro Ser Pro Pro Val Arg Val Ser Leu Tyr
 50                  55                  60

Tyr Glu Ser Leu Cys Gly Ala Cys Arg Tyr Phe Leu Val Arg Asp Leu
 65                  70                  75                  80

Phe Pro Thr Trp Leu Met Val Met Glu Ile Met Asn Ile Thr Leu Val
                85                  90                  95

Pro Tyr Gly Asn Ala Gln Glu Arg Asn Val Ser Gly Thr Trp Glu Phe
            100                 105                 110

Thr Cys Gln His Gly Glu Leu Glu Cys Arg Leu Asn Met Val Glu Ala
        115                 120                 125

Cys Leu Leu Asp Lys Leu Glu Lys Glu Ala Ala Phe Leu Thr Ile Val
130                 135                 140

Cys Met Glu Glu Met Asp Asp Met Glu Lys Lys Leu Gly Pro Cys Leu
145                 150                 155                 160

Gln Val Tyr Ala Pro Glu Val Ser Pro Glu Ser Ile Met Glu Cys Ala
                165                 170                 175
```

```
Thr Gly Lys Arg Gly Thr Gln Leu Met His Glu Asn Ala Gln Leu Thr
            180                 185                 190

Asp Ala Leu His Pro Pro His Glu Tyr Val Pro Trp Val Leu Val Asn
            195                 200                 205

Glu Lys Pro Leu Lys Asp Pro Ser Glu Leu Leu Ser Ile Val Cys Gln
            210                 215                 220

Leu Asp Gln Gly Thr Glu Lys Pro Asp Ile Cys Ser Ile Ala Asp
225                 230                 235                 240

Ser Pro Arg Lys Val Cys Tyr Lys
                245
```

<210> SEQ ID NO 52
<211> LENGTH: 278
<212> TYPE: PRT
<213> ORGANISM: Mouse

<400> SEQUENCE: 52

```
Met Gln Thr Met Trp Gly Ser Gly Glu Leu Leu Val Ala Trp Phe Leu
  1               5                  10                  15

Val Leu Ala Ala Asp Gly Thr Thr Glu His Val Tyr Arg Pro Ser Arg
             20                  25                  30

Arg Val Cys Thr Val Gly Ile Ser Gly Gly Ser Ile Ser Glu Thr Phe
             35                  40                  45

Val Gln Arg Val Tyr Gln Pro Tyr Leu Thr Thr Cys Asp Gly His Arg
 50                  55                  60

Ala Cys Ser Thr Tyr Arg Thr Ile Tyr Arg Thr Ala Tyr Arg Arg Ser
 65                  70                  75                  80

Pro Gly Val Thr Pro Ala Arg Pro Arg Tyr Ala Cys Cys Pro Gly Trp
             85                  90                  95

Lys Arg Thr Ser Gly Leu Pro Gly Ala Cys Gly Ala Ala Ile Cys Gln
            100                 105                 110

Pro Pro Cys Gly Asn Gly Gly Ser Cys Ile Arg Pro Gly His Cys Arg
            115                 120                 125

Cys Pro Val Gly Trp Gln Gly Asp Thr Cys Gln Thr Asp Val Asp Glu
            130                 135                 140

Cys Ser Thr Gly Glu Ala Ser Cys Pro Gln Arg Cys Val Asn Thr Val
145                 150                 155                 160

Gly Ser Tyr Trp Cys Gln Gly Trp Glu Gly Gln Ser Pro Ser Ala Asp
            165                 170                 175

Gly Thr Arg Cys Leu Ser Lys Glu Gly Pro Ser Pro Val Ala Pro Asn
            180                 185                 190

Pro Thr Ala Gly Val Asp Ser Met Ala Arg Glu Val Tyr Arg Leu
            195                 200                 205

Gln Ala Arg Val Asp Val Leu Glu Gln Lys Leu Gln Leu Val Leu Ala
            210                 215                 220

Pro Leu His Ser Leu Ala Ser Arg Ser Thr Glu His Gly Leu Gln Asp
225                 230                 235                 240

Pro Gly Ser Leu Leu Ala His Ser Phe Gln Gln Leu Asp Arg Ile Asp
            245                 250                 255

Ser Leu Ser Glu Gln Val Ser Phe Leu Glu Glu His Leu Gly Ser Cys
            260                 265                 270

Ser Cys Lys Lys Asp Leu
            275
```

<210> SEQ ID NO 53

```
<211> LENGTH: 409
<212> TYPE: PRT
<213> ORGANISM: Mouse

<400> SEQUENCE: 53
```

| | | | | | | | | | | | | | | |
|---|---|---|---|---|---|---|---|---|---|---|---|---|---|---|
| Met | Lys | Leu | Lys | Gln | Arg | Val | Val | Leu | Leu | Ala | Ile | Leu | Leu | Val | Ile |
| 1 | | | | 5 | | | | 10 | | | | 15 | | |
| Phe | Ile | Phe | Thr | Lys | Val | Phe | Leu | Ile | Asp | Asn | Leu | Asp | Thr | Ser | Ala |
| | | | 20 | | | | | 25 | | | | | 30 | | |
| Ala | Asn | Arg | Glu | Asp | Gln | Arg | Ala | Phe | His | Arg | Met | Met | Thr | Gly | Leu |
| | | 35 | | | | | 40 | | | | | 45 | | | |
| Arg | Val | Glu | Leu | Val | Pro | Lys | Leu | Asp | His | Thr | Leu | Gln | Ser | Pro | Trp |
| | 50 | | | | | 55 | | | | | 60 | | | | |
| Glu | Ile | Ala | Ala | Gln | Trp | Val | Val | Pro | Arg | Glu | Val | Tyr | Pro | Glu | Glu |
| 65 | | | | | 70 | | | | | 75 | | | | | 80 |
| Thr | Pro | Glu | Leu | Gly | Ala | Ile | Met | His | Ala | Met | Ala | Thr | Lys | Lys | Ile |
| | | | | 85 | | | | | 90 | | | | | 95 | |
| Ile | Lys | Ala | Asp | Val | Gly | Tyr | Lys | Gly | Thr | Gln | Leu | Lys | Ala | Leu | Leu |
| | | | 100 | | | | | 105 | | | | | 110 | | |
| Ile | Leu | Glu | Gly | Gly | Gln | Lys | Val | Val | Phe | Lys | Pro | Lys | Arg | Tyr | Ser |
| | | 115 | | | | | 120 | | | | | 125 | | | |
| Arg | Asp | Tyr | Val | Val | Glu | Gly | Glu | Pro | Tyr | Ala | Gly | Tyr | Asp | Arg | His |
| | 130 | | | | | 135 | | | | | 140 | | | | |
| Asn | Ala | Glu | Val | Ala | Ala | Phe | His | Leu | Asp | Arg | Ile | Leu | Gly | Phe | Arg |
| 145 | | | | | 150 | | | | | 155 | | | | | 160 |
| Arg | Ala | Pro | Leu | Val | Val | Gly | Arg | Tyr | Val | Asn | Leu | Arg | Thr | Glu | Val |
| | | | | 165 | | | | | 170 | | | | | 175 | |
| Lys | Pro | Val | Ala | Thr | Glu | Gln | Leu | Leu | Ser | Thr | Phe | Leu | Thr | Val | Gly |
| | | | 180 | | | | | 185 | | | | | 190 | | |
| Asn | Asn | Thr | Cys | Phe | Tyr | Gly | Lys | Cys | Tyr | Tyr | Cys | Arg | Glu | Thr | Glu |
| | | 195 | | | | | 200 | | | | | 205 | | | |
| Pro | Ala | Cys | Ala | Asp | Gly | Asp | Met | Met | Glu | Gly | Ser | Val | Thr | Leu | Trp |
| | 210 | | | | | 215 | | | | | 220 | | | | |
| Leu | Pro | Asp | Val | Trp | Pro | Leu | Gln | Lys | His | Arg | His | Pro | Trp | Gly | Arg |
| 225 | | | | | 230 | | | | | 235 | | | | | 240 |
| Thr | Tyr | Arg | Glu | Gly | Lys | Leu | Ala | Arg | Trp | Glu | Tyr | Asp | Glu | Ser | Tyr |
| | | | | 245 | | | | | 250 | | | | | 255 | |
| Cys | Asp | Ala | Val | Lys | Lys | Thr | Ser | Pro | Tyr | Asp | Ser | Gly | Pro | Arg | Leu |
| | | | 260 | | | | | 265 | | | | | 270 | | |
| Leu | Asp | Ile | Ile | Asp | Thr | Ala | Val | Phe | Asp | Tyr | Leu | Ile | Gly | Asn | Ala |
| | | 275 | | | | | 280 | | | | | 285 | | | |
| Asp | Arg | His | His | Tyr | Glu | Ser | Phe | Gln | Asp | Glu | Gly | Ala | Ser | Met |
| | 290 | | | | | 295 | | | | | 300 | | | | |
| Leu | Ile | Leu | Leu | Asp | Asn | Ala | Lys | Ser | Phe | Gly | Asn | Pro | Ser | Leu | Asp |
| 305 | | | | | 310 | | | | | 315 | | | | | 320 |
| Glu | Arg | Ser | Ile | Leu | Ala | Pro | Leu | Tyr | Gln | Cys | Cys | Ile | Ile | Arg | Val |
| | | | | 325 | | | | | 330 | | | | | 335 | |
| Ser | Thr | Trp | Asn | Arg | Leu | Asn | Tyr | Leu | Lys | Asn | Gly | Val | Leu | Lys | Ser |
| | | | 340 | | | | | 345 | | | | | 350 | | |
| Ala | Leu | Lys | Ser | Ala | Met | Ala | His | Asp | Pro | Ile | Ser | Pro | Val | Leu | Ser |
| | | 355 | | | | | 360 | | | | | 365 | | | |
| Asp | Pro | His | Leu | Asp | Thr | Val | Asp | Gln | Arg | Leu | Leu | Asn | Val | Leu | Ala |
| | 370 | | | | | 375 | | | | | 380 | | | | |
| Thr | Ile | Lys | Gln | Cys | Thr | Asp | Gln | Phe | Gly | Thr | Asp | Thr | Val | Leu | Val |

```
385                 390                 395                 400
Glu Asp Arg Met Pro Leu Ser His Leu
                405

<210> SEQ ID NO 54
<211> LENGTH: 697
<212> TYPE: PRT
<213> ORGANISM: Mouse

<400> SEQUENCE: 54

Met Arg Leu Thr Val Gly Ala Leu Leu Ala Cys Ala Ala Leu Gly Leu
 1               5                  10                  15

Cys Leu Ala Val Pro Asp Lys Thr Val Lys Trp Cys Ala Val Ser Glu
            20                  25                  30

His Glu Asn Thr Lys Cys Ile Ser Phe Arg Asp His Met Lys Thr Val
        35                  40                  45

Leu Pro Pro Asp Gly Pro Arg Leu Ala Cys Val Lys Lys Thr Ser Tyr
    50                  55                  60

Pro Asp Cys Ile Lys Ala Ile Ser Ala Ser Glu Ala Asp Ala Met Thr
65                  70                  75                  80

Leu Asp Gly Gly Trp Val Tyr Asp Ala Gly Leu Thr Pro Asn Asn Leu
                85                  90                  95

Lys Pro Val Ala Ala Glu Phe Tyr Gly Ser Val Glu His Pro Gln Thr
            100                 105                 110

Tyr Tyr Tyr Ala Val Ala Val Val Lys Lys Gly Thr Asp Phe Gln Leu
        115                 120                 125

Asn Gln Leu Glu Gly Lys Lys Ser Cys His Thr Gly Leu Gly Arg Ser
    130                 135                 140

Ala Gly Trp Val Ile Pro Ile Gly Leu Leu Phe Cys Lys Leu Ser Glu
145                 150                 155                 160

Pro Arg Ser Pro Leu Glu Lys Ala Val Ser Ser Phe Phe Ser Gly Ser
                165                 170                 175

Cys Val Pro Cys Ala Asp Pro Val Ala Phe Pro Lys Leu Cys Gln Leu
            180                 185                 190

Cys Pro Gly Cys Gly Cys Ser Ser Thr Gln Pro Phe Phe Gly Tyr Val
        195                 200                 205

Gly Ala Phe Lys Cys Leu Lys Asp Gly Gly Gly Asp Val Ala Phe Val
    210                 215                 220

Lys His Thr Thr Ile Phe Glu Val Leu Pro Glu Lys Ala Asp Arg Asp
225                 230                 235                 240

Gln Tyr Glu Leu Leu Cys Leu Asp Asn Thr Arg Lys Pro Val Asp Gln
                245                 250                 255

Tyr Glu Asp Cys Tyr Leu Ala Arg Ile Pro Ser His Ala Val Val Ala
            260                 265                 270

Arg Lys Asn Asn Gly Lys Glu Asp Leu Ile Trp Glu Ile Leu Lys Val
        275                 280                 285

Ala Gln Glu His Phe Gly Lys Gly Lys Ser Lys Asp Phe Gln Leu Phe
    290                 295                 300

Ser Ser Pro Leu Gly Lys Asp Leu Leu Phe Lys Asp Ser Ala Phe Gly
305                 310                 315                 320

Leu Leu Arg Val Pro Pro Arg Met Asp Tyr Arg Leu Tyr Leu Gly His
                325                 330                 335

Asn Tyr Val Thr Ala Ile Arg Asn Gln Gln Glu Gly Val Cys Pro Glu
            340                 345                 350
```

-continued

```
Gly Ser Ile Asp Asn Ser Pro Val Lys Trp Cys Ala Leu Ser His Leu
            355                 360                 365

Glu Arg Thr Lys Cys Asp Glu Trp Ser Ile Ile Ser Glu Gly Lys Ile
        370                 375                 380

Glu Cys Glu Ser Ala Glu Thr Thr Glu Asp Cys Ile Glu Lys Ile Val
385                 390                 395                 400

Asn Gly Glu Ala Asp Ala Met Thr Leu Asp Gly Gly His Ala Tyr Ile
                405                 410                 415

Ala Gly Gln Cys Gly Leu Val Pro Val Met Ala Glu Tyr Tyr Glu Ser
            420                 425                 430

Ser Asn Cys Ala Ile Pro Ser Gln Gln Gly Ile Phe Pro Lys Gly Tyr
        435                 440                 445

Tyr Ala Val Ala Val Val Lys Ala Ser Asp Thr Ser Ile Thr Trp Asn
    450                 455                 460

Asn Leu Lys Gly Lys Lys Ser Cys His Thr Gly Val Asp Arg Thr Ala
465                 470                 475                 480

Gly Trp Asn Ile Pro Met Gly Met Leu Tyr Asn Arg Ile Asn His Cys
                485                 490                 495

Lys Phe Asp Glu Phe Phe Ser Gln Gly Cys Ala Pro Gly Tyr Glu Lys
            500                 505                 510

Asn Ser Thr Leu Cys Asp Leu Cys Ile Gly Pro Leu Lys Cys Ala Pro
        515                 520                 525

Asn Asn Lys Glu Glu Tyr Asn Gly Tyr Thr Gly Ala Phe Arg Cys Leu
    530                 535                 540

Val Glu Lys Gly Asp Val Ala Phe Val Lys His Gln Thr Val Leu Asp
545                 550                 555                 560

Asn Thr Glu Gly Lys Asn Pro Ala Glu Trp Ala Lys Asn Leu Lys Gln
                565                 570                 575

Glu Asp Phe Glu Leu Leu Cys Pro Asp Gly Thr Arg Lys Pro Val Lys
            580                 585                 590

Asp Phe Ala Ser Cys His Leu Ala Gln Ala Pro Asn His Val Val Val
        595                 600                 605

Ser Arg Lys Glu Lys Ala Ala Arg Val Lys Ala Val Leu Thr Ser Gln
    610                 615                 620

Glu Thr Leu Phe Gly Gly Ser Asp Cys Thr Gly Asn Phe Cys Leu Phe
625                 630                 635                 640

Lys Ser Thr Thr Lys Asp Leu Leu Phe Arg Asp Asp Thr Lys Cys Phe
                645                 650                 655

Val Lys Leu Pro Glu Gly Thr Thr Pro Glu Lys Tyr Leu Gly Ala Glu
            660                 665                 670

Tyr Met Gln Ser Val Gly Asn Met Arg Lys Cys Ser Thr Ser Arg Leu
        675                 680                 685

Leu Glu Ala Cys Thr Phe His Lys His
    690                 695

<210> SEQ ID NO 55
<211> LENGTH: 400
<212> TYPE: PRT
<213> ORGANISM: Mouse

<400> SEQUENCE: 55

Gly Ala Pro Thr Pro Ala Tyr Val Arg Ser Ala Arg Arg Thr Glu Pro
1               5                   10                  15

Leu Ala Ser Gly Ala Arg Ser Arg Leu Cys Gln Cys Arg Arg Val Pro
            20                  25                  30
```

-continued

```
Ala Arg Lys Gln Gly Pro Gln Gln Gly Ser Gly Glu Ser Thr
        35                  40              45

Thr Ser Ser Pro Gln Trp Trp Arg Arg Trp Arg Leu Trp Ser Thr
 50                  55                  60

Cys Ser Cys Ser Ala Asp Asp Arg His Thr Gly Ser His Thr Asp Leu
65                   70                  75                  80

Lys Glu Glu Thr Pro Ser Trp Thr Gln Ile Ser Val Val Phe Arg Lys
                 85                  90                  95

Asp Gly Gln Asp Glu Leu Gln Ala Ala His Lys Ala His Gly Ser Gly
             100                 105                 110

Ser Pro Leu Thr Asn Gln Glu Ile Pro Ser Ser Ser Gly Ser Gly Phe
         115                 120                 125

Ile Val Ser Glu Asp Gly Leu Ile Val Thr Asn Ala His Val Leu Thr
     130                 135                 140

Asn Gln Gln Lys Ile Gln Val Glu Leu Gln Ser Gly Ala Arg Tyr Glu
145                 150                 155                 160

Ala Thr Val Lys Asp Ile Asp His Lys Leu Asp Leu Ala Leu Ile Lys
                 165                 170                 175

Ile Glu Pro Asp Thr Glu Leu Pro Val Leu Leu Gly Arg Ser Ser
             180                 185                 190

Asp Leu Arg Ala Gly Glu Phe Val Val Ala Leu Gly Ser Pro Phe Ser
         195                 200                 205

Leu Gln Asn Thr Val Thr Ala Gly Ile Val Ser Thr Thr Gln Arg Gly
     210                 215                 220

Gly Arg Glu Leu Gly Leu Lys Asn Ser Asp Ile Asp Tyr Ile Gln Thr
225                 230                 235                 240

Asp Ala Ile Ile Asn His Gly Asn Ser Gly Gly Pro Leu Val Asn Leu
                 245                 250                 255

Asp Gly Asp Val Ile Gly Ile Asn Thr Leu Lys Val Thr Ala Gly Ile
             260                 265                 270

Ser Phe Ala Ile Pro Ser Asp Arg Ile Arg Gln Phe Leu Glu Asp Tyr
         275                 280                 285

His Glu Arg Gln Leu Lys Gly Lys Ala Pro Leu Gln Lys Lys Tyr Leu
     290                 295                 300

Gly Leu Arg Met Leu Pro Leu Thr Leu Asn Leu Leu Gln Glu Met Lys
305                 310                 315                 320

Arg Gln Asp Pro Glu Phe Pro Asp Val Ser Ser Gly Val Phe Val Tyr
                 325                 330                 335

Glu Val Ile Gln Gly Ser Ala Ala Ser Ser Gly Leu Arg Asp His
             340                 345                 350

Asp Val Ile Val Ser Ile Asn Gly Gln Pro Val Thr Thr Thr Asp
         355                 360                 365

Val Ile Glu Ala Val Lys Asp Asn Asp Phe Leu Ser Ile Ile Val Leu
     370                 375                 380

Arg Gly Ser Gln Thr Leu Phe Leu Thr Val Thr Pro Glu Ile Ile Asn
385                 390                 395                 400
```

<210> SEQ ID NO 56
<211> LENGTH: 174
<212> TYPE: PRT
<213> ORGANISM: Mouse

<400> SEQUENCE: 56

Met Pro Ala Cys Arg Leu Cys Leu Leu Ala Ala Gly Leu Leu Leu Gly

-continued

```
                1               5                       10                      15
        Leu     Leu     Leu     Phe     Thr     Pro     Ile     Ser     Ala     Thr     Gly     Thr     Asp     Ala     Glu     Lys
                                        20                              25                              30

Pro     Gly     Glu     Cys     Pro     Gln     Leu     Glu     Pro     Ile     Thr     Asp     Cys     Val     Leu     Glu
                                35                              40                              45

Cys     Thr     Leu     Asp     Lys     Asp     Cys     Ala     Asp     Asn     Arg     Lys     Cys     Cys     Gln     Ala
                50                              55                              60

Gly     Cys     Ser     Ser     Val     Cys     Ser     Lys     Pro     Asn     Gly     Pro     Ser     Glu     Gly     Glu
        65                              70                              75                                              80

Leu     Ser     Gly     Thr     Asp     Thr     Lys     Leu     Ser     Glu     Thr     Gly     Thr     Thr     Thr     Gln
                                        85                              90                              95

Ser     Ala     Gly     Leu     Asp     His     Thr     Thr     Lys     Pro     Pro     Gly     Gly     Gln     Val     Ser
                                100                             105                             110

Thr     Lys     Pro     Pro     Ala     Val     Thr     Arg     Glu     Gly     Leu     Gly     Val     Arg     Glu     Lys
                                115                             120                             125

Gln     Gly     Thr     Cys     Pro     Ser     Val     Asp     Ile     Pro     Lys     Leu     Gly     Leu     Cys     Glu
                                130                             135                             140

Asp     Gln     Cys     Gln     Val     Asp     Ser     Gln     Cys     Ser     Gly     Asn     Met     Lys     Cys     Cys
        145                             150                             155                                             160

Arg     Asn     Gly     Cys     Gly     Lys     Met     Ala     Cys     Thr     Thr     Pro     Lys     Phe
                                        165                             170
```

<210> SEQ ID NO 57
<211> LENGTH: 173
<212> TYPE: PRT
<213> ORGANISM: Mouse

<400> SEQUENCE: 57

```
        Val     Arg     Asn     Gly     Asp     Leu     Phe     Phe     Lys     Lys     Val     Gln     Val     Glu     Asp     Gly
        1                               5                               10                                              15

Gly     Val     Tyr     Thr     Cys     Tyr     Ala     Met     Gly     Glu     Thr     Phe     Asn     Glu     Thr     Leu
                                        20                              25                              30

Ser     Val     Glu     Leu     Lys     Val     Tyr     Asn     Phe     Thr     Leu     His     Gly     His     His     Asp
                                35                              40                              45

Thr     Leu     Asn     Thr     Ala     Tyr     Thr     Thr     Leu     Val     Gly     Cys     Ile     Leu     Ser     Val
                50                              55                              60

Val     Leu     Val     Leu     Ile     Tyr     Leu     Tyr     Leu     Thr     Pro     Cys     Arg     Cys     Trp     Cys
        65                              70                              75                                              80

Arg     Gly     Val     Glu     Lys     Pro     Ser     Ser     His     Gln     Gly     Asp     Ser     Leu     Ser     Ser
                                        85                              90                              95

Ser     Met     Leu     Ser     Thr     Thr     Pro     Asn     His     Asp     Pro     Met     Ala     Gly     Gly     Asp
                                100                             105                             110

Lys     Asp     Asp     Gly     Phe     Asp     Arg     Arg     Val     Ala     Phe     Leu     Glu     Pro     Ala     Gly
                                115                             120                             125

Pro     Gly     Gln     Gly     Gln     Asn     Gly     Lys     Leu     Lys     Pro     Gly     Asn     Thr     Leu     Pro
                                130                             135                             140

Val     Pro     Glu     Ala     Thr     Gly     Lys     Gly     Gln     Arg     Arg     Met     Ser     Asp     Pro     Glu
        145                             150                             155                                             160

Ser     Val     Ser     Ser     Val     Phe     Ser     Asp     Thr     Pro     Ile     Val     Val
                                        165                             170
```

<210> SEQ ID NO 58
<211> LENGTH: 88
<212> TYPE: PRT
<213> ORGANISM: Mouse

```
<400> SEQUENCE: 58

Met Glu Glu Ile Thr Cys Ala Phe Leu Leu Leu Ala Gly Leu Pro
  1               5                  10                  15

Ala Leu Glu Ala Ser Asp Pro Val Asp Lys Asp Ser Pro Phe Tyr Tyr
                 20                  25                  30

Asp Trp Glu Ser Leu Gln Leu Gly Gly Leu Ile Phe Gly Gly Leu Leu
             35                  40                  45

Cys Ile Ala Gly Ile Ala Met Ala Leu Ser Gly Lys Cys Lys Cys Arg
         50                  55                  60

Arg Thr His Lys Pro Ser Ser Leu Pro Gly Lys Ala Thr Pro Leu Ile
 65                  70                  75                  80

Ile Pro Gly Ser Ala Asn Thr Cys
                 85

<210> SEQ ID NO 59
<211> LENGTH: 171
<212> TYPE: PRT
<213> ORGANISM: Mouse

<400> SEQUENCE: 59

Leu Ser Val Val Leu Gly Gly Thr Leu Tyr Ile Gly His Tyr Leu Ala
  1               5                  10                  15

Met Tyr Ser Glu Gly Ala Pro Phe Trp Thr Gly Ile Val Ala Met Leu
                 20                  25                  30

Ala Gly Ala Val Ala Phe Leu His Lys Lys Arg Gly Gly Thr Cys Trp
             35                  40                  45

Ala Leu Met Arg Thr Leu Leu Val Leu Ala Ser Phe Cys Thr Ala Val
         50                  55                  60

Ala Ala Ile Val Ile Gly Ser Arg Glu Leu Asn Tyr Tyr Trp Tyr Phe
 65                  70                  75                  80

Leu Gly Asp Asp Val Cys Gln Arg Asp Ser Ser Tyr Gly Trp Ser Thr
                 85                  90                  95

Met Pro Arg Thr Thr Pro Val Pro Glu Glu Ala Asp Arg Ile Ala Leu
            100                 105                 110

Cys Ile Tyr Tyr Thr Ser Met Leu Lys Thr Leu Leu Met Ser Leu Gln
        115                 120                 125

Ala Met Leu Leu Gly Ile Trp Val Leu Leu Leu Ala Ser Leu Thr
    130                 135                 140

Pro Val Cys Val Tyr Ile Trp Lys Arg Phe Phe Thr Lys Ala Glu Thr
145                 150                 155                 160

Glu Glu Lys Lys Leu Leu Gly Ala Ala Val Ile
                165                 170

<210> SEQ ID NO 60
<211> LENGTH: 318
<212> TYPE: PRT
<213> ORGANISM: Mouse

<400> SEQUENCE: 60

Met Leu Gln His Thr Ser Leu Val Leu Leu Leu Ala Ser Ile Trp Thr
  1               5                  10                  15

Thr Arg His Pro Val Gln Gly Ala Asp Leu Val Gln Asp Leu Ser Ile
                 20                  25                  30

Ser Thr Cys Arg Ile Met Gly Val Ala Leu Val Gly Arg Asn Lys Asn
             35                  40                  45

Pro Gln Met Asn Phe Thr Glu Ala Asn Glu Ala Cys Lys Met Leu Gly
```

-continued

```
            50                  55                  60
Leu Thr Leu Ala Ser Arg Asp Gln Val Glu Ser Ala Gln Lys Ser Gly
 65                  70                  75                  80

Phe Glu Thr Cys Ser Tyr Gly Trp Val Gly Glu Gln Phe Ser Val Ile
                 85                  90                  95

Pro Arg Ile Phe Ser Asn Pro Arg Cys Gly Lys Asn Gly Lys Gly Val
            100                 105                 110

Leu Ile Trp Asn Ala Pro Ser Ser Gln Lys Phe Lys Ala Tyr Cys His
        115                 120                 125

Asn Ser Ser Asp Thr Trp Val Asn Ser Cys Ile Pro Glu Ile Val Thr
130                 135                 140

Thr Phe Tyr Pro Val Leu Asp Thr Gln Thr Pro Ala Thr Glu Phe Ser
145                 150                 155                 160

Val Ser Ser Ser Ala Tyr Leu Ala Ser Ser Pro Asp Ser Thr Thr Pro
                165                 170                 175

Val Ser Ala Thr Thr Arg Ala Pro Pro Leu Thr Ser Met Ala Arg Lys
            180                 185                 190

Thr Lys Lys Ile Cys Ile Thr Glu Val Tyr Thr Glu Pro Ile Thr Met
        195                 200                 205

Ala Thr Glu Thr Glu Ala Phe Val Ala Ser Gly Ala Ala Phe Lys Asn
210                 215                 220

Glu Ala Gly Phe Gly Gly Val Pro Thr Ala Leu Leu Val Leu Ala
225                 230                 235                 240

Leu Leu Phe Phe Gly Ala Ala Val Leu Ala Val Cys Tyr Val Lys
                245                 250                 255

Arg Tyr Val Lys Ala Phe Pro Phe Thr Thr Lys Asn Gln Gln Lys Glu
            260                 265                 270

Met Ile Glu Thr Lys Val Val Lys Glu Glu Lys Ala Asp Asp Val Asn
        275                 280                 285

Ala Asn Glu Glu Ser Lys Lys Thr Ile Lys Asn Pro Glu Glu Ala Lys
290                 295                 300

Ser Pro Pro Lys Thr Thr Val Arg Cys Leu Glu Ala Glu Val
305                 310                 315

<210> SEQ ID NO 61
<211> LENGTH: 93
<212> TYPE: PRT
<213> ORGANISM: Mouse

<400> SEQUENCE: 61

Ala His Met Val Trp Ala Asn Leu Ala Val Phe Val Ile Cys Phe Leu
  1               5                  10                  15

Pro Leu His Val Val Leu Thr Val Gln Val Ser Leu Asn Leu Asn Thr
             20                  25                  30

Cys Ala Ala Arg Asp Thr Phe Ser Arg Ala Leu Ser Ile Thr Gly Lys
         35                  40                  45

Leu Ser Asp Thr Asn Cys Cys Leu Asp Ala Ile Cys Tyr Tyr Tyr Met
 50                  55                  60

Ala Arg Glu Phe Gln Glu Ala Ser Lys Pro Ala Thr Ser Ser Asn Thr
 65                  70                  75                  80

Pro His Lys Ser Gln Asp Ser Gln Ile Leu Ser Leu Thr
                 85                  90

<210> SEQ ID NO 62
<211> LENGTH: 408
```

-continued

```
<212> TYPE: PRT
<213> ORGANISM: Mouse

<400> SEQUENCE: 62

Met Ala Gln Leu Ala Arg Ala Thr Arg Ser Pro Leu Ser Trp Leu Leu
 1               5                  10                  15

Leu Leu Phe Cys Tyr Ala Leu Arg Lys Ala Gly Gly Asp Ile Arg Val
             20                  25                  30

Leu Val Pro Tyr Asn Ser Thr Gly Val Leu Gly Gly Ser Thr Thr Leu
             35                  40                  45

His Cys Ser Leu Thr Ser Asn Glu Asn Val Thr Ile Thr Gln Ile Thr
     50                  55                  60

Trp Met Lys Lys Asp Ser Gly Ser His Ala Leu Val Ala Val Phe
 65                  70                  75                  80

His Pro Lys Lys Gly Pro Asn Ile Lys Glu Pro Glu Arg Val Lys Phe
                 85                  90                  95

Leu Ala Ala Gln Gln Asp Leu Arg Asn Ala Ser Leu Ala Ile Ser Asn
                100                 105                 110

Leu Ser Val Glu Asp Glu Gly Ile Tyr Glu Cys Gln Ile Ala Thr Phe
            115                 120                 125

Pro Arg Gly Ser Arg Ser Thr Asn Ala Trp Leu Lys Val Gln Ala Arg
        130                 135                 140

Pro Lys Asn Thr Ala Glu Ala Leu Glu Pro Ser Pro Thr Leu Ile Leu
145                 150                 155                 160

Gln Asp Val Ala Lys Cys Ile Ser Ala Asn Gly His Pro Pro Gly Arg
                165                 170                 175

Ile Ser Trp Pro Ser Asn Val Asn Gly Ser His Arg Glu Met Lys Glu
            180                 185                 190

Pro Gly Ser Gln Pro Gly Thr Thr Thr Val Thr Ser Tyr Leu Ser Met
        195                 200                 205

Val Pro Ser Arg Gln Ala Asp Gly Lys Asn Ile Thr Cys Thr Val Glu
    210                 215                 220

His Glu Ser Leu Gln Glu Leu Asp Gln Leu Leu Val Thr Leu Ser Gln
225                 230                 235                 240

Pro Tyr Pro Pro Glu Asn Val Ser Ile Ser Gly Tyr Asp Gly Asn Trp
                245                 250                 255

Tyr Val Gly Leu Thr Asn Leu Thr Leu Thr Cys Glu Ala His Ser Lys
            260                 265                 270

Pro Ala Pro Asp Met Ala Gly Tyr Asn Trp Ser Thr Asn Thr Gly Asp
        275                 280                 285

Phe Pro Asn Ser Val Lys Arg Gln Gly Asn Met Leu Leu Ile Ser Thr
    290                 295                 300

Val Glu Asp Gly Leu Asn Asn Thr Val Ile Val Cys Glu Val Thr Asn
305                 310                 315                 320

Ala Leu Gly Ser Gly Gln Gly Gln Val His Ile Ile Val Lys Glu Lys
                325                 330                 335

Pro Glu Asn Met Gln Gln Asn Thr Arg Leu His Leu Gly Tyr Ile Phe
            340                 345                 350

Leu Ile Val Phe Val Leu Ala Val Val Ile Ile Ala Ala Leu Tyr
        355                 360                 365

Thr Ile Arg Arg Cys Arg His Gly Arg Ala Leu Gln Ser Asn Pro Ser
    370                 375                 380

Glu Arg Glu Asn Val Gln Tyr Ser Ser Val Asn Gly Asp Cys Arg Leu
385                 390                 395                 400
```

Asn Met Glu Pro Asn Ser Thr Arg
                405

<210> SEQ ID NO 63
<211> LENGTH: 278
<212> TYPE: PRT
<213> ORGANISM: Mouse

<400> SEQUENCE: 63

Met Phe Leu Val Gly Ser Leu Val Val Leu Cys Gly Leu Leu Ala His
1               5                   10                  15

Ser Thr Ala Gln Leu Ala Gly Leu Pro Leu Pro Leu Gly Gln Gly Pro
            20                  25                  30

Pro Leu Pro Leu Asn Gln Gly Pro Leu Pro Leu Asn Gln Gly Gln
        35                  40                  45

Leu Leu Pro Leu Ala Gln Gly Leu Pro Leu Ala Val Ser Pro Ala Leu
        50                  55                  60

Pro Ser Asn Pro Thr Asp Leu Leu Ala Gly Lys Phe Thr Asp Ala Leu
65                  70                  75                  80

Ser Gly Gly Leu Leu Ser Gly Gly Leu Leu Gly Ile Leu Glu Asn Ile
                85                  90                  95

Pro Leu Leu Asp Val Ile Lys Ser Gly Gly Asn Ser Asn Gly Leu
            100                 105                 110

Val Gly Gly Leu Leu Gly Lys Leu Thr Ser Ser Val Pro Leu Leu Asn
            115                 120                 125

Asn Ile Leu Asp Ile Lys Ile Thr Asp Pro Gln Leu Leu Glu Leu Gly
        130                 135                 140

Leu Val Gln Ser Pro Asp Gly His Arg Leu Tyr Val Thr Ile Pro Leu
145                 150                 155                 160

Gly Leu Thr Leu Asn Val Asn Met Pro Val Val Gly Ser Leu Leu Gln
                165                 170                 175

Leu Ala Val Lys Leu Asn Ile Thr Ala Glu Val Leu Ala Val Lys Asp
                180                 185                 190

Asn Gln Gly Arg Ile His Leu Val Leu Gly Asp Cys Thr His Ser Pro
            195                 200                 205

Gly Ser Leu Lys Ile Ser Leu Leu Asn Gly Val Thr Pro Val Gln Ser
        210                 215                 220

Phe Leu Asp Asn Leu Thr Gly Ile Leu Thr Lys Val Leu Pro Glu Leu
225                 230                 235                 240

Ile Gln Gly Lys Val Cys Pro Leu Val Asn Gly Ile Leu Ser Gly Leu
                245                 250                 255

Asp Val Thr Leu Val His Asn Ile Ala Glu Leu Leu Ile His Gly Leu
                260                 265                 270

Gln Phe Val Ile Lys Val
        275

<210> SEQ ID NO 64
<211> LENGTH: 264
<212> TYPE: PRT
<213> ORGANISM: Mouse

<400> SEQUENCE: 64

Met Ala Thr Thr Thr Cys Gln Val Val Gly Leu Leu Leu Ser Leu Leu
1               5                   10                  15

Gly Leu Ala Gly Cys Ile Ala Ala Thr Gly Met Asp Met Trp Ser Thr
            20                  25                  30

-continued

Gln Asp Leu Tyr Asp Asn Pro Val Thr Ala Val Phe Gln His Glu Gly
         35                  40                  45

Leu Trp Arg Ser Cys Val Gln Gln Ser Ser Gly Phe Thr Glu Cys Arg
 50                  55                  60

Pro Tyr Phe Thr Ile Leu Gly Leu Pro Ala Met Leu Gln Ala Val Arg
65              70                  75                  80

Ala Leu Met Ile Val Gly Ile Val Leu Gly Val Ile Gly Ile Leu Val
             85                  90                  95

Ser Ile Phe Ala Leu Lys Cys Ile Arg Ile Gly Ser Met Asp Asp Ser
            100                 105                 110

Ala Lys Ala Lys Met Thr Leu Thr Ser Gly Ile Leu Phe Ile Ile Ser
            115                 120                 125

Gly Ile Cys Ala Ile Ile Gly Val Ser Val Phe Ala Asn Met Leu Val
            130                 135                 140

Thr Asn Phe Trp Met Ser Thr Ala Asn Met Tyr Ser Gly Met Gly Gly
145                 150                 155                 160

Met Gly Gly Met Val Gln Thr Val Gln Thr Arg Tyr Thr Phe Gly Ala
                165                 170                 175

Ala Leu Phe Val Gly Trp Val Ala Gly Gly Leu Thr Leu Ile Gly Gly
                180                 185                 190

Val Met Met Cys Ile Ala Cys Arg Gly Leu Thr Pro Asp Asp Ser Asn
                195                 200                 205

Phe Lys Ala Val Ser Tyr His Ala Ser Gly Gln Asn Val Ala Tyr Arg
                210                 215                 220

Pro Gly Gly Phe Lys Ala Ser Thr Gly Phe Gly Ser Asn Thr Arg Asn
225                 230                 235                 240

Lys Lys Ile Tyr Asp Gly Gly Ala Arg Thr Glu Asp Asp Glu Gln Ser
                245                 250                 255

His Pro Thr Lys Tyr Asp Tyr Val
            260

<210> SEQ ID NO 65
<211> LENGTH: 132
<212> TYPE: PRT
<213> ORGANISM: Mouse

<400> SEQUENCE: 65

Ala His Pro Arg Pro Gly Ala Arg Arg Pro Arg Leu Leu Ala Phe Gln
 1               5                  10                  15

Ala Ser Cys Ala Pro Ala Pro Gly Ser Arg Asp Arg Cys Pro Glu Glu
             20                  25                  30

Gly Gly Pro Arg Cys Leu Arg Val Tyr Ala Gly Leu Ile Gly Thr Val
             35                  40                  45

Val Thr Pro Asn Tyr Leu Asp Asn Val Ser Ala Arg Val Ala Pro Trp
         50                  55                  60

Cys Gly Cys Ala Ala Ser Gly Asn Arg Arg Glu Glu Cys Glu Ala Phe
65                  70                  75                  80

Arg Lys Leu Phe Thr Arg Asn Pro Cys Leu Asp Gly Ala Ile Gln Ala
                 85                  90                  95

Phe Asp Ser Leu Gln Pro Ser Val Leu Gln Asp Gln Thr Ala Gly Cys
            100                 105                 110

Cys Phe Pro Arg Val Ser Trp Leu Tyr Ala Leu Thr Ala Leu Ala Leu
            115                 120                 125

Gln Ala Leu Leu

<210> SEQ ID NO 66
<211> LENGTH: 764
<212> TYPE: DNA
<213> ORGANISM: Mouse

<400> SEQUENCE: 66

```
gcagcaccca gcgccaagcg caccaggcac cgcgacagac ggcaggagca cccatcgacg      60
ggcgtactgg agcgagccga gcagagcaga gagaggcgtg cttgaaaccg agaaccaagc     120
cgggcggcat cccccggccg ccgcacgcac aggccggcgc cctccttgcc tccctgctcc     180
ccaccgcgcc cctccggcca gcatgaggct cctggcggcc gcgctgctcc tgctgctcct     240
ggcgctgtgc gcctcgcgcg tggacgggtc caagtgtaag tgttcccgga aggggcccaa     300
gatccgctac agcgacgtga agaagctgga aatgaagcca agtaccac actgcgagga      360
gaagatggtt atcgtcacca ccaagagcat gtccaggtac cggggccagg agcactgcct     420
gcaccctaag ctgcagagca ccaaacgctt catcaagtgg tacaatgcct ggaacgagaa     480
gcgcagggtc tacgaagaat agggtggacg atcatggaaa gaaaaactcc aggccagttg     540
agagacttca gcagaggact ttgcagatta aataaaagc cctttcttc tcacaagcat      600
aagacaaatt atatattgct atgaagctct tcttaccagg gtcagttttt acattttata     660
gctgtgtgtg aaaggcttcc agatgtgaga tccagctcgc ctgcgcacca gacttcatta     720
caagtggctt tttgctgggc ggttggcggg gggcgggggg acct                      764
```

<210> SEQ ID NO 67
<211> LENGTH: 288
<212> TYPE: DNA
<213> ORGANISM: Human

<400> SEQUENCE: 67

```
gcggccgcgc tgctcctgct gctgctggcg ctgtacaccg cgcgtgtgga cgggtccaaa      60
tgcaagtgct cccggaaggg acccaagatc cgctacagca cgtgaagaa gctggaaatg     120
aagccaaagt acccgcactg cgaggagaag atggttatca tcaccaccaa gagcgtgtcc     180
aggtaccgag gtcaggagca ctgcctgcac cccaagctgc agagcaccaa gcgcttcatc     240
aagtggtaca acgcctggaa cgagaagcgc agggtctacg aagaatag                  288
```

<210> SEQ ID NO 68
<211> LENGTH: 95
<212> TYPE: PRT
<213> ORGANISM: Human

<400> SEQUENCE: 68

```
Ala Ala Ala Leu Leu Leu Leu Leu Ala Leu Tyr Thr Ala Arg Val
 1               5                  10                  15

Asp Gly Ser Lys Cys Lys Cys Ser Arg Lys Gly Pro Lys Ile Arg Tyr
            20                  25                  30

Ser Asp Val Lys Lys Leu Glu Met Lys Pro Lys Tyr Pro His Cys Glu
        35                  40                  45

Glu Lys Met Val Ile Ile Thr Thr Lys Ser Val Ser Arg Tyr Arg Gly
    50                  55                  60

Gln Glu His Cys Leu His Pro Lys Leu Gln Ser Thr Lys Arg Phe Ile
65                  70                  75                  80

Lys Trp Tyr Asn Ala Trp Asn Glu Lys Arg Val Tyr Glu Glu
                85                  90                  95
```

<210> SEQ ID NO 69
<211> LENGTH: 234
<212> TYPE: DNA
<213> ORGANISM: Mouse

<400> SEQUENCE: 69

```
tccaagtgta agtgttcccg aaggggccc  aagatccgct acagcgacgt gaagaagctg    60
gaaatgaagc caaagtaccc acactgcgag gagaagatgg ttatcgtcac caccaagagc   120
atgtccaggt accggggcca ggagcactgc ctgcacccta agctgcagag caccaaacgc   180
ttcatcaagt ggtacaatgc ctggaacgag aagcgcaggg tctacgaaga atag          234
```

<210> SEQ ID NO 70
<211> LENGTH: 77
<212> TYPE: PRT
<213> ORGANISM: Mouse

<400> SEQUENCE: 70

Ser Lys Cys Lys Cys Ser Arg Lys Gly Pro Lys Ile Arg Tyr Ser Asp
 1               5                  10                  15

Val Lys Lys Leu Glu Met Lys Pro Lys Tyr Pro His Cys Glu Glu Lys
            20                  25                  30

Met Val Ile Val Thr Thr Lys Ser Met Ser Arg Tyr Arg Gly Gln Glu
        35                  40                  45

His Cys Leu His Pro Lys Leu Gln Ser Thr Lys Arg Phe Ile Lys Trp
    50                  55                  60

Tyr Asn Ala Trp Asn Glu Lys Arg Arg Val Tyr Glu Glu
65                  70                  75

<210> SEQ ID NO 71
<211> LENGTH: 234
<212> TYPE: DNA
<213> ORGANISM: Human

<400> SEQUENCE: 71

```
tccaaatgca agtgctcccg aagggaccc  aagatccgct acagcgacgt gaagaagctg    60
gaaatgaagc caaagtaccc gcactgcgag gagaagatgg ttatcatcac caccaagagc   120
gtgtccaggt accgaggtca ggagcactgc ctgcacccca agctgcagag caccaagcgc   180
ttcatcaagt ggtacaacgc ctggaacgag aagcgcaggg tctacgaaga atag          234
```

<210> SEQ ID NO 72
<211> LENGTH: 77
<212> TYPE: PRT
<213> ORGANISM: Human

<400> SEQUENCE: 72

Ser Lys Cys Lys Cys Ser Arg Lys Gly Pro Lys Ile Arg Tyr Ser Asp
 1               5                  10                  15

Val Lys Lys Leu Glu Met Lys Pro Lys Tyr Pro His Cys Glu Glu Lys
            20                  25                  30

Met Val Ile Ile Thr Thr Lys Ser Val Ser Arg Tyr Arg Gly Gln Glu
        35                  40                  45

His Cys Leu His Pro Lys Leu Gln Ser Thr Lys Arg Phe Ile Lys Trp
    50                  55                  60

Tyr Asn Ala Trp Asn Glu Lys Arg Arg Val Tyr Glu Glu
65                  70                  75

POLYNUCLEOTIDES, POLYPEPTIDES EXPRESSED BY THE POLYNUCLEOTIDES AND METHODS FOR THEIR USE

CROSS-REFERENCE TO RELATED APPLICATION

This application claims priority under 35 U.S.C. 119(e) to U.S. Provisional Patent Application No. 60/171,678 filed Dec. 22, 1999.

TECHNICAL FIELD OF THE INVENTION

This invention relates to polynucleotides believed to be novel, including partial, extended and full length sequences, as well as probes and primers, genetic constructs comprising the polynucleotides, biological materials incorporating the polynucleotides, polypeptides expressed by the polynucleotides, and methods for using the polynucleotides and polypeptides.

BACKGROUND OF THE INVENTION

Sequencing of the genomes, or portions of the genomes, of numerous biological materials, including humans, animals, microorganisms and various plant varieties, has been and is being carried out on a large scale. Polynucleotides identified using sequencing techniques may be partial or full-length genes, and may contain open reading frames, or portions of open reading frames, that encode polypeptides. Putative polypeptides may be determined based on polynucleotide sequences. The sequencing data relating to polynucleotides thus represents valuable and useful information.

Polynucleotides may be analyzed for various degrees of novelty by comparing identified sequences to sequences published in various public domain databases, such as EMBL. Newly identified polynucleotides and putative polypeptides may also be compared to polynucleotides and polypeptides contained in public domain information to ascertain homology to known polynucleotides and polypeptides. In this way, the degree of similarity, identity or homology of polynucleotides and polypeptides of unknown function may be determined relative to polynucleotides and polypeptides having known functions.

Information relating to the sequences of isolated polynucleotides may be used in a variety of ways. Specified polynucleotides having a particular sequence may be isolated, or synthesized, for use in in vivo or in vitro experimentation as probes or primers. Alternatively, collections of sequences of isolated polynucleotides may be stored using magnetic or optical storage medium, and analyzed or manipulated using computer hardware and software, as well as other types of tools.

SUMMARY OF THE INVENTION

The present invention relates to polynucleotide sequences identified in the attached Sequence Listing as SEQ ID NOS: 1–35, variants of those sequences, extended sequences comprising the sequences set out in SEQ ID NOS: 1–35 and their variants, probes and primers corresponding to the sequences set out in SEQ ID NOS: 1–35 and their variants, polynucleotides comprising at least a specified number of contiguous residues of any of the polynucleotides identified as SEQ ID NOS: 1–35 (x-mers), and extended sequences comprising portions of the sequences set out in SEQ ID NOS: 1–35, all of which are referred to herein, collectively, as "polynucleotides of the present invention."

The polynucleotide sequences identified as SEQ ID NOS: 1–35 were derived from mammalian sources, namely, from mouse airways induced eosinophilia, rat dermal papilla and mouse stromal cells. Some of the polynucleotides of the present invention are "partial" sequences, in that they do not represent a full-length gene encoding a full-length polypeptide. Such partial sequences may be extended by further analyzing and sequencing the EST clones from which the sequences were obtained, or by analyzing and sequencing various DNA libraries (e.g. cDNA or genoiic) using primers and/or probes and well known hybridization and/or PCR techniques. The partial sequences identified as SEQ ID NOS: 1–35 may thus be extended until an open reading frame encoding a polypeptide, a full-length polynucleotide and/or gene capable of expressing a polypeptide, or another useful portion of the genome is identified. Such extended sequences, including full-length polynucleotides and genes, are described as "corresponding to" a sequence identified as one of the sequences of SEQ ID NOS: 1–35 or a variant thereof, or a portion of one of the sequences of SEQ ID NOS: 1–35 or a variant thereof, when the extended polynucleotide comprises an identified sequence or its variant, or an identified contiguous portion (x-mer) of one of the sequences of SEQ ID NOS: 1–35 or a variant thereof.

The polynucleotides identified as SEQ ID NOS: 1–35 were isolated from mouse and rat cDNA clones and represent sequences that are expressed in the tissue from which the cDNA was prepared. The sequence information may be used to isolate or synthesize expressible DNA molecules, such as open reading frames or fall-length genes, that can then be used as expressible or otherwise functional DNA in transgenic mammals and other organisms. Similarly, RNA sequences, reverse sequences, complementary sequences, anti-sense sequences and the like, corresponding to the polynucleotides of the present invention, may be routinely ascertained and obtained using the cDNA sequences identified as SEQ ID NOS: 1–35.

In a first aspect, the present invention provides isolated polynucleotide sequences comprising a polynucleotide selected from the group consisting of: (a) sequences recited in SEQ ID NO: 1–35; (b) complements of the sequences recited in SEQ ED NO: 1–35; (c) reverse complements of the sequences recited in SEQ ID NO: 1–35; (d) reverse sequences of the sequences recited in SEQ ID NO: 1–35; (e) sequences having either 40%, 60%, 75% or 90% identical nucleotides, as defined herein, to a sequence of (a)–(d); probes and primers corresponding to the sequences set out in SEQ ID NO: 1–35; polynucleotides comprising at least a specified number of contiguous residues of any of the polynucleotides identified as SEQ ID NO: 1–35; and extended sequences comprising portions of the sequences set out in SEQ ID NO: 1–35; all of which are referred to herein as "polynucleotides of the present invention". The present invention also provides isolated polypeptide sequences identified in the attached Sequence Listing as SEQ ID NO: 36–65; polypeptide variants of those sequences; and polypeptides comprising the isolated polypeptide sequences and variants of those sequences.

In another aspect, the present invention provides genetic constructs comprising a polynucleotide of the present invention, either alone, or in combination with one or more additional polynucleotides of the present invention, or in combination with one or more known polynucleotides, together with cells and target organisms comprising such constructs.

The polynucleotides identified as SEQ ID NOS: 1–35 may contain open reading frames ("ORFs") or partial open reading frames encoding polypeptides. Additionally, open reading frames encoding polypeptides may be identified in extended or full-length sequences corresponding to the sequences set out as SEQ ID NOS: 1–35. Open reading frames may be identified using techniques that are well known in the art. These techniques include, for example, analysis for the location of known start and stop codons, most likely reading frame identification based on codon frequencies, etc. Suitable tools and software for ORF analysis are available, for example, on the Internet. Open reading frames and portions of open reading frames may be identified in the polynucleotides of the present invention. Once a partial open reading frame is identified, the polynucleotide may be extended in the area of the partial open reading frame using techniques that are well known in the art until the polynucleotide for the fall open reading frame is identified. Thus, polynucleotides and open reading frames encoding polypeptides may be identified using the polynucleotides of the present invention.

Once open reading frames are identified in the polynucleotides of the present invention, the open reading frames may be isolated and/or synthesized. Expressible DNA constructs may then be constructed that comprise the open reading frames and suitable promoters, initiators, terminators, etc., which are well known in the art. Such DNA constructs may be introduced into a host cell to express the polypeptide encoded by the open reading frame. Suitable host cells may include various prokaryotic and eukaryotic cells.

Polypeptides encoded by the polynucleotides of the present invention may be expressed and used in various assays to determine their biological activity. Such polypeptides may be used to raise antibodies, to isolate corresponding interacting proteins or other compounds, and to quantitatively determine levels of interacting proteins or other compounds.

In another aspect, the present invention provides isolated polypeptides encoded, or partially encoded, by the above polynucleotides. As used herein, the term "polypeptide" encompasses amino acid chains of any length including full-length proteins, wherein the amino acid residues are linked by covalent peptide bonds. The term "polypeptide encoded by a polynucleotide" as used herein, includes polypeptides encoded by a polynucleotide that comprises an isolated polynucleotide sequence or variant provided herein. Polypeptides of the present invention may be naturally purified products, or may be produced partially or wholly using recombinant techniques. Such polypeptides may be glycosylated with bacterial, fungal, mammalian or other eukaryotic carbohydrates or may be non-glycosylated. In specific embodiments, the inventive polypeptides comprise an amino acid sequence selected from the group consisting of SEQ ID NO: 36–65.

Polypeptides of the present invention may be produced recombinantly by inserting a polynucleotide sequence that encodes the polypeptide into a genetic construct and expressing the polypeptide in an appropriate host. Any of a variety of genetic constructs known to those of ordinary skill in the art may be employed. Expression may be achieved in any appropriate host cell that has been transformed or transfected with a genetic construct containing a polynucleotide that encodes a recombinant polypeptide. Suitable host cells include prokaryotes, yeast, and higher eukaryotic cells. Preferably, the host cells employed are *Escherichia coli,* insect, yeast, or a mammalian cell line such as COS or CHO. The polynucleotide sequences expressed in this manner may encode naturally occurring polypeptides, portions of naturally occurring polypeptides, or other variants thereof.

In a related aspect, polypeptides are provided that comprise at least a functional portion of a polypeptide having an amino acid sequence encoded by a polynucleotide of the present invention. As used herein, the "functional portion" of a polypeptide is that portion which contains the active site essential for affecting the function of the polypeptide, for example, the portion of the molecule that is capable of binding one or more reactants. The active site may be made up of separate portions present on one or more polypeptide chains and will generally exhibit high binding affinity.

Functional portions of a polypeptide may be identified by first preparing fragments of the polypeptide by either chemical or enzymatic digestion of the polypeptide, or by mutation analysis of the polynucleotide that encodes the polypeptide and subsequent expression of the resulting mutant polypeptides. The polypeptide fragments or mutant polypeptides are then tested to determine which portions retain biological activity, using, for example, the representative assays provided below.

Portions and other variants of the inventive polypeptides may also be generated by synthetic or recombinant means. Synthetic polypeptides having fewer than about 100 amino acids, and generally fewer than about 50 amino acids, may be generated using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain. See Merrifield, *J. Am. Chem. Soc.* 85:2149–2154, 1963. Equipment for automated synthesis of polypeptides is commercially available from suppliers such as Perkin Elmer/Applied BioSystems, Inc. (Foster City, Calif.), and may be operated according to the manufacturer's instructions. Variants of a native polypeptide may be prepared using standard mutagenesis techniques, such as oligonucleotide-directed, site-specific mutagenesis (Kunkel, *Proc. Natl. Acad. Sci. USA* 82:488–492, 1985). Sections of polynucleotide sequence may also be removed using standard techniques to permit preparation of truncated polypeptides.

In general, the polypeptides disclosed herein are prepared in an isolated, substantially pure, form. Preferably, the polypeptides are at least about 80% pure, more preferably at least about 90% pure, and most preferably at least about 99% pure. In certain embodiments, described in detail below, the isolated polypeptides are incorporated into pharmaceutical compositions or vaccines.

The present invention also contemplates methods for modulating the polynucleotide and/or polypeptide content and composition of an organism, such methods involving stably incorporating into the genome of the organism a construct containing DNA of the present invention. In one embodiment, the target organism is a mammal, preferably a human, for example for human gene therapy. In a related aspect, a method for producing an organism having an altered genotype or phenotype is provided, the method comprising transforming a cell with a DNA construct of the present invention to provide a transgenic cell, and cultivating the transgenic cell under conditions conducive to regeneration and mature organism growth.

The isolated polynucleotides of the present invention have utility in genome mapping, in physical mapping, and in positional cloning of genes. Additionally, the polynucleotide sequences identified as SEQ ID NOS: 1–35 and their variants may be used to design oligonucleotide probes and primers. Oligonucleotide probes and primers have sequences that are substantially complementary to the polynucleotide of interest over a certain portion of the polynucleotide. Oligonucleotide probes designed using the polynucleotides of the present invention may be used to detect the presence and examine the expression patterns of genes in any organism having sufficiently similar DNA and RNA sequences in their cells using techniques that are well known in the art, such as slot blot DNA hybridization techniques. Oligonucleotide primers designed using the polynucleotides of the present invention may be used for PCR amplfications. Oligonucleotide probes and primers designed using the polynucleotides of the present invention may also be used in connection with various microarray technologies, including the microarray technology of Affymetrix (Santa Clara, Calif.).

The polynucleotides of the present invention may also be used to tag or identify an organism or reproductive material therefrom. Such tagging may be accomplished, for example, by stably introducing a non-disruptive non-functional heterologous polynucleotide identifier into an organism, the polynucleotide comprising one of the polynucleotides of the present invention.

DETAILED DESCRIPTION

Polynucleotides were isolated by high throughput sequencing of cDNA libraries prepared from mouse airway-induced eosinophilia, rat dermal papilla and mouse stromal cells as described below, in Example 1. Isolated polynucleotides of the present invention include the polynucleotides identified as SEQ ID NOS: 1–35; isolated polynucleotides comprising a polynucleotide sequence selected from the group consisting of SEQ ID NOS: 1–35; isolated polynucleotides comprising at least a specified number of contiguous residues (x-mers) of any of the polynucleotides identified as SEQ ID NOS: 1–35; polynucleotides complementary to any of the above polynucleotides; anti-sense sequences corresponding to any of the above polynucleotides; and variants of any of the above polynucleotides, as that term is described in this specification. The present invention also provides isolated polypeptide sequences identified in the attached Sequence Listing as SEQ ID NO: 36–65; polypeptide variants of those sequences; and polypeptides comprising the isolated polypeptide sequences and variants of those sequences.

The correspondence of isolated polynucleotides encoding isolated polypeptides of the present invention, and the functionality of the polypeptides, are shown, below, in Table 1.

TABLE 1

| SEQ ID NO Poly-nucleotides | SEQ ID NO Poly-peptides | Activity Category | Functionality |
|---|---|---|---|
| 1 | 36 | Secretory molecule | Hypothetical 131.1 kDa protein |
| 2 | 37 | Secretory molecule/cytokine/ cell signaling | ZCYTO7 belongs to a family of IL-17-related cytokies differing in patterns of expression and proinflammatory responses that may be transduced through a cognate set of cell surface receptors. IL-17 is a T cell-derived cytokine that may play an important role in the imitation or maintenance of the proinflammatory response. Whereas expression of IL-17 is restricted to activated T cells, the W-17 receptor is found to be widely expressed, a finding consistent with the pleiotropic activities of IL-17. |
| 3 | 38 | Secretory molecule | Novel |
| 4 | 39 | Receptor/cytokinel cell signaling | Tumor endothelial marker 1 precursor |
| 5 | 40 | Secretory molecule | ERO1-L (ERO1-like protein) is involved in oxidative endoplasmic reticulum (ER) protein folding in mammalian cells. Oxidizing conditions must be maintained in the BR to allow the formation of disulfide bonds in secretory proteins. A family of conserved genes, termed BRO for BR oxidoreductins, plays a key role in this process. ERO1-L is a type II integral membrane protein. |
| 6 | 41 | Secretory molecule | Novel |
| 7 | 42 | Receptor/transcription factor | EMR2 is an EGF-like module that is part of the epideral growth factor (EGF)-TM7 proteins, which also include EMR1, (EGF-like molecule containing mucin-like hormone receptor 1) F4/80, and CD97. These proteins constitute a recently defined class B GPCR subfamily and are predominantly expressed on leukocytes. These molecules possess N-terminal EGF-like domains coupled to a seven-span transmembrane (7TM) moiety via a mucin-like spacer domain. EMR2 contains a total of five tandem EGF-like domains and expresses similar protein isoforms consisting of various numbers of EGF-like domains as a result of alternative RNA splicing. EMR2 share many characteristics with CD97, including highly homologous EGF-like domains and identical gene organization, indicating that both genes are the products of a recent gene duplication event. Both EMR2 and CD97 are highly expressed in immune tissues; however, unlike CD97, which is ubiquitously expressed in most cell types, EMR2 expression is restricted to monocytes, macrophages |

TABLE 1-continued

| SEQ ID NO Polynucleotides | SEQ ID NO Polypeptides | Activity Category | Functionality |
|---|---|---|---|
| 8 | 43 | Secretory molecule/cell structure/motility, extracellular matrix | Bone/cartilage proteoglycan I (BGN) is also known as biglycan or PG-S1. BGN is found in the extracellular matrices of several connective tissues, especially in articular cartilages. The two glycosaminoglycan chains attached to BGN can be either chondroitin sulfate or dermatan sulfate. BGN belongs to the small interstitial proteoglycans family. BGN is a small leucine-rich proteoglycan and is a nonfibrillar extracellular matrix component with functions that include the positive regulation of bone formation. It is synthesized as a precursor with an NH(2)-terminal propeptide that is cleaved to yield the mature form found in vertebrate tissues. Bone morphogenetic protein-1 (BMP-1) cleaves proBGN at a single site, removing the propeptide and producing BGN. Soluble BGN purified from rat thymic myoid cells had hemopoietic activity capable of inducing preferential growth and differentiation of monocytic lineage cells from various hemopoietic sources, including brain inicroglial cells. The haemopoietic BGN plays an important role in generating brain-specific circumstances for development of microglial/monocytic cells |
| 9 | 44 | Secretory molecule | Tubidointerstitial nephritis antigen (TIN-ag) is a basement membrane glycoprotein reactive with autoantibodies in some forms of immunologically mediated human tubulointerstitial nephritis. TIN1 and TIN2 are alternatively spliced products of the TIN-Ag gene. The open reading frames of TIN 1 and TIN2 indicates the presence of a signal peptide and putative pre-propeptide and both forms contain putative calcium-binding sites. TIN1 additionally contains a characteristic laminin-like epidermal growth factor (EGF) motif and significant homology within the carboxy terminus with the cysteine protemase family of enzymes. The EGF motif bears important similarities in the positions of cysteines with two motifs in the propeptide of von Wiliebrand factor. The EGF motif and part of the region that is homologous with the cysteine proteinase family are removed from the TIN2 cDNA. The rest of the TIN1 and TIN2 sequences are identical. TIN-ag is expressed mainly in the kidney and in the intestinal epithelium |
| 10 | | Receptor-like molecule | Novel |
| 11 | 45 | Secretory molecule/gene/protein expression, RNA synthesis, transcription factors | Toso is a cell surface, specific regulator of Fas-induced apoptosis in T cells. Fas is a surface receptor that can transmit signals for apoptosis. Toso is expressed in lymphoid cells and expression is enhanced after cell-specific activation processes in T cells. Toso appeared limited to inhibition of apoptosis mediated by members of the TNF receptor family and was capable of inhibiting T cell seff-killing induced by TCR activation processes that up-regulate Fas ligand. To so inhibits caspase-8 processing, the most upstream caspase activity in Fas-mediated signaling, potentially through activation of cFLIP. Toso therefore serves as a novel regulator of Fas-mediated apoptosis and may act as a regulator of cell fate in T cells and other hematopoietic lineages. |

TABLE 1-continued

| SEQ ID NO Poly-nucleotides | SEQ ID NO Poly-peptides | Activity Category | Functionality |
|---|---|---|---|
| 12 | 46 | Secretory molecule/ gene/protein expression, RNA synthesis, transcription factors | Surface glycoprotein CD59 is a phosphatidyl-inositol-glycan-anchored glycoprotein involved in T-cell activation and restriction of complement-mediated lysis. It is also known as protectin, and is ubiquitously expressed on benign and malignant cells. CD59 inhibits complement (C)-mediated lysis of target cells by preventing the formation of the membrane attack complex, in the terminal step of C-ctivation. Recent experimental evidence demonstrates that CD59 is the main restriction factor of C-mediated lysis of malignant cells of different histotypes. Additionally, a soluble form of CD59, that retains its anchoring ability and functional properties, has been identified in body fluids and in culture supernatants of different malignant cells. CD59 may protect neoplastic cells from C-mediated lysis, contributing to their escape from innate C-control and to tumor progression. The expression of CD59 by neoplastic cells may contribute to impair the therapeutic efficacy of C-activating monoclonal antibodies (mAb) directed to tumor-associated antigens. CD59 can be utilized to improve the therapeutic efficacy of clinical approaches of humoral immunotherapy with C-activating mAb in human malignancies. |
| 13 | 47 | Secretory molecules/cell or organism defense, homeostasis, detoxification | Cytochrome B561 (cyb561) is a secretory vesicle-specific electron transport protein unique to neuroendocrine secretory vesicles. It binds two heme groups non-covalently and is an integral membrane protein. It acts as an electron channel and mediates equilibration of ascorbate-semidehydroascorbate inside the secretory veside with the ascorbate redox pair in the cytoplasim The role for this function is to regenerate ascorbate inside the secretory vesicle for use by monooxygenases. The secretory vesicles contain catecholamines and amidated peptides. Cyb561 belongs to the eukaryotic b561 family. |
| 14 | 48 | Secretory molecule | Novel |
| 15 | 49 | Receptor-hke molecule/ gene or protein expression, RNA synthesis, transcription factor | High affinity immunoglobulin epsilon receptor beta-subunit (FCER1) is also known as IgE Fc receptor, beta-subunit, FCER1b or FCE1b. FCBR1 binds to the Fc region of immunoglobulins epsilon and is a high affinity receptor. FCER1 plays a role in imitating the allergic response where binding of allergen to receptor-bound IgE leads to cell activation and the release of mediators, such as histamine. FCER1 is responsible for the manifestations of allergy and induces the secretion of important lymphokines. It functions as a tetramer consisting of an alpha chain, a beta chain, and two disulfide-linked gamma chains and is an integral membrane protein. Variants of the FCER1B gene have been identified, which are associated with an increased risk of developing atopy and bronchial asthma. Atopic dermatitis is a common skin disease frequently associated with allergic disorders such as allergic rhinitis and asthma. |
| 16 | 50 | Receptor-hke molecule | Hypothetical 10.3 kDa protein |
| 17 | 51 | Secretory molecule/antigen processing | Lysosomal thiol reductase IP30 catalyzes disulfide bond reduction both in vitro and in vivo and is optimally active at acidic pH. IP30 is important in disuffide bond reduction of proteins delivered to MHC class II-containing compartments and consequently in antigen processing. IP30 can be mediated by multiple lysosomal proteases. Proteins internalized into the endocytic pathway are usually degraded. Efficient proteolysis requires denaturation, induced by acidic conditions within lysosomes, and reduction of inter- and intrachain disulfide bonds. The active site, determined by mutagenesis, consists of a pair of cysteine residues separated by two amino acids, similar to other enzymes of the thioredoxin family. |

TABLE 1-continued

| SEQ ID NO Poly-nucleotides | SEQ ID NO Poly-peptides | Activity Category | Functionality |
|---|---|---|---|
| 18 | | Receptor-like molecule | RNA binding protein. |
| 19 | 52 | Secretory molecule/cellular | Notch4-like protein (ZNEU1) is part of the NOTCH4 family that encodes receptors responsible for cell fate decisions during development. These Notch receptors and their ligands, Delta and Jagged, have been implicated in several diseases. When truncated, constitutively active mutant forms of the Notch receptor appear to be involved in T-cell leukemia, mammary carcinomas and a tumorous germline phenotype. Notch4 genes are expressed specifically in endothelial cells. |
| 20 | 53 | Secretory molecule | Novel |
| 21 | 54 | Secretory molecule/transporter | Serotransferrin (siderophilin) (Tf) or beta-1-met-binding globulin is part of the transferrin family. Transferrins are iron binding transport proteins which can bind two atoins of ferric iron in association with the binding of an anion, usually bicarbonate. Tf is responsible for the transport of iron from sites of absorption and heme degradation to those of storage and utilization. Serum transferrin also has a further role in stimulating cell proliferation. Tf gene expression is modulated by vitamin A, testosterone, and peptide homiones. |
| 22 | 55 | Secretory molecule/ gene or protein expression, RNA synthesis, transcription factor | Insulin-like growth factor binding protein 5 protease (IGFBP-5) modulates the effects of insulin growth factors (IGFs) on cells. IGFBP-5 is synthesized by smooth muscle cells and binds to the extracellular matrix. It is also secreted into conditioned medium of cultured cells and is deaved into fragments by a concomitantly produced protease. These fragments have reduced affinity for the IGFs. IGFBP-5 protease belongs to a family of serine-metallo proteases. |
| 23 | 56 | Secretory molecule/cellar development | Major epididymis-specific protein E4 is also known as epididymal protein BB-20. It belongs to WAP-type 'four-disulfide core' family and plays a role in the inaturation of spermatozoa during its movement through the epididymis and the capacity of spemi to fertilize ova. Expression of E4 was located to the epithelial cells of the cauda epididymis and proximal segment of the ductus deferens by in situ hybridization. No expression was found in sections of the corpus and caput epididymis, testis, and liver. |
| 24 | | Secretory molecule/cell signaling | TNFR-related death receptor-6 DR6 contains an extracellular region containing varying numbers of cysteine-rich domains and an intracellular region that contains the death domain. Death receptors are activated in a ligand-dependent or independent manner and transduce apoptotic signals via their respective intracellular death domains. |
| 25 | 57 | Receptor-like molecule | Novel |
| 26 | 58 | Secretory molecule/regniation | Channel inducing factor precursor (CHIF) or corticosteroid-induced protein induces a potassium channel when expressed in Xenopus oocytes and activates endogenous oocyte transport proteins. It is a type I membrane protein selectively present in the distal parts of the nephron (medullary and papillary collecting ducts and end portions of cortical collecting tubule) and in the epithelial cells of the distal colon. No expression is found in renal proximal tubule, loop of Henie and distal tubule, proximal colon, small intestine, lung, choroid plexus, salivary glands, or brain. CHIF belongs to the ATP1G1 /PLM / Mat-8 family and exhibits significant homologies with proteins that are putatively regulatory (phospholemman, gamma-subunit of Na(+)-K(+)-ATPase, Mat-8). |
| 27 | 59 | Secretory molecule | Hepatocellular carcinoma-associated antigen 112. |

TABLE 1-continued

| SEQ ID NO Poly-nucleotides | SEQ ID NO Poly-peptides | Activity Category | Functionality |
|---|---|---|---|
| 28 | 60 | Receptor-iike molecule/homeostasis | Lymphatic endothelium-specific hyaiuronan receptor LYVE-1 is a major receptor for hyaiuronan (HA) on the lymph vessal wall molecule that binds both soluble and immobilized HA. LYVE-1 plays a role in the control of the IIA pathway. The extracellular matrix glycosaminoglycan hyaluronan (HA) is an abundant component of skin and mesenchymal tissues where it facilitates cell immigration during wound healing, inflammation, and embryonic morphogenesis. Both during normal tissue homeostasis and particularly after tissue injury, HA is mobilized from these sites through symphatic vessels to the lymph nodes where it is degraded before entering the circulation for rapid uptake by the liver. LYVE-1 is similar to the CD44 HA receptor, but in contrast to CD44, LYVE-1 colocalizes with HA on the luminal face of the lymph vessel wall and is completely absent from blood vessels. |
| 29 | 61 | Receptor-like molecule/cell signaling | G protein-coupled receptor GPR35 is an integral membrane protein that belongs to family 1 of G-protein coupled receptors (GPRC). The GPCR family shares a structural motif of seven transmembrane segments with large numbers of conserved residues in those regions. |
| 30 | 62 | Receptor-iike molecule | Tumor-associated glycoprotein E4 is also known as Taal or Tage4 and belongs to the immunoglobulin superfamily. This family contains cell adhesion molecules which have wide-ranging functions and mediate a variety of homotypic and heterotypic cellular interactions playing a general role in cell surface recognition. The Tage4 gene product is closely related to the hepatocellular carcinoma antigen TuAg. 1. Tage4 is a glycoprotein expressed at the surface of colon carcinoma cell lines, but at a very low level in normal adult colon and lung tissue and not in normal tissues tested. |
| 31 | 63 | Secretory molecule | Hypothetical 28.6 kDa protein is also known as plunc, for palate, lung, and nasal epithelium clone. Expression of plunc is associated with the palate, nasal septum, and nasal conchae. It is also expressed strongly in the trachea and bronchi of the adult lung. No significant homdogies with known genes were observed at the nucleotide level and limited amino acid homology with two salivary gland-specific proteins was noted. The amino acid sequence revealed consensus sequences for N-glycosylation, protein kinase C and casein kinase phosphorylation, as well as a leucine zipper. In addition, an unique amino acid sequence repeat sequence is located near the amino-terminal portion of the protein. |
| 32 | 64 | Secretory molecule | Claudin-18 (Cldn18) is a component of tight junction (TJ) strands and belongs to the daudin family. Claudins are integral membrane protein component of tight functions, a structure controlling cell-to-cell adhesion and, consequently, regulating paracellular and transcellular transport of sohites across epithelia and endothelia. The claudin family also includes occiudin and 17 other distinct claudins. Claudin family members are tetra-span transmembrane proteins that are localized in cell-specific TJs. in multicellular organisms, various compositionally distinct fluid compartments are established by epithelial and endothelial cellular sheets. For these cells to function as barriers, TJs are considered to create a primary barrier for the diffusion of solutes through the paracellular pathway. Claudins are therefore responsible for TJ-specific obliteration of the intercellular space. |

TABLE 1-continued

| SEQ ID NO Polynucleotides | SEQ ID NO Polypeptides | Activity Category | Functionality |
| --- | --- | --- | --- |
| 33 | | Secretory molecule | Glutamine repeat protein 1 (GRP-1) contains simple tandem repeats of the trinucleotide sequence CAG that encode homopolytneric stretches of glutamine. Although polyglutamine has been identified in diverse proteins, it is present predominantly in transcription factors. Greater than two-thirds of GRP-1 are only two amino acids, namely glutamine (50%) and histidine (18%). There are four polyglutamine motifs interspersed with histidine-rich regions. There is also a putative nuclear localization signal flanked by sites for possible serine phosphorylation. GRP-1 mRNA was expressed constitutively in some macrophage cell lines and B and T cell lines. Interferon-gamma or lipopysaccharide augmented GRP-1 inRNA expression in the mouse macrophage cell line ANA-1. Because polyglutamine motifs can cause protein oligomerization and can function as transcriptional activation domains, GRP-1 is a transcription factor associated with interferon-gama- or lipopolysaccharide-induced activation of macrophages. |
| 34 | | Secretory molecule | Alpha-1 collagen |
| 35 | 65 | Receptor-like molecule/Cell signaling | Gdnf family receptor alpha 4, transmembrane isoform (Gfta4) is a members of the Gdnf protein family that signal through receptors consisting of a GPI-huked GFRalpha subunit and the transmembrane tyrosine kinase Ret. Gfra4 is expressed in many tissues, including nervous system, m which intron retention leads to a putative intracellular or secreted GFRalpha4 protein. Efficient splicing occurs only in thyroid, parathyroid, and pituitary and less in adrenal glands. A splice form that leads to a GPI-linked GFRalpha4 receptor is expressed in juvenile thyroid and parathyroid glands. In newborn and mature thyroid as well as in parathyroid and pituitary glands major transcripts encode for a putative transmembrane isoform of GFRalpha4. GFRalpha4 expression may restrict the inherited cancer syndrome muitiple endocrine neoplasia type 2, associated with mutations in RET, to these cells. |

The word "polynucleotide(s)," as used herein, means a polymeric collection of nucleotides and includes DNA and corresponding RNA molecules and both single and double stranded molecules, including HnRNA and mRNA molecules, sense and anti-sense strands of DNA and RNA molecules, and comprehends cDNA, genomic DNA, and wholly or partially synthesized polynucleotides. An HnRNA, molecule contains introns and "corresponds to" a DNA molecule in a generally one-to-one manner. An mRNA molecule "corresponds to" an HnRNA and DNA molecule from which the introns have been excised. A polynucleotide of the present invention may be an entire gene, or any portion thereof. A gene is a DNA sequence which codes for a functional protein or RNA molecule. Operable anti-sense polynucleotides may comprise a fragment of the corresponding polynucleotide, and the definition of "polynucleotide" therefore includes all operable anti-sense fragments. Anti-sense polynucleotides and techniques involving anti-sense polynucleotides are well known in the art and are described, for example, in Robinson-Benion et al., Methods in Enzymol. 254(23): 363–375, 1995 and Kawasaki et al., Artific. Organs 20 (8): 836–848, 1996.

Identification of genomic DNA and heterologous species DNA can be accomplished by standard DNA/DNA hybridization techniques, under appropriately stringent conditions, using all or part of a cDNA sequence as a probe to screen an appropriate library. Alternatively, PCR techniques using oligonucleotide primers that are designed based on known genomic DNA, cDNA and/or protein sequences can be used to amplify and identify genomic and cDNA sequences. Synthetic DNA corresponding to the identified sequences and variants may be produced by conventional synthesis methods. All of the polynucleotides described herein are isolated and purified, as those terms are commonly used in the art.

As used herein, the term "oligonucleotide" refers to a relatively short segment of a polynucleotide sequence, generally comprising between 6 and 60 nucleotides, and comprehends both probes for use in hybridization assays and primers for use in the amplification of DNA by polymerase chain reaction.

As used herein, the term "x-mer," with reference to a specific value of "x," refers to a polynucleotide comprising at least a specified number ("x") of contiguous residues of any of the polynucleotides identified as SEQ ID NOS: 1–35. The value of x may be from about 20 to about 600, depending upon the specific sequence.

As used herein, the term "polypeptide" encompasses amino acid chains of any length, including full-length proteins, wherein amino acid residues are linked by covalent peptide bonds. Polypeptides of the present invention may be naturally purified products, or may be produced partially or wholly using recombinant techniques. Such polypeptides may be glycosylated with mammalian or other eukaryotic carbohydrates or may be non-glycosylated.

According to one embodiment, "variants" of the polynucleotides of the present invention, including the polynucleotides set forth as SEQ ID NOS: 1–35, as that term is used herein, comprehends polynucleotides producing an "E" value of 0.01 or less, as described below, or having at least a specified percentage identity to a polynucleotide of the present invention, as described below. Polynucleotide variants of the present invention may be naturally occurring allelic variants, or non-naturally occurring variants.

Polynucleotide and polypeptide sequences may be aligned, and percentages of identical residues in a specified region may be determined against another polynucleotide or polypeptide, using computer algorithms that are publicly available. Two exemplary algorithms for aligning and identifying the similarity of polynucleotide sequences are the BLASTN and FASTA algorithms. Polynucleotides may also be analyzed using the BLASTX algorithm, which compares the six-frame conceptual translation products of a nucleotide query sequence (both strands) against a protein sequence database. The percentage identity of polypeptide sequences may be examined using the BLASTP algorithm The BLASTN, BLASTP and BLASTX algorithms are available on the NCBI anonymous FTP server and are available from the National Center for Biotechnology Information (NCBI), National Library of Medicine, Building 38A, Room 8N805, Bethesda, MD 20894, USA. The BLASTN algorithm Version 2.0.11 [Jan-20-2000], set to the parameters described below, is preferred for use in the determination of polynucleotide variants according to the present invention. The BLASTP algorithm, set to the parameters described below, is preferred for use in the determination of polypeptide variants according to the present invention. The use of the BLAST family of algorithms, including BLASTN, BLASTP and BLASTX, is described at NCBI's website and in the publication of Altschul, et al., *Nucleic Acids Res.* 25: 3389–3402, 1997.

The FASTA and FASTX algorithms are available on the Internet, and from the University of Virginia by contacting David Hudson, Vice Provost for Research, University of Va., P.O. Box 9025, Charlottesville, Va. 22906–9025, USA. The FASTA algorithm, set to the default parameters described in the documentation and distributed with the algorithm, may be used in the determination of polynucleotide variants. The readme files for FASTA and FASTX Version 1.0x that are distributed with the algorithms describe the use of the algorithms and describe the default parameters. The use of the FASTA and FASTX algorithms is described in Pearson and Lipman, *Proc. Natl. Acad. Sci. USA* 85:2444–2448, 1988; and Pearson, *Methods in Enzymol.* 183:63–98, 1990. The following running parameters are preferred for determination of alignments and similarities using BLASTN that contribute to the E values and percentage identity: Unix running command with default parameter values thus: blastall -p blastn -d embldb -e 10 -G 0 -E 0 -r 1 -v 30 -b 30 -i queryseq -o results; the Parameters are : -p Program Name [String]; -d Database [String]; -e Expectation value (E) [Real]; -G Cost to open a gap (zero invokes default behavior) [Integer]; -E Cost to extend a gap (zero invokes default behavior) [Integer]; -r Reward for a nucleotide match (BLASTN only) [Integer]; -v Number of one-line descriptions (V) [Integer]; -b Number of alignments to show (B) [Integer]; -i Query File [File In];-o BLAST report Output File [FileOut] Optional.

The "hits" to one or more database sequences by a queried sequence produced by BLASTN or FASTA or a similar algorithm align and identify similar portions of sequences. The hits are arranged in order of the degree of similarity and the length of sequence overlap. Hits to a database sequence generally represent an overlap over only a fraction of the sequence length of the queried sequence.

The BLASTN and FASTA algorithms produce "Expect" values for alignments. The Expect value (E) indicates the number of hits one can "expect" to see over a certain number of contiguous sequences by chance when searching a database of a certain size. The Expect value is used as a significance threshold for determining whether the hit to a database, such as the preferred EMBL database, indicates true similarity. For example, an E value of 0.1 assigned to a hit is interpreted as meaning that in a database of the size of the EMBL database, one might expect to see 0.1 matches over the aligned portion of the sequence with a similar score simply by chance. The aligned and matched portions of the sequences, then, have a probability of 90% of being the same by this criterion. For sequences having an E value of 0.01 or less over aligned and matched portions, the probability of finding a match by chance in the EMBL database is 1% or less using the BLASTN or FASTA algorithnm.

According to one embodiment, "variant" polynucleotides, with reference to each of the polynucleotides of the present invention, preferably comprise sequences having the same number or fewer nucleic acids than each of the polynucleotides of the present invention and producing an E value of 0.01 or less when compared to the polynucleotide of the present invention. That is, a variant polynucleotide is any sequence that has at least a 99% probability of being the same as the polynucleotide of the present invention, measured as having an E value of 0.01 or less using the BLASTN or FASTA algorithms set at the default parameters. According to a preferred embodiment, a variant polynucleotide is a sequence having the same number or fewer nucleic acids than a polynucleotide of the present invention that has at least a 99% probability of being the same as the polynucleotide of the present invention, measured as having an E value of 0.01 or less using the BLASTN or FASTA algorithms set at the default parameters.

Alternatively, variant polynucleotides of the present invention may comprise a sequence exhibiting at least about 40%, more preferably at least about 60%, more preferably yet at least about 75%, and most preferably at least about 90% similarity to a polynucleotide of the present invention, determined as described below. The percentage similarity is determined by aligning sequences using one of the BLASTN or FASTA algorithms, set at default parameters, and identifying the number of identical nucleic acids over the best aligned portion; dividing the number of identical nucleic acids by the total number of nucleic acids of the polynucleotide of the present invention; and then multiplying by 100 to determine the percentage similarity. For example, a polynucleotide of the present invention having 220 nucleic acids has a hit to a polynucleotide sequence in the EMBL database having 520 nucleic acids over a stretch of 23 nucleotides in the alignment produced by the BLASTN algorithm using the default parameters. The 23 nucleotide hit includes 21 identical nucleotides, one gap and one different nucleotide. The percentage similarity of the polynucleotide of the present invention to the hit in the EMBL library is thus 21/220 times 100, or 9.5%. The polynucleotide sequence in the EMBL database is thus not a variant of a polynucleotide of the present invention.

Alternatively, variant polynucleotides of the present invention hybridize to a polynucleotide of the present invention under stringent hybridization conditions. As used herein, "stringent conditions" mean prewashing in a solution of 6× SSC, 0.2% SDS; hybridizing at 65° C., 6× SSC, 0.2% SDS overnight; followed by two washes of 30 minutes each in 1× SSC, 0.1% SDS at 65° C. and two washes of 30 minutes each in 0.2×SSC, 0.1% SDS at 65° C.

The present invention also encompasses allelic variants of the disclosed sequences, together with DNA sequences that differ from the disclosed sequences but which, due to the degeneracy of the genetic code, encode a polypeptide which is the same as that encoded by a DNA sequence disclosed herein. Thus, polynucleotides comprising sequences that differ from the polynucleotide sequences recited in SEQ ID NOS: 1–35, or complements, reverse sequences, or reverse complements of those sequences as a result of conservative substitutions are contemplated by and encompassed within the present invention. Additionally, polynucleotides comprising sequences that differ from the polynucleotide sequences recited in SEQ ID NOS: 1–35, or complements, reverse complements, or reverse sequences as a result of deletions and/or insertions totaling less than 10% of the total sequence length are also contemplated by and encompassed within the present invention.

The polynucleotides of the present invention may be isolated from various DNA libraries, or may be synthesized using techniques that are well known in the art. The polynucleotides may be synthesized, for example, using automated oligonucleotide synthesizers (e.g. Beckman Oligo 1000M DNA Synthesizer) to obtain polynucleotide segments of up to 50 or more nucleic acids. A plurality of such polynucleotide segments may then be ligated using standard DNA manipulation techniques that are well known in the art of molecular biology. One conventional and exemplary polynucleotide synthesis technique involves synthesis of a single stranded polynucleotide segment having, for example, 80 nucleic acids, and hybridizing that segment to a synthesized complementary 85 nucleic acid segment to produce a 5-nucleotide overhang. The next segment may then be synthesized in a similar fashion, with a 5-nucleotide overhang on the opposite strand. The "sticky" ends ensure proper ligation when the two portions are hybridized. In this way, a complete polynucleotide of the present invention may be synthesized entirely in vitro.

SEQ ID NOS: 2, 3, 5, 7–9, 11, 12, 14, 15, 17, 19–21, 23, 26, 28 and 30–32 are full-length sequences. The remaining polynucleotides are referred to as "partial" sequences, in that they may not represent the full coding portion of a gene encoding a naturally occurring polypeptide. The partial polynucleotide sequences disclosed herein may be employed to obtain the corresponding full-length genes for various species and organisms by, for example, screening DNA expression libraries using hybridization probes based on the polynucleotides of the present invention, or using PCR amplification with primers based upon the polynucleotides of the present invention. In this way one can, using methods well known in the art, extend a polynucleotide of the present invention upstream and downstream of the corresponding mRNA, as well as identify the corresponding genomic DNA, including the promoter and enhancer regions, of the complete gene. The present invention thus comprehends isolated polynucleotides comprising a sequence identified in SEQ ID NOS: 1–35, or a variant of one of the specified sequences, that encode a functional polypeptide, including full-length genes. Such extended polynucleotides may have a length of from about 50 to about 4,000 nucleic acids or base pairs, and preferably have a length of less than about 4,000 nucleic acids or base pairs, more preferably yet a length of less than about 3,000 nucleic acids or base pairs, more preferably yet a length of less than about 2,000 nucleic acids or base pairs. Under some circumstances, extended polynucleotides of the present invention may have a length of less than about 1,800 nucleic acids or base pairs, preferably less than about 1,600 nucleic acids or base pairs, more preferably less than about 1,400 nucleic acids or base pairs, more preferably yet less than about 1,200 nucleic acids or base pairs, and most preferably less than about 1,000 nucleic acids or base pairs.

Polynucleotides of the present invention comprehend polynucleotides comprising at least a specified number of contiguous residues (x-mers) of any of the polynucleotides identified as SEQ ID NOS: 1–35 or their variants. According to preferred embodiments, the value of x is preferably at least 20, more preferably at least 40, more preferably yet at least 60, and most preferably at least 80. Thus, polynucleotides of the present invention include polynucleotides comprising a 20-mer, a 40-mer, a 60-mer, an 80-mer, a 100-mer, a 120-mer, a 150-mer, a 180-mer, a 220-mer a 250-mer, or a 300-mer, 400-mer, 500-mer or 600-mer of a polynucleotide identified as SEQ ID NOS: 1–35 or a variant of one of the polynucleotides identified as SEQ ID NOS: 1–35.

Polynucleotide probes and primers complementary to and/or corresponding to SEQ ID NOS: 1–35, and variants of those sequences, are also comprehended by the present invention. Such oligonucleotide probes and primers are substantially complementary to the polynucleotide of interest. An oligonucleotide probe or primer is described as "corresponding to"a polynucleotide of the present invention, including one of the sequences set out as SEQ ID NOS: 1–35 or a variant, if the oligonucleotide probe or primer, or its complement, is contained within one of tde sequences set out as SEQ ID NOS: 1–35 or a variant of one of the specified sequences.

Two single stranded sequences are said to be substantially complementary when the nucleotides of one strand, optimally aligned and compared using, for example, the BLAST algorithm as described above, with the appropriate nucleotide insertions and/or deletions, pair with at least 80%, preferably at least 90% to 95%, and more preferably at least 98% to 100%, of the nucleotides of the other strand. Alternatively, substantial complementarity exists when a first DNA strand will selectively hybridize to a second DNA strand under stringent hybridization conditions. Stringent hybridization conditions for determining complementarity include salt conditions of less than about 1 M, more usually less than about 500 mM and preferably less than about 200 mM. Hybridization temperatures can be as low as 5° C., but are generally greater than about 22° C., more preferably greater than about 30° C. and most preferably greater than about 37° C. Longer DNA fragments may require higher hybridization temperatures for specific hybridization. Since the stringency of hybridization may be affected by other factors such as probe composition, presence of organic solvents and extent of base mismatching, the combination of parameters is more important than the absolute measure of any one alone. The DNA from plants or samples or products containing plant material can be either genomic DNA or DNA derived by preparing cDNA from the RNA present in the sample.

In addition to DNA-DNA hybridization, DNA-RNA or RNA-RNA hybridization assays are also possible. In the case of DNA-RNA hybridization, the mRNA from expressed genes would then be detected instead of genomic DNA or cDNA derived from mRNA of the sample. In the case of RNA-RNA hybridization, RNA probes could be used. In addition, artificial analogs of DNA hybridizing specifically to target sequences could also be employed.

In specific embodiments, the oligonucleotide probes and/or primers comprise at least about 6 contiguous residues, more preferably at least about 10 contiguous residues, and most preferably at least about 20 contiguous residues complementary to a polynucleotide sequence of the present invention. Probes and primers of the present invention may be from about 8 to 100 base pairs in length or, preferably from about 10 to 50 base pairs in length or, more preferably from about 15 to 40 base pairs in length. The probes can be easily selected using procedures well known in the art, taking into account DNA-DNA hybridization stringencies, annealing and melting temperatures, potential for formation of loops and other factors, which are well known in the art. Tools and software suitable for designing probes, and especially suitable for designing PCR primers, are available on the Internet. Preferred techniques for designing PCR primers are also disclosed in Dieffenbach and Dyksler, PCR primer: a laboratory manual. Cold Spring Harbor Laboratory Press, Cold Spring Harbor, N.Y., 1995.

A plurality of oligonucleotide probes or primers corresponding to a polynucleotide of the present invention may be provided in a kit form. Such kits generally comprise multiple DNA or oligonucleotide probes, each probe being specific for a polynucleotide sequence. Kits of the present invention may comprise one or more probes or primers corresponding to a polynucleotide of the present invention, including a polynucleotide sequence identified in SEQ ID NOS: 1–35.

In one embodiment useful for high-throughput assays, the oligonucleotide probe kits of the present invention comprise multiple probes in an array format, wherein each probe is immobilized in a predefined, spatially addressable location on the surface of a solid substrate. Array formats which may be usefully employed in thle present invention are disclosed, for example, in U.S. Pat. Nos. 5,412,087, 5,545,531, and PCT Publication No. WO 95/00530, the disclosures of which are hereby incorporated by reference.

Oligonucleotide probes for use in the present invention may be constructed synthetically prior to immobilization on an array, using techniques well known in the art (see, for example, *Oligonucleotide Synthesis: A Practical Approach*, Gait, ed., IRL Press, Oxford, 1984). Automated equipment for the synthesis of oligonucleotides is available commercially from such companies as Perkin Elmer/Applied Biosystems Division (Foster City, Calif.) and may be operated according to the manufacturer's instructions. Alternatively, the probes may be constructed directly on the surface of the array using techniques taught, for example, in PCT Publication No. WO 95/00530.

The solid substrate and the surface thereof preferably form a rigid support and are generally formed from the same material. Examples of materials from which the solid substrate may be constructed include polymers, plastics, resins, membranes, polysaccharides, silica or silica-based materials, carbon, metals and inorganic glasses. Synthetically prepared probes may be immobilized on the surface of the solid substrate using techniques well known in the art, such as those disclosed in U.S. Pat. No. 5,412,087.

In one such technique, compounds having protected fuctional groups, such as thiols protected with photochemically removable protecting groups, are attached to the surface of the substrate. Selected regions of the surface are then irradiated with a light source, preferably a laser, to provide reactive thiol groups. This irradiation step is generally performed using a mask having apertures at predefined locations using photolithographic techniques well known in the art of semiconductors. The reactive thiol groups are then incubated with the oligonucleotide probe to be immobilized. The precise conditions for incubation, such as temperature, time and pH, depend on the specific probe and can be easily determined by one of skill in the art. The surface of the substrate is washed free of unbound probe and the irradiation step is repeated using a second mask having a different pattern of apertures. The surface is subsequently incubated with a second, different, probe. Each oligonucleotide probe is typically immobilized in a discrete area of less than about 1 mm$^2$. Preferably each discrete area is less than about 10,000 mm$^2$, more preferably less than about 100 mm$^2$. In this manner, a multitude of oligonucleotide probes may be immobilized at predefined locations on the array.

The resulting array may be employed to screen for differences in organisms or samples or products containing genetic material as follows. Genomic or cDNA libraries are prepared using techniques well known in the art. The resulting target DNA is then labeled with a suitable marker, such as a radiolabel, chromophore, fluorophore or chemiluminescent agent, using protocols well known for those skilled in the art. A solution of the labeled target DNA is contacted with the surface of the array and incubated for a suitable period of time.

The surface of the array is then washed free of unbound target DNA and the probes to which the target DNA hybridized are determined by identifying those regions of the array to which the markers are attached. When the marker is a radiolabel, such as $^{32}$P, autoradiography is employed as the detection method. In one embodiment, the marker is a fluorophore, such as fluorescein, and the location of bound target DNA is determined by means of fluorescence spectroscopy. Automated equipment for use in fluorescence scanning of oligonucleotide probe arrays is available from Affymetrix, Inc. (Santa Clara, Calif.) and may be operated according to the manufacturer's instructions. Such equipment may be employed to determine the intensity of fluorescence at each predefined location on the array, thereby providing a measure of the amount of target DNA bound at each location. Such an assay would be able to indicate not only the absence and presence of the marker probe in the target, but also the quantitative amount as well.

In this manner, oligonucleotide probe kits of the present invention may be employed to examine the presence/absence (or relative amounts in case of mixtures) of polynucleotides in different samples or products containing different materials rapidly and in a cost-effective manner.

Another aspect of the present invention involves collections of a plurality of polynucleotides of the present invention. A collection of a plurality of the polynucleotides of the present invention, particularly the polynucleotides identified as SEQ ID NOS: 1–35, may be recorded and/or stored on a storage medium and subsequently accessed for purposes of analysis, comparison, etc. One utility for such sets of sequences is the analysis of the set, either alone or together with other sequences sets, for single nucleotide polymorphisms (SNPs) between sequences from different tissues and/or individuals for genetic studies, mapping and fingerprinting purposes. Suitable storage media include magnetic media such as magnetic diskettes, magnetic tapes, CD-ROM storage media, optical storage media, and the like. Suitable storage media and methods for recording and storing information, as well as accessing information such as polynucleotide sequences recorded on such media, are well known in the art. The polynucleotide information stored on the storage medium is preferably computer-readable and may be used for analysis and comparison of the polynucleotide information.

Another aspect of the present invention thus involves storage medium on which are recorded a collection of the polynucleotides of the present invention, particularly a collection of the polynucleotides identified as SEQ ID NOS: 1–35. According to one embodiment, the storage medium includes a collection of at least 20, preferably at least 50, more preferably at least 100, and most preferably at least 200 of the polynucleotides of the present invention, preferably the polynucleotides identified as SEQ ID NOS: 1–35, or variants of those polynucleotides.

Another aspect of the present invention involves a combination of polynucleotides, the combination containing at least 5, preferably at least 10, more preferably at least 20, and most preferably at least 50 different polynucleotides of the present invention, including polynucleotides selected from SEQ ID NOS: 1–35, or variants of these polynucleotides.

In another aspect, the present invention provides DNA constructs comprising, in the 5'-3' direction, a gene promoter sequence; an open reading frame coding for at least a functional portion of a polypeptide encoded by a polynucleotide of the present invention; and a gene termination sequence. The open reading frame may be orientated in either a sense or antisense direction. DNA constructs comprising a non-coding region of a gene coding for an enzyme encoded by the above DNA sequences or a nucleotide sequence complementary to a non-coding region, together with a gene promoter sequence and a gene termination sequence, are also provided. Preferably, the gene promoter and termination sequences are functional in a host cell. More preferably, the gene promoter and termination sequences are common to those of the polynucleotide being introduced. Other promoter and termination sequences generally used in the art, such as the Cauliflower Mosaic Virus (CMV) promoter, with or without enhancers, such as the Kozak sequence or Omega enhancer, and *Agrobacterium tumefaciens* nopalin synthase terminator may be usefuly employed in the present invention. Tissue-specific promoters may be employed in order to target expression to one or more desired tissues. The DNA construct may further include a marker for the identification of transformed cells.

Techniques for operatively liking the components of the DNA constructs are well known in the art and include the use of synthetic linkers containing one or more restriction endonuclease sites as described, for example, by Sambrook et al., *Molecular Cloning: a laboratory manual,* Cold Spring Harbor Laboratory Press, Cold Spring Harbor, N.Y., 1989. The DNA constructs of the present invention may be linked to a vector having at least one replication system, for example, *Escherichia coli,* whereby after each manipulation, the resulting construct can be cloned and sequenced and the correctness of the manipulation determined.

Transgenic cells comprising the DNA constructs of the present invention are provided, together with organisms comprising such transgenic cells. Techniques for stably incorporating DNA constructs into the genome of target organisms, such as mammals, are well known in the art and include electroporation, protoplast fusion, injection into reproductive organs, injection into immature embryos, high velocity projectile introduction and the like. The choice of technique will depend upon the target organism to be transformed. In one embodiment, naked DNA is injected or delivered orally. Once the cells are transformed, cells having the DNA construct incorporated in their genome are selected. Transgenic cells may then be cultured in an appropriate medium using techniques well known in the art.

In yet a further aspect, the present invention provides methods for modifying the level (concentration) or activity of a polypeptide in a host organism comprising stably incorporating into the genome of the organism a DNA construct of the present invention. The DNA constructs of the present invention may be used to transform a variety of organisms, including mammals, for example to make experimental gene knock out or transgenic annals.

Further, the polynucleotides of the present invention have particular application for use as non-disruptive tags for marking organisms, including commercially valuable animals, fish, bacteria and yeasts. DNA constructs comprising polynucleotides of the present invention may be stably introduced into an organism as heterologous, non-functional, non-disruptive tags. It is then possible to identify the origin or source of the organism at a later date by determining the presence or absence of the tag(s) in a sample of material.

Detection of the tag(s) may be accomplished using a variety of conventional techniques, and will generally involve the use of nucleic acid probes. Sensitivity in assaying the presence of probe can be usefully increased by using branched oligonucleotides, as described by Horn et al., *Nucleic Acids Res.* 25(23):4842–4849, 1997, enabling to detect as few as 50 DNA molecules in the sample.

In particular, the polynucleotides of the present invention encode polypeptides that have important roles in processes such as induction of growth differentiation of tissue-specific cells, cell migration, cell proliferation, and cell-cell interaction. These polypeptides are important in the maintenance of tissue integrity, and thus are important in processes such as wound healing. Some of these polypeptides act as modulators of immune responses, such as immunologically active polypeptides for the benefit of offspring. In addition, many polypeptides are immunologically active, making them important therapeutic targets in a whole range of disease states. Antibodies to the polypeptides of the present invention and small molecule inhibitors related to the polypeptides of the present invention may also be used for modulating immune responses and for treatment of diseases according to the present invention.

SEQ ID NOS: 1; 2; 4; 5; 6; 8; 9; 11; 12; 14; 17; 19–24; 26; 27; 31–34 encode secreted polypeptides. SEQ ID NOS: 10; 15; 16; 18; 25; 28; 30; and 35 encode polypeptides acting as receptors. SEQ ID NOS: 2; 4; 24; 29 and 35 encode polypeptides with cell signaling activity, which may be either intracellular or extracellular. Kinase genes, for example, encode polypeptides that phosphorylate specific substrates during cell-to-cell signaling. While some kinases are involved in normal metabolism and nucleotide production, others are significant for altering the activity of many cellular processes through the phosphorylation of specific proteins. Polypeptides encoded by these genes are important in the transmission of intracellular signals resulting from the binding of extracellular ligands such as hormones, growth factors or cytokines to membrane-bound receptors. The utility of polynucleotides encoding kinases resides in the manipulation of their signaling activities and downstream effects for the diagnosis and treatment of mammalian diseases that may be a consequence of inappropriate expression of these kinase genes.

SEQ ID NOS: 2 and 4 encode polypeptides with cytokine activity. Cytokine or growth factor polynucleotides encode polypeptides involved in intercellular signaling and represent another important class of molecules. Polynucleotides encoding such genes have utility in the diagnosis and treatment of disease.

SEQ ID NOS: 7; 11; 12; 15 and 22 encode polypeptides with transcription factor activity. These polynucleotides encode polypeptides required for the control of synthesis of proteins in tissue specific manner and have utility for the modification of protein synthesis for the control of disease.

SEQ ID NOS: 8 encode polypeptides acting in the extracellular matrix.

SEQ ID NOS: 11; 12; 15 and 22 encode polypeptides with RNA synthesis activities.

SEQ ID NO: 12 encodes a polypeptide having CD antigen activity. Such polynucleotides have utility as modulators of the composition, expression level and class of CD antigen expressed, which influence immune responses to self-antigens, neo-antigens and infectious agents.

Further exemplary specific utilities, for exemplary polynucleotides of the present invention, are specified in the Table below.

| SEQ ID NO: | UTILITY |
| --- | --- |
| 2 | Promoting immune response as part of a vaccine or anti-cancer treatment. Inhibitors of this molecule can be useful as anti-inflammatory treatment, e.g. for autoimmune diseases or allergies. |
| 11;19 | Utility as a target for cancer treatment and as an immunoregulatory and anti-inflammatory molecule |
| 12 | Diagnostic for specific types of cancer and for development of an anti-cancer treatment. |
| 15 | As a target for antagonists in the treatment of diseases such as asthma and allergy. |
| 22 | Useful to inhibit or enhance the activity of the soluble molecule that binds this protein. |
| 28 | Useful to promote or block cell trafficking and therefore in the treatment as anti-inflammatory and/or vaccine adjuvant where it can promoter inflammation. |
| 35 | Useful for tissue and neural regeneration. |

The following examples are offered by way of illustration and not by way of limitation.

EXAMPLE 1

Isolation of cDNA Sequences from Mammalian Expression Libraries

The cDNA sequences of the present invention were obtained by high-throughput sequencing of cDNA expression libraries constructed mouse airways-induced eosinophilia, rat dermal papilla and mouse stromal cells. The cDNA libraries were prepared as follows.

cDNA Library from Dermal Papilla (DEPA)

Dermal papilla cells from rat hair vibrissae (whiskers) were grown in culture and the total RNA extracted from these cells using established protocols. Total RNA, isolated using TRIzol Reagent (BRL Life Technologies, Gaithersburg, Md.), was used to obtain mRNA using a Poly(A) Quik mRNA isolation kit (Stratagene, La Jolla, Calif.), according to the manufacturer's specifications. A cDNA expression library was then prepared from the mRNA by reverse transcriptase synthesis using a Lambda ZAP cDNA library synthesis kit (Stratagene).

cDNA Library from Mouse Airway-induced Eosinophilia (MALA)

Airway eosinophilia were induced in BALB/cByJ mice by administering 2 µg ovalbumin in 2 mg alum adjuvant intraperitoneally on day 0 and day 14, and subsequently 100 µg ovalbumin in 50 µl phosphate buffered saline (PBS) intranasally route on day 28. The accumulated eosinophils in the lungs were detected by washing the airways of the anesthetized mice with saline, collecting the washings (broncheolar lavage or BAL), and counting the numbers of eosinophils. The mice were sacrificed and total RNA was isolated from whole lung tissue using TRIzol Reagent (BRL Life Technologies). mRNA was isolated by using a Poly(A) Quik mRNA isolation kit (Stratagene, La Jolla, Calif.), according to the manufacturer's specifications. A cDNA expression library was then prepared from the mRNA by reverse transcriptase synthesis using a Lambda ZAP cDNA library synthesis kit (Stratagene).

cDNA Expression Library from Peripheral Lymph Node Stromal Cells (MLSA)

The peripheral axillary and brachial lymph nodes of BALB/cByJ mice with the flaky skin (fsn) mutation (Jackson Laboratories, Bar Harbour, Minn.) were dissected out. Single cell suspensions were obtained from the lymph nodes and cultured in tissue culture flasks at $10^7$ cells/ml in 20% fetal calf serum and Dulbecco's Minimum Essential Medium. After 2 days the non-adherent cells were removed. The adherent cells were cultured for a further 2 days and then treated with 0.25 g/100 ml Trypsin (ICN, Aurora, Ohio) and re-cultured. After a further 4 days, non-adherent cells were discarded and adherent cells removed by trypsinization. Remaining adherent cells were physically removed by scraping with a rubber policeman. All adherent stromal cells were pooled.

cDNA Expression Library from Flaky Skin Lymph Node Stromal Cells in pBK-CMV(MLSA)

Stromal cells from Flaky skin mice lymph nodes were grown in culture and the total RNA extracted from these cells using established protocols. Total RNA, isolated using TRIzol Reagent (BRL Life Technologies, Gaithersburg, Md.), was used to obtain mRNA using a Poly(A) Quik mRNA isolation kit (Stratagene, La Jolla, Calif.), according to the manufacturer's specifications. A cDNA expression library was then prepared from the mRNA by reverse transcriptase synthesis using a Lambda ZAP cDNA library synthesis kit (Stratagene).

cDNA sequences were obtained by high-throughput sequencing of the cDNA libraries described above using a Prism 377 sequencer (Perkin Elner/Applied Biosystems Division, Foster City Calif.), and are provided in SEQ ID NO: 1–35, with corresponding polypeptide sequences in SEQ ID NOS: 36–65.

EXAMPLE 2

Analysis of cDNA Sequences using BLAST Algorithms

BLASTN Polynucleotide Analysis

The isolated cDNA sequences were compared to sequences in the EMBL DNA database using the computer algorithm BLASTN. Comparisons of DNA sequences provided in SEQ ID NOS: 1–35, to sequences in the EMBL DNA database (using BLASTN) were made as of November, 2000, using Version 2.0.11 [Jan 20, 2000], and the following Unix running command: blastall -p blast d embldb -e 10 -G0 -E0 -r 1 -v 30 -b 30 -i queryseq -o.

The sequences of SEQ ID NOS: 1, 3, 4, 6–11, 13, 18, 21, 22, 24, 25, 28–30, 33 and 34 were determined to have less than 50% identity, determined as described above, to sequences in the EMBL database using the computer algorithm BLASTN, as described above. The sequences of SEQ ID NOS: 2, 12, 14–16, 20 and 35 were determined to have less than 75% identity, determined as described above, to sequences in the EMBL database using the computer algorithm BLASTN, as described above. The sequences of SEQ ID NOS: 17, 19, 23 and 27 were determined to have less than 90% identity, determined as described above, to sequences in the EMBL database using the computer algorithm BLASTN, as described above. Finally, the sequences of SEQ ID NOS: 5, 26 and 32 were determined to have less than 98% identity, determined as described above, to sequences in the EMBL database using the computer algorithm BLASTN, as described above.

BLASTP Polypeptide Analysis

The sequences of SEQ ID NOS: 37, 41, 42, 44, 46–50, 55, 56 and 59 were determined to have less than 50% identity, determined as described above, to sequences in the SwissProt database using the computer algorithm BLASTP, as described above. The sequences of SEQ ID NOS: 36, 38, 43, 45 and 60 were determined to have less than 75% identity, determined as described above, to sequences in the SwissProt database using the computer algorithm BLASTP, as described above. The sequences of SEQ ID NOS: 39, 54 and 58 were determined to have less than 90% identity, determined as described above, to sequences in the SwissProt database using the computer algorithm BLASTP, as described above. Finally, the sequences of SEQ ID NOS: 53, 57, 62 and 65 were determined to have less than 98% identity, determined as described above, to sequences in the SwissProt database using the computer algorithm BLASTP, as described above.

BLASTX Polynucleotide Analysis

The sequences of SEQ ED NOS: 2–4, 6–16, 18, 22–24, 26–30 and 33–35 were determined to have less than 50% identity, determined as described above, to sequences in the SwissProt database using the computer algorithm BLASTX, as described above. The sequences of SEQ ID NOS: 1, 19, 20, 25 and 32 were determined to have less than 75% identity, determined as described above, to sequences in the SwissProt database using the computer algorithm BLASTX, as described above. Finally, the sequences of SEQ ID NOS: 5, 17, 21 and 31 were determined to have less than 90% identity, determined as described above, to sequences in the SwissProt database using the computer algorithm BLASTX, as described above.

EXAMPLE 2

Isolation and Characterization of the Human Homolog of muKS1

This example demonstrates that an isolated cDNA may be used to isolate its homologue from a different species, the corresponding polypeptide may be expressed and the function of the polypeptide can be determined, starting the whole process from an isolated cDNA obtained as described above.

Analysis of RNA Transcripts by Northern Blotting

Northern analysis to determine the size and distribution of mRNA for the clone muKS1 (SEQ ID NO: 66; isolated from a mouse keratinocyte stem cell cDNA library using high-throughput sequencing as described above) was performed by probing murine tissue mRNA blots with a probe consisting of nucleotides 268–499 of muKS1, radioactively labeled with $[\alpha^{32}P]$-dCTP. Prehybridization, hybridization, washing and probe labeling were performed as described in Sambrook et al., Ibid. mRNA for muKS1 was 1.6 kb in size and was observed to be most abundant in brain, lung, muscle and heart. Expression could also be detected in lower intestine, skin and kidney. No detectable signal was found in testis, spleen, liver, thymus and stomach.

Human Homologue of muKS1

MuKS1 (SEQ ID NO: 66) was used to search the EMBL database (Release 50 plus updates to June, 1998) to identify human EST homologues. The top three homologies were to the following ESTs: accession numbers AA643952, HS1301003 and AA865643. These showed 92.63% identity over 285 nucleotides, 93.64% over 283 nucleotides and 94.035% over 285 nucleotides, respectively. Frame shifts were identified in AA643952 and HS1301003 when translated. Combination of all three ESTs identified the human homologue huKS1 (SEQ ID NO: 67) and translated polypeptide SEQ ID NO: 67. Alignment of muKS1 and huKS1 polypeptides indicated 95% identity over 96 amino acids.

Bacterial Expression and Purification of muKS1 and huKS1

Polynucleotides 269–502 of muKS1 (SEQ ID NO: 69), encoding amino acids 23–99 of polypeptide muKS1 (SEQ ID NO: 70), and polynucleotides 55–288 of huKS1 (SEQ ID NO: 71), encoding amino acids 19–95 of polypeptide huKS1 (SEQ ID NO: 72), were cloned into the bacterial expression vector pET-16b (Novagen, Madison, Wis.), which contains a bacterial leader sequence and N-terminal 6×Histidine tag. These constructs were transformed into competent *E. coli* BL21(DE3) (Novagen) as described in Sambrook et al., Ibid.

Starter cultures of recombinant *E. coli* BL21(DE3) (Novagen) transformed with bacterial expression vector pET16b containing SEQ ID NO: 69 (muKS1a) and SEQ ID NO: 71 (hUKS1a) were grown in NZY broth containing 100 μg/ml ampicillin (Gibco-BRL Life Technologies) at 37° C. Cultures were spun down and used to inoculate 800 ml of NZY broth and 100 μg/ml ampicillin. Cultures were grown until the $OD_{595}$ of the cells was between 0.4 and 0.8. Bacterial expression was induced for 3 hours with 1 mM IPTG. Bacterial expression produced an induced band of approximately 15 kDa for muKS1a and huKS1a.

MuKS1a and huKS1a were expressed in insoluble inclusion bodies. In order to purify the polypeptides, bacterial cell pellets were re-suspended in lysis buffer (20 mM Tris-HCl pH 8.0, 10 mM β-Mercaptoethanol, 1 mM PMSF). To the lysed cells, 1% NP-40 was added and the mix incubated on ice for 10 minutes. Lysates were further disrupted by sonication on ice at 95 W for 4×15 seconds and then centrifuged for 10 minutes at 18,000 rpm to pellet the inclusion bodies.

The pellet containing the inclusion bodies was re-suspended in lysis buffer containing 0.5% w/v CHAPS and sonicated for 5–10 seconds. This mix was stored on ice for 1 hour, centrifuged at 14,000 rpm for 15 minutes at 4° C. and the supernatant discarded. The pellet was once more re-suspended in lysis buffer containing 0.5% w/v CHAPS, sonicated, centrifuged and the supernatant removed as before. The pellet was re-suspended in solubilizing buffer (6 M guanidine HCl, 0.5 M NaCl, 20 mM Tris-HCl pH 8.0), sonicated at 95 W for 4×15 sec and centrifuged for 10 minutes at 18,000 rpm and 4° C. to remove debris. The supernatant was stored at 4° C. MuKS1a and huKS1a were purified by virtue of the N-terminal 6× histidine tag contained within the bacterial leader sequence, using a Nickel-Chelating sepharose column (Amersham Pharmacia, Uppsala, Sweden) and following the manufacturer's protocol. Proteins were purified twice over the column to reduce endotoxin contamination. In order to re-fold the proteins once purified, the protein solution was dialysed in a 4 M-2 M urea gradient in 20 mM Tris-HCl pH 7.5 containing 10% glycerol overnight at 4° C. The protein was then further dialysed 2× against 2 litres of 20 mM Tris-HCl pH 7.5 containing 10% glycerol.

Injection of Bacterially Expressed muKS1a into Nude Mice

Two nude nice were anaesthetised intraperitoneally with 75 μl of ⅟₁₀ dilution of Hypnorn (Janssen Pharmaceuticals, Buckinghamshire, England) in phosphate buffered saline. 20 μg of bacterially expressed muKS1a (SEQ ID NO: 70) was injected subcutaneously in the left hind foot, ear and left hand side of the back. The same volume of phosphate buffered saline was injected in the same sites but on the right hand side of the same animal. Mice were left for 18 hours and then examined for inflammation. Both mice showed a red swelling in the ear and foot sites injected with the bacterially expressed protein. No obvious inflammation could be identified in either back site. Mice were culled and biopsies taken from the ear, back and foot sites and fixed in 3.7% formol saline. Biopsies were embedded, sectioned and stained with Haemotoxylin and eosin. Sites injected with muKS1a had a marked increase in polymorphonuclear granulocytes, whereas sites injected with phosphate buffered saline had a low background infiltrate of polymorphonuclear granulocytes.

Chemokines are a large superfamily of highly basic secreted proteins with a broad number of functions (Baggiolini et al., *Annu. Rev. Immunol.* 15:675–705, 1997; Ward et al., *Immunity* 9:1–11, 1998; Horuk, Nature 393:524–525, 1998). The polypeptide sequences of muKS1 and huKS1 have similarity to CXC chemokines, suggesting that this protein will act like other CXC chemokines. The in vivo data from nude mice supports this hypothesis. This chemokine-like protein may therefore be expected to stimulate leukocyte, epithelial, stromal and neuronal cell migration, promote angiogenesis and vascular development, promote neuronal patterning, hematopoietic stem cell mobilization, keratinocyte and epithelial stem cell patterning and development, activation and proliferation of leukocytes, and promotion of migration in wound healing events. It has recently been shown that receptors to chemokines act as co-receptors for HIV-1 infection of CD4+ cells (Cairns et al., *Nature Medicine* 4:563–568, 1998) and that high circulating levels of chemokines can render a degree of immunity to those exposed to the HIV virus (Zagury et al., *Proc. Natl. Acad Sci. USA* 95:3857–3861, 1998). This novel gene and its encoded protein may thus be usefully employed as regulators of epithelial, lymphoid, myeloid, stromal and neuronal cells migration and cancers; as agents for the treatment of cancers, neuro-degenerative diseases, inflammatory autoimmune diseases such as psoriasis, asthma and Crohns disease; for use in wound healing; and as agents for the prevention of HIV-1 binding and infection of leukocytes.

SEQ ID NOS: 1–72 are set out in the attached Sequence Listing. The codes for nucleotide sequences used in the attached Sequence Listing, including the symbol "n," conform to WIPO Standard ST.25 (1998), Appendix 2, Table 1.

All references cited herein, including patent references and non-patent publications, are hereby incorporated by reference in their entireties.

While in the foregoing specification this invention has been described in relation to certain preferred embodiments, and many details have been set forth for purposes of illustration, it will be apparent to those skilled in the art that the invention is susceptible to additional embodiments and that certain of the details described herein may be varied considerably without departing from the basic principles of the invention.

We claim:

1. An isolated polypeptide encoded by a polynucleotide of SEQ ID NO: 12.

2. An isolated polypeptide comprising an amino acid sequence of SEQ ID NO: 46.

3. A composition comprising a polypeptide according to claim 2, and at least one component selected from the group consisting of: physiologically acceptable carriers and immunostimulants.

* * * * *

UNITED STATES PATENT AND TRADEMARK OFFICE
CERTIFICATE OF CORRECTION

PATENT NO.    : 6,380,362 B1                                              Page 1 of 1
DATED         : April 30, 2002
INVENTOR(S)   : James D. Watson et al.

It is certified that error appears in the above-identified patent and that said Letters Patent is hereby corrected as shown below:

<u>Title page,</u>
Item [60], provisional application no. change Dec. 22, 1999 to read -- Dec. 23, 1999 --.

Signed and Sealed this

Seventeenth Day of June, 2003

JAMES E. ROGAN
*Director of the United States Patent and Trademark Office*